US008673909B2

(12) United States Patent
Maddaford et al.

(10) Patent No.: US 8,673,909 B2
(45) Date of Patent: Mar. 18, 2014

(54) INDOLE COMPOUNDS AND METHODS FOR TREATING VISCERAL PAIN

(75) Inventors: Shawn Maddaford, Mississauga (CA); Jailall Ramnauth, Brampton (CA); Suman Rakhit, Mississauga (CA); Joanne Patman, Mississauga (CA); Paul Renton, Toronto (CA); Subhash C. Annedi, Mississauga (CA); John S. Andrews, Mississauga (CA); Gabriela Mladenova, Thornhill (CA)

(73) Assignee: NeurAxon, Inc., Mississauga (CA)

(*) Notice: Subject to any disclaimer, the term of this patent is extended or adjusted under 35 U.S.C. 154(b) by 0 days.

(21) Appl. No.: 12/272,775

(22) Filed: Nov. 17, 2008

(65) Prior Publication Data

US 2009/0192157 A1    Jul. 30, 2009

Related U.S. Application Data

(60) Provisional application No. 61/133,930, filed on Jul. 3, 2008, provisional application No. 60/988,757, filed on Nov. 16, 2007.

(51) Int. Cl.
A61K 31/535    (2006.01)
A61K 31/44     (2006.01)
A61K 31/445    (2006.01)
A61K 31/40     (2006.01)
C07D 401/00    (2006.01)
C07D 411/00    (2006.01)
C07D 209/04    (2006.01)

(52) U.S. Cl.
USPC ........ 514/235.2; 514/305; 514/323; 514/339; 514/304; 514/414; 546/277.4; 548/467; 548/466

(58) Field of Classification Search
None
See application file for complete search history.

(56) References Cited

U.S. PATENT DOCUMENTS

| 4,324,790 | A  | 4/1982  | Guillaume et al. |
|-----------|----|---------|------------------|
| 4,816,470 | A  | 3/1989  | Dowle et al.     |
| 4,816,560 | A  | 3/1989  | Verdini et al.   |
| 4,839,377 | A  | 6/1989  | Bays et al.      |
| 4,894,387 | A  | 1/1990  | Butina et al.    |
| 4,994,483 | A  | 2/1991  | Oxford et al.    |
| 5,037,845 | A  | 8/1991  | Oxford           |
| 5,070,102 | A  | 12/1991 | Traber et al.    |
| 5,103,020 | A  | 4/1992  | Albinson et al.  |
| 5,200,410 | A  | 4/1993  | Traber et al.    |
| 5,234,942 | A  | 8/1993  | Bernstein et al. |
| 5,270,333 | A  | 12/1993 | Bays et al.      |
| 5,331,005 | A  | 7/1994  | Calderó Ges et al. |
| 5,399,574 | A  | 3/1995  | Robertson et al. |
| 5,466,699 | A  | 11/1995 | Robertson et al. |
| 5,468,768 | A  | 11/1995 | Cipollina et al. |
| 5,708,008 | A  | 1/1998  | Audia et al.     |
| 5,863,935 | A  | 1/1999  | Robertson et al. |
| 5,874,427 | A  | 2/1999  | Filla et al.     |
| 5,998,438 | A  | 12/1999 | Slassi et al.    |
| 6,090,839 | A  | 7/2000  | Adams et al.     |
| 6,093,716 | A  | 7/2000  | Davis et al.     |
| 6,242,447 | B1 | 6/2001  | Demopulos et al. |
| 6,255,334 | B1 | 7/2001  | Sands            |
| 6,380,201 | B1 | 4/2002  | Johnson et al.   |
| 6,562,846 | B2 | 5/2003  | Sit et al.       |
| 6,750,242 | B1 | 6/2004  | Gurley et al.    |
| 6,861,443 | B2 | 3/2005  | Gurley et al.    |
| 7,141,595 | B2 | 11/2006 | Ramnauth et al.  |
| 7,375,219 | B2 | 5/2008  | Maddaford et al. |
| 7,674,809 | B2 | 3/2010  | Makovec et al.   |
| 7,951,940 | B2 | 5/2011  | Maddaford et al. |
| 7,989,447 | B2 | 8/2011  | Maddaford et al. |
| 2003/0064991 | A1 | 4/2003 | Harriman et al.  |
| 2003/0203055 | A1 | 10/2003 | Rao et al.      |
| 2004/0142935 | A1 | 7/2004 | Schiemann et al. |
| 2004/0259891 | A1 | 12/2004 | Agarwal et al.  |
| 2005/0032791 | A1 | 2/2005 | Merc-Vidal et al.|
| 2005/0075348 | A1 | 4/2005 | Harriman et al.  |
| 2005/0244389 | A1 | 11/2005 | Fioramonti et al.|
| 2005/0256182 | A1 | 11/2005 | Sutter et al.   |
| 2006/0009512 | A1 | 1/2006 | Curwen et al.    |
| 2006/0258721 | A1 | 11/2006 | Maddaford et al.|
| 2007/0105943 | A1 | 5/2007 | Nakamoto et al.  |
| 2007/0254940 | A1 | 11/2007 | Maddaford et al.|
| 2008/0234237 | A1 | 9/2008 | Maddaford et al. |

(Continued)

FOREIGN PATENT DOCUMENTS

CA    2380775    2/2002
CA    2498644    9/2005

(Continued)

OTHER PUBLICATIONS

Nicolodi, M, et al. "Visceral Pain Threshold is Deeply Lowered Far From the Head in Migraine", Headache, 34(1), 1994, 12-19.*
Zhang, Pharmacology Biochemistry and Behavior 77 (2004) 145-153.*
Abdel-Magid et al., "Reductive Amination of Aldehydes and Ketones with Sodium Triacetoxyborohydride. Studies on Direct and Indirect Reductive Amination Procedures," J. Org. Chem. 61(11): 3849-3852, 1996.
Acton et al., "Benzoyl 2-Methyl Indoles as Selective PPARgamma Modulators," Bioorg. Med. Chem. Lett. 15(2):357-362, 2005.
Adachi et al., "Aminohaloborane in Organic Synthesis IX. Exclusive Ortho Acylation Reaction of N-Monoaminoalkylanilines," Chem. Pharm. Bull. 33(5): 1826-1835, 1985.
Ahn and Basbaum, "Where do Triptans Act in the Treatment of Migraine?" Pain 115(1-2):1-4, 2005.

(Continued)

Primary Examiner — Nyeemah A Grazier
(74) Attorney, Agent, or Firm — Clark & Elbing LLP

(57) ABSTRACT

The invention features methods of treating visceral pain or a condition in a mammal caused by the action of nitric oxide synthase (NOS) or by the action of serotonin 5HT1D/1B receptors, by administering to a patient in need thereof a therapeutically effective amount of an indole compound of Formula (I), or a pharmaceutically acceptable salt or prodrug thereof. The methods of the invention may further comprise the administration of additional therapeutic agent. The invention also features new compounds of Formula (I), pharmaceutical compositions thereof, and methods of resolving enantiomeric mixtures.

21 Claims, 12 Drawing Sheets

(56) References Cited

U.S. PATENT DOCUMENTS

| | | | |
|---|---|---|---|
| 2008/0249302 | A1 | 10/2008 | Maddaford et al. |
| 2009/0131503 | A1 | 5/2009 | Annedi et al. |
| 2009/0163451 | A1 | 6/2009 | Porreca et al. |

FOREIGN PATENT DOCUMENTS

| | | |
|---|---|---|
| EP | 0262873 | 4/1988 |
| EP | 0438230 | 7/1991 |
| EP | 0574618 | 12/1993 |
| EP | 1571142 | 9/2005 |
| JP | 6212151 | 8/1994 |
| JP | 2000280626 | 10/2000 |
| JP | 2005129430 | 5/2005 |
| WO | WO 91/18897 | 12/1991 |
| WO | WO 92/13856 | 8/1992 |
| WO | WO 93/11106 | 6/1993 |
| WO | WO 94/03446 | 2/1994 |
| WO | WO 97/47302 | 12/1997 |
| WO | WO 98/11895 | 3/1998 |
| WO | WO-9850380 A1 | 11/1998 |
| WO | WO 00/00487 | 1/2000 |
| WO | WO 00/17198 | 3/2000 |
| WO | WO 00/38677 | 7/2000 |
| WO | WO 01/12187 | 2/2001 |
| WO | WO 01/32619 | 5/2001 |
| WO | WO 02/16318 | 2/2002 |
| WO | WO 03/051275 | 6/2003 |
| WO | WO 03051274 A2 * | 6/2003 |
| WO | WO 2004/014885 | 2/2004 |
| WO | WO 2005/013974 | 2/2005 |
| WO | WO 2005/024416 | 3/2005 |
| WO | WO 2005/090282 | 9/2005 |
| WO | WO 2007/063418 | 6/2007 |
| WO | WO 2007/118314 | 10/2007 |

OTHER PUBLICATIONS

Ahn and Basbaum, "Tissue Injury Regulates Serotonin 1D Receptor Expression: Implications for the Control of Migraine and Inflammatory Pain," *J. Neurosci.* 26(32):8332-8338, 2006.

Al-Chaer et al., "A New Model of Chronic Visceral Hypersensitivity in Adult Rats Induced by Colon Irritation During Postnatal Development," *Gastroenterology* 119:1276-1285, 2000.

Anderson et al., "Palladium-Catalyzed Amination of Aryl Nonaflates," *J. Org. Chem.* 68(25): 9563-9573, 2003.

Antilla and Buchwald, Copper-Catalyzed Coupling of Arylboronic Acids and Amines, *Org. Lett.* 3(13): 2077-2079, 2001.

Arvieu et al., "Sumatriptan Inhibits the Release of CGRP and Substance P from the Rat Spinal Cord," *Neuroreport* 7(12):1973-1976, 1996.

Azpiroz et al., "Mechanisms of Hypersensitivity in IBS and Functional Disorders," *Neurogastroenterol. Motil.* 19(1 Suppl):62-88, 2007.

Baati et al., "An Improved Method for the Preparation of Amidines via Thiophenylimidic Esters," *Synthesis* 927-929, 1999.

Bartsch et al., "Activation of 5-HT(1B/1D) Receptor in the Periaqueductal Gray Inhibits Nociception," *Ann. Neurol.* 56(3):371-381, 2004.

Berridge, "The Mode of Action of 5-Hydroxytryptamine," *J. Exp. Biol.* 56(2):311-321, 1972.

Bingham et al., "Inhibition of Inflammation-Induced Thermal Hypersensitivity by Sumatriptan Through Activation of 5-HT(1B/1D) Receptors," *Exp. Neurol.* 167(1):65-73, 2001.

Blair et al., "Effect of Ring Fluorination on the Pharmacology of Hallucinogenic Tryptamines," *J. Med. Chem.* 43(24): 4701-4710, 2000.

Bornman et al., "Pathogenesis of Pain in Chronic Pancreatitis: Ongoing Enigma," *World J. Surg.* 27(11):1175-1182, 2003.

Bourdu et al., "Rectal Instillation of Butyrate Provides a Novel Clinically Relevant Model of Noninflammatory Colonic Hypersensitivity in Rats," *Gastroenterology* 128(7):1996-2008, 2005.

Bruinvels et al., "Localization of 5-HT1B, 5-HT1D alpha, 5-HT1E and 5-HT1F Receptor Messenger RNA in Rodent and Primate Brain," *Neuropharmacology* 33(3-4):367-386, 1994.

Burgess et al., "Time-Dependent Descending Facilitation from the Rostral Ventromedial Medulla Maintains, but does not Initiate, Neuropathic Pain," *J. Neurosci.* 22(12):5129-5136, 2002.

Buscher et al., "Chronic Pancreatitis Patients Show Hyperalgesia of Central Origin: A Pilot Study," *Eur. J. Pain* 10(4):363-370, 2006.

Castro et al., "Differential Distribution of [$^3$H]Sumatriptan Binding Sites (5-HT1B, 5-HT1D and 5-HT1F Receptors) in Human Brain: Focus on Brainstem and Spinal Cord," *Neuropharmacology* 36(4-5):535-542, 1997.

Castro et al., "Enhancement of Oral Absorption in Selective 5-HT$_{1D}$ Receptor Agonists: Fluorinated 3-[3-(Piperidin-1-yl)propyl]indoles," *J. Med. Chem.*, 41(51): 2667-2670, 1998.

Cervero and Laird, "Visceral Pain," *Lancet* 353(9170):2145-2148, 1999.

Coe et al., "Convenient Preparation of N-Substituted Indoles by Modified Leimgruber-Batcho Indole Synthesis," *Tetrahedron Lett.* 37(34):6045-6048, 1996.

Cooper et al., "2-Aryl Indole NK1 Receptor Antagonists: Optimisation of Indole Substitution," *Bioorg. Med. Chem. Lett.* 11(9):1233-1236, 2001.

De Ponti and Tonini, "Irritable Bowel Syndrome: New Agents Targeting Serotonin Receptor Subtypes," *Drugs* 61(3):317-332, 2001.

Dimcevski et al., "Pain in Chronic Pancreatitis: the Role of Reorganization in the Central Nervous System," *Gastroenterology* 132(4):1546-1556, 2007.

Dimcevski et al., "Assessment of Experimental Pain from Skin, Muscle, and Esophagus in Patients with Chronic Pancreatitis," *Pancreas* 35(1):22-29, 2007.

Dorwald, "Side Reactions in Organic Synthesis," *WILEY-VCH*, 2005.

Egle et al., "3-(2-Pyrrolidin-1-ylethyl)-5-(1,2,3,6-Tetrahydropyridin-4-yl)-1H-indole Derivatives as High Affinity Human 5-HT(1B/1D) Ligands," *Bioorg. Med. Chem. Lett.* 14(3): 727-729, 2004.

Ekbom, "Treatment of Cluster Headache: Clinical Trials, Design and Results," *Cephalalgia* 15(Suppl 15):33-36, 1995.

Ghelardini et al., "Involvement of Central Cholinergic System in Antinociception Induced by Sumatriptan in Mouse," *Int. J. Clin. Pharmacol. Res.* 17(2-3):105-109, 1997.

Giamberardino, "Referred Muscle Pain/Hyperalgesia and Central Sensitization," *J. Rehabil. Med.* (41 Suppl):85-88, 2003.

Hauer et al., "Gabapentin Successfully Manages Chronic Unexplained Irritability in Children with Severe Neurologic Impairment," *Pediatrics* 119(2):e519-522, 2007.

Heaney and Ley, "1-Benzylindole [1H-Indole, 1-(phenylmethyl)-]," *Org. Syn.* 6:104, 1988; *Org. Syn* 54:58, 1974.

Heuring and Peroutka, "Characterization of a Novel 3H-5-Hydroxytryptamine Binding Site Subtype in Bovine Brain Membranes," *J. Neurosci.* 7(3): 894-903, 1987.

Hoyer et al., "Characterization of the 5-HT1B Recognition Site in Rat Brain: Binding Studies with (-)[125I]Iodocyanopindolol," *Eur. J. Pharmacol.* 118(1-2):1-12, 1985.

Huang and Buchwald, "New Ammonia Equivalents for the Pd-Catalyzed Amination of Aryl Halides," *Org. Lett.* 3(21):3417-3419, 2001.

Humphrey and Goadsby, "The Mode of Action of Sumatriptan is Vascular? A Debate," *Cephalalgia* 14(6):401-410, 1994.

Humphrey and Kuethe, "Practical Methodologies for the Synthesis of Indoles," *Chem. Rev.* 106(7):2875-2911, 2006.

Jain and Kulkarni, "Antinociceptive Effect of Sumatriptan in Mice," *Indian J. Exp. Biol.* 36(10):973-979, 1998.

Jennings et al., "Effects of Sumatriptan on Rat Medullary Dorsal Horn Neurons," *Pain* 111(1-2):30-37, 2004.

Johnson et al., "Preparation of Indole and Carbazole Derivatives as Serotonin Agonists," *Chemical Abstracts* 128:192544, 1998.

Johnson et al., "Preparation of Piperidinylindoles and Related Compounds as Serotonin 5-Ht1F Agonists," *Chemical Abstracts* 128:257330, 1998.

Jordan, "Tamoxifen: A Most Unlikely Pioneering Medicine," *Nature Reviews* 2(3):205-213 (2003).

(56) References Cited

OTHER PUBLICATIONS

Kayser et al., "The Antimigraine 5-Ht 1B/1D Receptor Agonists, Sumatriptan, Zolmitriptan and Dihydroergotamine, Attenuate Pain-Related Behaviour in a Rat Model of Trigeminal Neuropathic Pain," *Br. J. Pharmacol.* 137(8):1287-1297, 2002.

Kim and Chung, "An Experimental Model for Peripheral Neuropathy Produced by Segmental Spinal Nerve Ligation in the Rat," *Pain* 50(3):355-363, 1992.

Kitazawa et al., "Preparation of 1,4-Disubstituted Cyclic Amine Derivatives as Serotonin Antagonists," *Chemical Abstracts* 129:302552, 1998.

Kuyper et al., "High-Affinity Inhibitors of Dihydrofolate Reductase: Antimicrobial and Anticancer Activities of 7,8-Dialkyl-1,3-Diaminopyrrolo[3,2-f]Quinazolines with Small Molecular Size," *J. Med. Chem.* 39(4):892-903, 1996.

Levy et al., "Disruption of Communication Between Peripheral and Central Trigeminovascular Neurons Mediates the Antimigraine Action of 5HT 1B/1D Receptor Agonists," *Proc. Natl. Acad. Sci. USA* 101(12):4274-4279, 2004.

Li et al., "Voltage-Dependent Calcium Currents in Bulbospinal Neurons of Neonatal Rat Rostral Ventrolateral Medulla: Modulation by Alpha2-Adrenergic Receptors," *J. Neurophysiol.* 79(2):583-594, 1998.

Macor et al., "5-[(3-Nitropyrid-2-yl)Amino]Indoles: Novel Serotonin Agonists with Selectivity for the 5-HT1D Receptor. Variation of the C3 Substituent on the Indole Template Leads to Increased 5-HT1D Receptor Selectivity," *J. Med. Chem.* 37(16):2509-2512, 1994.

Macor et al., "Use of 2,5-Dimethylpyrrole as an Amino-Protecting Group in an Efficient Synthesis of 5-Amino-3-[(N-Methyl-Pyrrolidin-2(R)-yl)Methyl]indole," *J. Org. Chem.* 59(24):7496-7498, 1994.

Mahindroo at al., "Novel Indole-Based Peroxisome Proliferator-Activated Receptor Agonists: Design, SAR, Structural Biology, and Biological Activities," *J. Med. Chem.* 48(26):8194-8208, 2005.

McKay, "The Preparation of N-Substituted-N[1]-nitroguanidines by the Reaction of Primary Amines with N-Alkyl-N-nitroso-N[1]-nitroguanidines," *J. Am. Chem. Soc.*, 71(6):1968-1970, 1949.

Nicholas et al., "Cellular Localization of Messenger RNA for beta-1 and beta-2 Adrenergic Receptors in Rat Brain: An In Situ Hybridization Study," *Neuroscience* 56(4):1023-1039, 1993.

Nikai et al., "Profound Reduction of Somatic and Visceral Pain in Mice by Intrathecal Administration of the Anti-migraine Drug, Sumatriptan," *Pain* 139(3):533-540, 2008.

Ottani et al., "Effect of Sumatriptan in Different Models of Pain in Rats," *Eur. J. Pharmacol.* 497(2):181-186, 2004.

Perregaard et al., "Selective, Centrally Acting Serotonin 5-HT2 Antagonists. 1. 2- and 6-Substituted 1-Phenyl-3-(4-Piperidinyl)-1H-Indoles," *J. Med. Chem.* 35(26): 4813-4822, 1992.

Potrebic et al., "Peptidergic Nociceptors of Both Trigeminal and Dorsal Root Ganglia Express Serotonin 1D Receptors: Implications for the Selective Antimigraine Action of Triptans," *J. Neurosci.* 23(34):10988-10997, 2003.

Price et al., "SB-216641 and BRL-15572—Compounds to Pharmacologically Discriminate h5-HT1B and h5-HT1D Receptors," *Naunyn. Schmiedebergs. Arch. Pharmacol.* 356(3):312-320, 1997.

Rényi et al., "Biochemical and Behavioural Effects of Isamoltane, a beta-Adrenoceptor Antagonist with Affinity for the 5-HT1B Receptor of Rat Brain," *Naunyn. Schmiedebergs. Arch. Pharmacol.* 343(1):1-6, 1991.

Rowley et al., "3-(4-Fluoropiperidin-3yl)-2-Phenylindoles as High Affinity, Selective, and Orally Bioavailable h5-HT(2A) Receptor Antagonists," *J. Med. Chem.* 44(10):1603-1614, 2001.

Russell et al., "3-[3-(Piperidin-1-yl)Propyl]Indoles as Highly Selective h5-HT(1D) Receptor Agonists," *J. Med. Chem.* 42(24):4981-5001, 1999.

Sparmann et al., "Pancreatic Fibrosis in Experimental Pancreatitis Induced by Dibutyltin Dichloride," *Gastroenterology* 112(5):1664-1672, 1997.

Speeter and Anthony, "The Action of Oxalyl Chloride on Indoles: A New Approach to Tryptamines," *J. Am. Chem. Soc.* 76(23):6208-6210, 1954.

Srivastava and Banik, "Bismuth Nitrate-Catalyzed Versatile Michael Reactions," *J. Org. Chem.* 68(6):2109-2114, 2003.

Stepanović-Petrović et al., "The Antinociceptive Effects of Anticonvulsants in a Mouse Visceral Pain Model," *Anesth. Analg.* 106(6):1897-1903, 2008.

Sternfeld et al., "Synthesis and Serotonergic Activity of 3-[2-(Pyrrolidin-1-yl)Ethyl]Indoles: Potent Agonists for the h5-HT1D Receptor with High Selectivity over the h5-HT1B Receptor," *J. Med. Chem.* 42(4):677-690, 1999.

Suh et al., "Novel Potent Antagonists of Transient Receptor Potential Channel, Vanilloid Subfamily Member 1: Structure-Activity Relationship of 1,3,-Diarylalkyl Thioureas Possessing New Vanilloid Equivalents," *J. Med. Chem.* 48(18):5823-5836, 2005.

van Niel et al., "Fluorination of 3-(3-(Piperidin-1-yl)Propyl)Indoles and 3-(3-(Piperazin-1-yl)Propyl)Indoles Gives Selective Human 5-HT1D Receptor Ligands with Improved Pharmacokinetic Profiles," *J. Med. Chem.* 42(12):2087-2104, 1999.

Vera-Portocarrero et al., "Nociception in Persistent Pancreatitis in Rats: Effects of Morphine and Neuropeptide Alterations," *Anesthesiology* 98(2):474-484, 2003.

Vera-Portocarrero and Westlund, "Attenuation of Nociception in a Model of Acute Pancreatitis by an NK-1 Antagonist," *Pharmacol. Biochem. Behav.* 77(3):631-640, 2004.

Vera-Portocarrero et al., "Descending Facilitation from the Rostral Ventromedial Medulla Maintains Visceral Pain in Rats with Experimental Pancreatitis," *Gastroenterology* 130(7):2155-2164, 2006.

Vera-Portocarrero et al., "Reversal of Inflammatory and Noninflammatory Visceral Pain by Central or Peripheral Actions of Sumatriptan," *Gastroenterology* 135(4):1369-1378, 2008.

Verne et al., "Hypersensitivity to Visceral and Cutaneous Pain in the Irritable Bowel Syndrome," *Pain* 93(1):7-14, 2001.

Wick et al., "Transient Receptor Potential Vanilloid 1, Calcitonin Gene-Related Peptide, and Substance P Mediate Nociception in Acute Pancreatitis," *Am. J. Physiol. Gastrointest. Liver Physiol.* 290(5):G959-G969, 2006.

Wiedenau and Blechert, "Facile Synthesis of 2-Benzylindoles," *Synthetic Commun.* 27(12):2033-2039, 1997.

Winston et al., "Acute Pancreatitis Results in Referred Mechanical Hypersensitivity and Neuropeptide Up-Regulation that can be Suppressed by the Protein Kinase Inhibitor k252a," *J. Pain* 4(6):329-337, 2003.

Wolfe et al., "Simple, Efficient Catalyst System for the Palladium-Catalyzed Amination of Aryl Chlorides, Bromides, and Triflates," *J. Org. Chem.* 65(4):1158-1174, 2000.

Zhuo and Gebhart, "Facilitation and Attenuation of a Visceral Nociceptive Reflex from the Rostroventral Medulla in the Rat," *Gastroenterology* 122(4):1007-1019, 2002.

Zhuo et al., "Biphasic Modulation of Spinal Visceral Nociceptive Transmission from the Rostroventral Medial Medulla in the Rat," *J. Neurophysiol.* 87(5):2225-2236, 2002.

Zochodne and Ho, "Sumatriptan Blocks Neurogenic Inflammation in the Peripheral Nerve Trunk," *Neurology* 44(1):161-163, 1994.

Non-Final Office Action for U.S. Appl. No. 12/272,656 on Jun. 11, 2009.

International Search Report for PCT/CA2008/002047 (mailed Mar. 2, 2009).

Bueno et al., "Serotonergic and Non-Serotonergic Targets in the Pharmacotherapy of Visceral Hypersensitivity," *Neurogastroenterol. Motil.* 19(1 Suppl):89-119, 2007.

Tack et al., "Role of Tension Receptors in Dyspeptic Patients with Hypersensitivity to Gastric Distention," *Gastroenterology* 127:1058-1066, 2004.

Buéno et al., "Pathobiology of Visceral Pain: Molecular Mechanisms and Therapeutic Implications III. Visceral Afferent Pathways: A Source of New Therapeutic Targets for Abdominal Pain," *Am. J. Physiol. Gastrointest. Liver Physiol.* 278:G670-G676 (2000).

Cervero, "Visceral Pain—Central Sensitisation," *Gut* 47:iv56-iv57 (Suppl IV) (2000).

Cervero and Laird, "Visceral Pain," *The Lancet*, 353:2145-2148 (1999).

(56) References Cited

OTHER PUBLICATIONS

Chang et al. "Brain Responses to Visceral and Somatic Stimuli in Patients with Irritable Bowel Syndrome with and Without Fibromyalgia," *Am. J. Gastroenterology* 98:1354-1361 (2003).

Renstrom Koskela, "Nitric Oxide in the Painful Bladder/Interstitial Cystitis," *J. Urol. Urogynäkol.* 14:18-19 (2007).

Price et al., "Peripheral and Central Contributions to Hyperalgesia in Irritable Bowel Syndrome," *J. Pain* 7:529-535 (2006).

"Pain: Clinical Updates" *International Association for the Study of Pain®*. vol. XIII, No. 6 (2005). http//:www.iasp-pain.org_AM_AMTemplate.cfm_Section=HOME&TEMPLATE=_CM_ContentDisplay.

Robinson and Gebhart, "Inside Information—The Unique Features of Visceral Sensation," *Mol. Interv.* 8:242-253 (2008).

Extended European Search Report for European Patent Application No. 08850557.3 dated Jan. 30, 2012 (5 Pages).

Lassen et al., "Nitric oxide synthase inhibition in migraine," *Lancet*, 349:401-402, 1997.

Mauskop, "Acute treatment of migraine headaches," *Seminars in Pain Medicine*, 2:72-75, 2004.

Rice, "Topical spinal administration of a nitric oxide synthase inhibitor prevents the hyper-reflexia associated with a rat model of persistent visceral pain," *Neurosci. Lett.*, 187:111-114, 1995.

Vallance and Leiper, "Blocking NO synthesis: how, where and why?" *Nat. Rev. Drug Discov.*, 1:939-950, 2002.

Aoki et al., "Novel neuronal nitric oxide synthase (nNOS) selective inhibitor, aplysinopsin-type indole alkaloid, from marine sponge *Hyrtios erecta,*" *Chem Pharm Bull.* 49:1372-1374 (2001).

\* cited by examiner

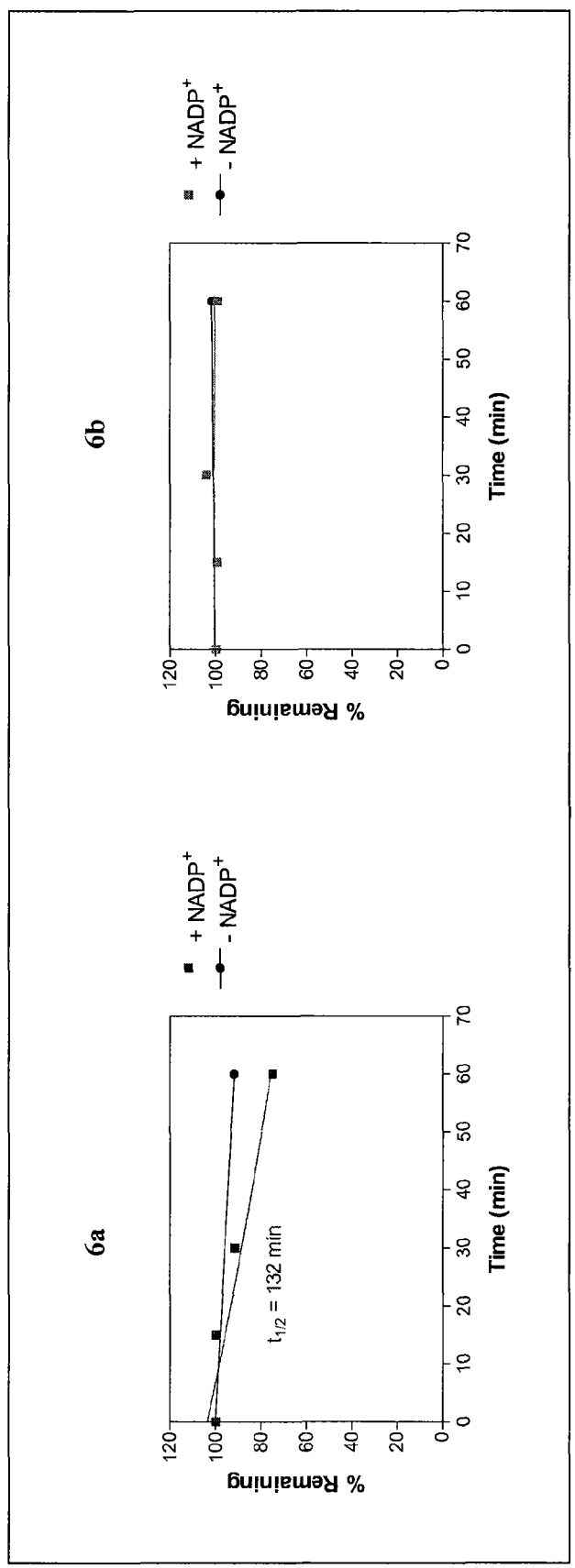
Figure 1. Stability of 6a and 6b in human liver microsomes over 60 minutes Figure 2. Stability of 18 in human liver micromes over 60 minutes.
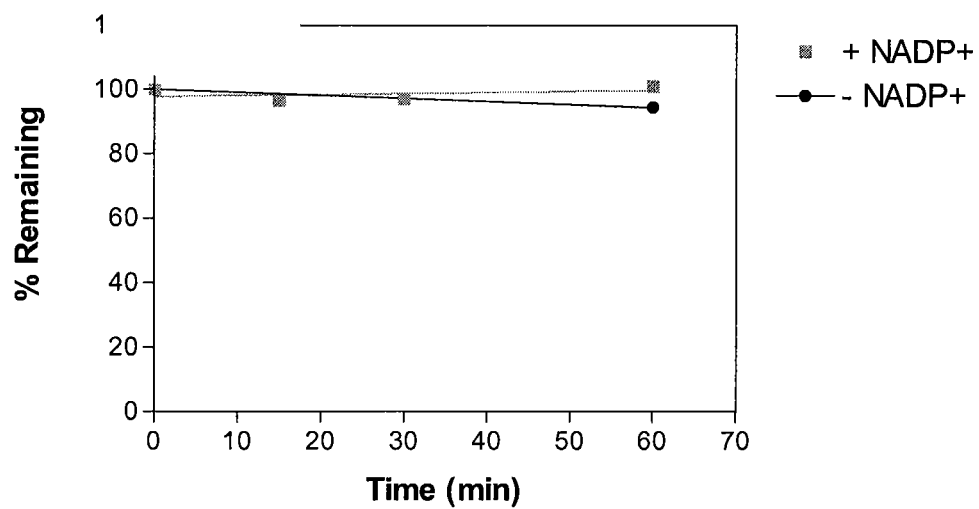

Figure 3. Effect of 6b on thermal hyperalgesia in the Chung model of neuropathic pain.
6b (30 mg/kg, i.p.) Attenuates Thermal Hyperalgesia of the Hindpaw in Rats with SNL
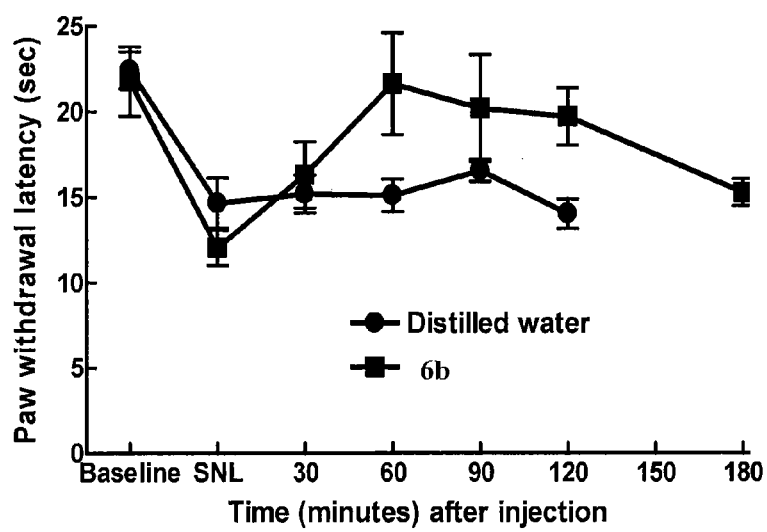

Figure 4. Effect of 6a on thermal hyperalgesia in the Chung model of neuropathic pain.
6a (30 mg/kg, i.p.) Attenuates Thermal Hyperalgesia of the Hindpaw in Rats with SNL
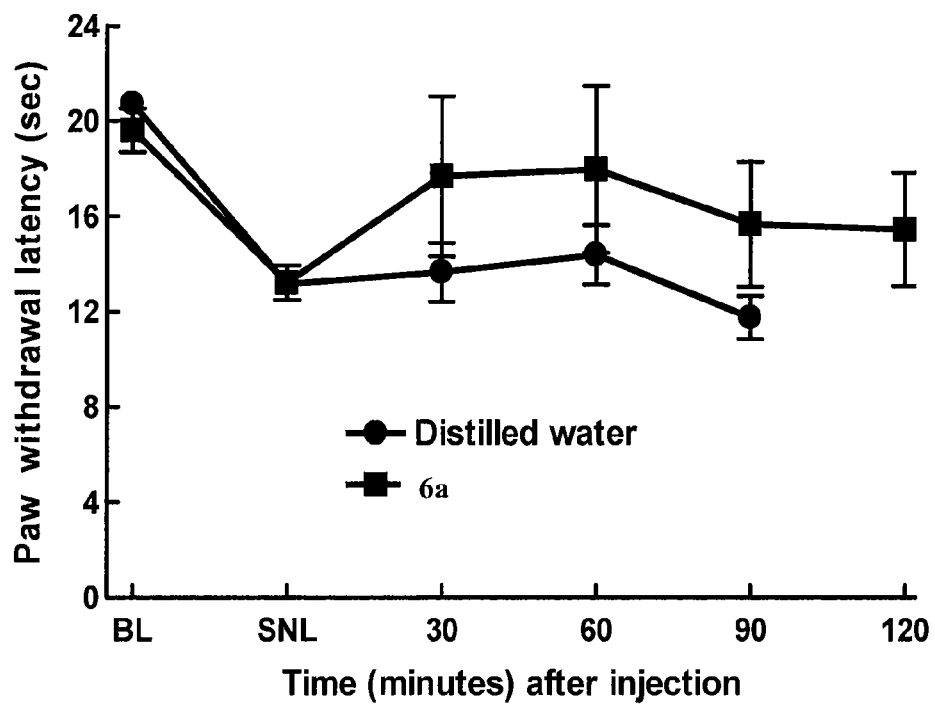

Figure 5. Effect of 6b on tactile allodynia in the Chung model of neuropathic pain.
6b (30 mg/kg, i.p.) May Attenuate Tactile Hyperesthesia of the Hindpaw in Rats with SNL
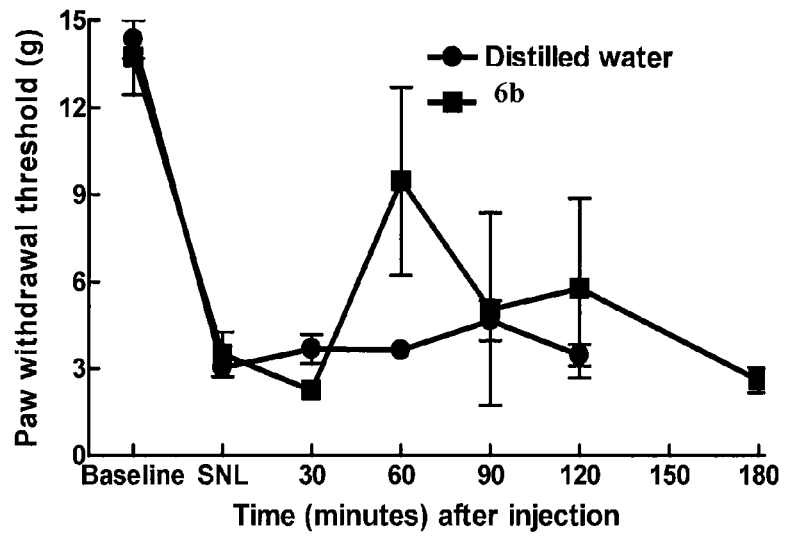

Figure 6. Effect of 6a on tactile allodynia in the Chung model of neuropathic pain.
6a (30 mg/kg, i.p.) Does Not Attenuate Tactile Hyperesthesia of the Hindpaw in Rats with SNL
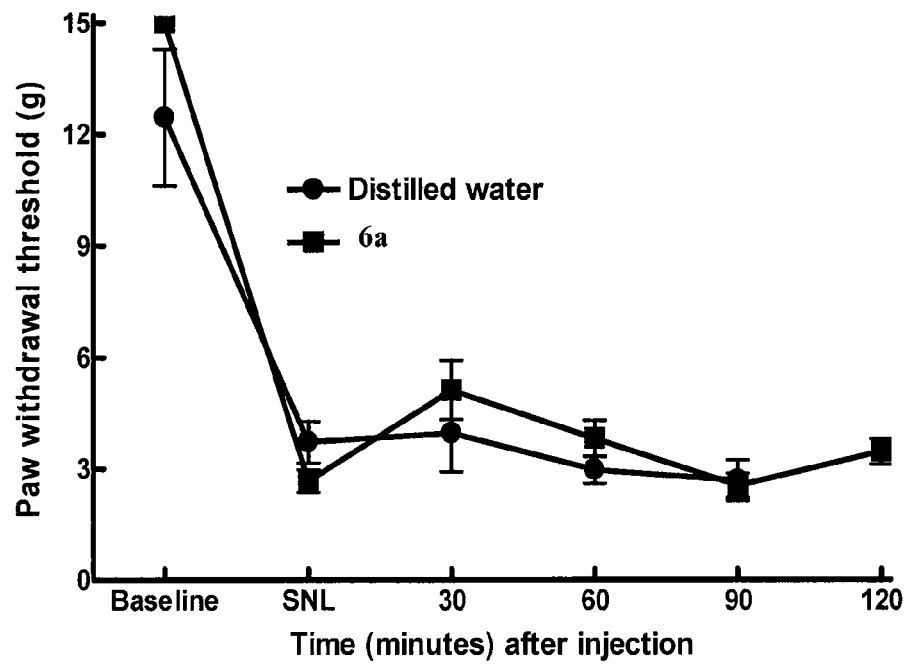

Figure 7. General testing protocol for the pancreatitis visceral pain model.
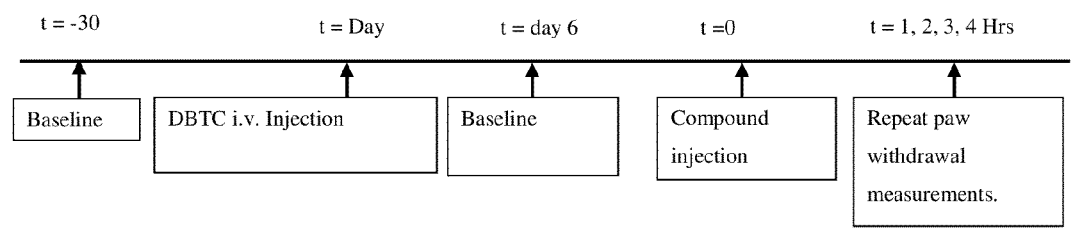
DBTC: Dibutyltin Dichloride

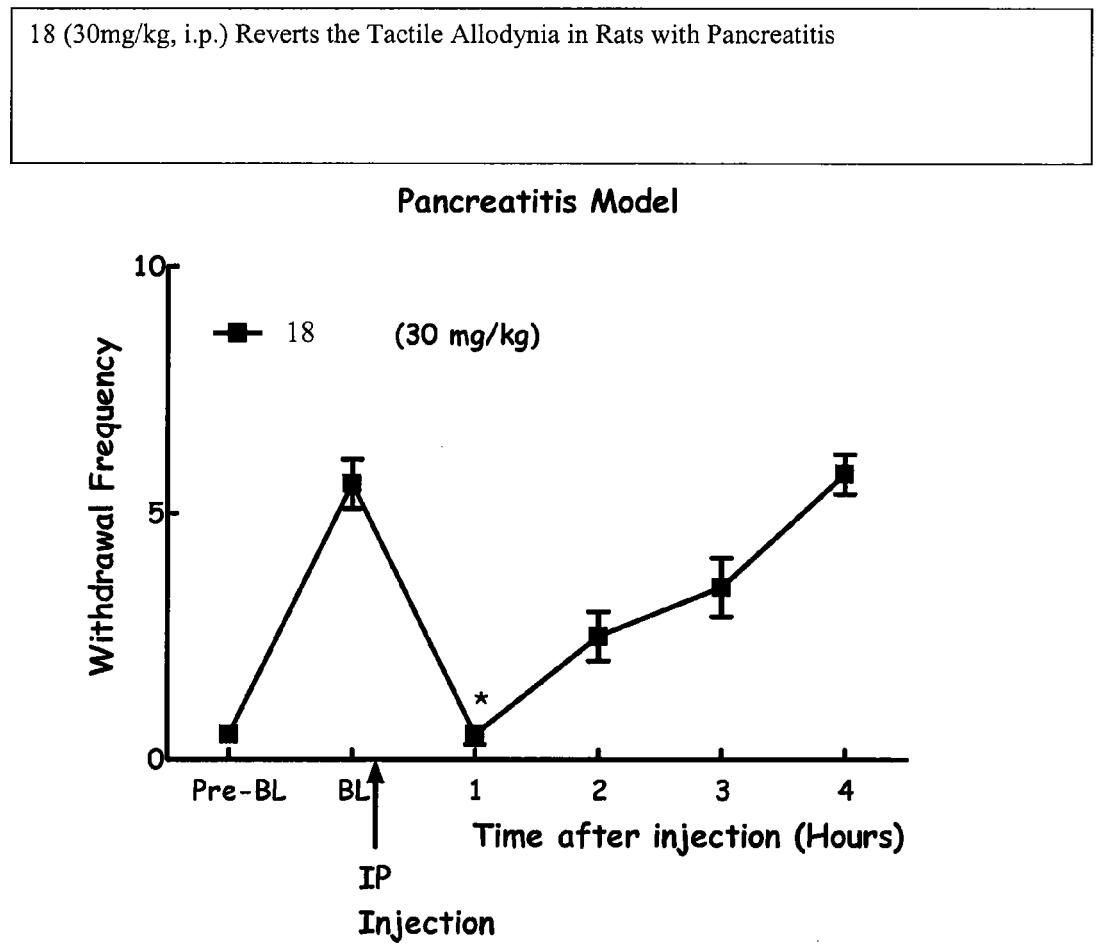
Figure 8. Effects of 18 in a pancreatitis visceral pain model.

Figure 9. Effects of 6b in a pancreatitis visceral pain model.
6b (30mg/kg, i.p.) Attenuates the Tactile Allodynia in Rats with Pancreatitis
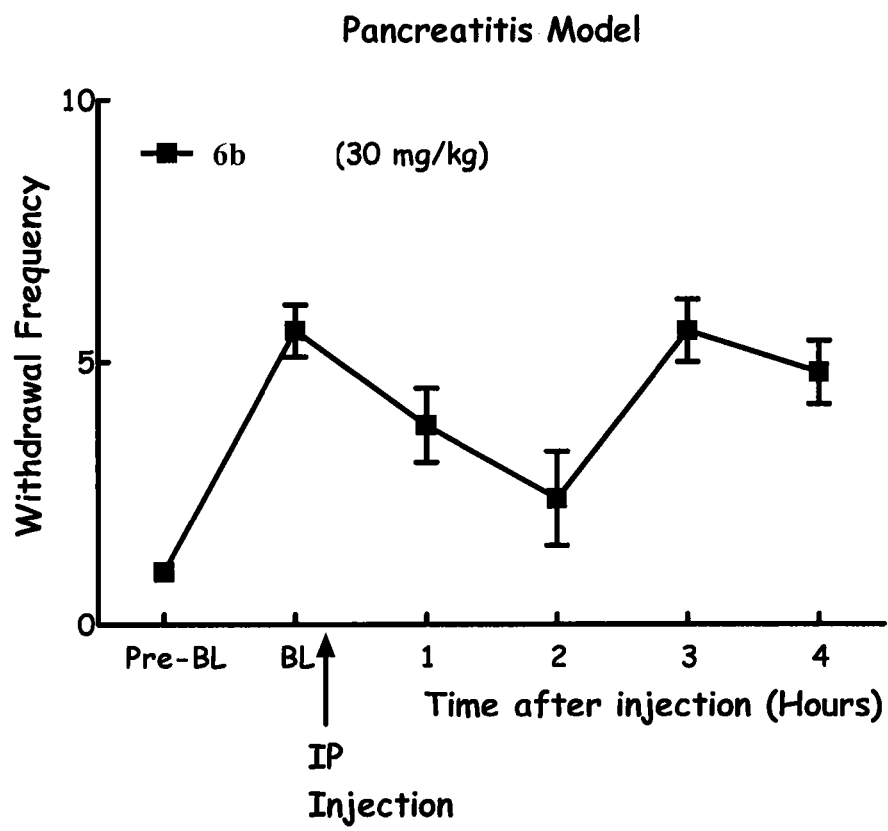

Figure 10. Effects of 18 in an IBS visceral pain model.
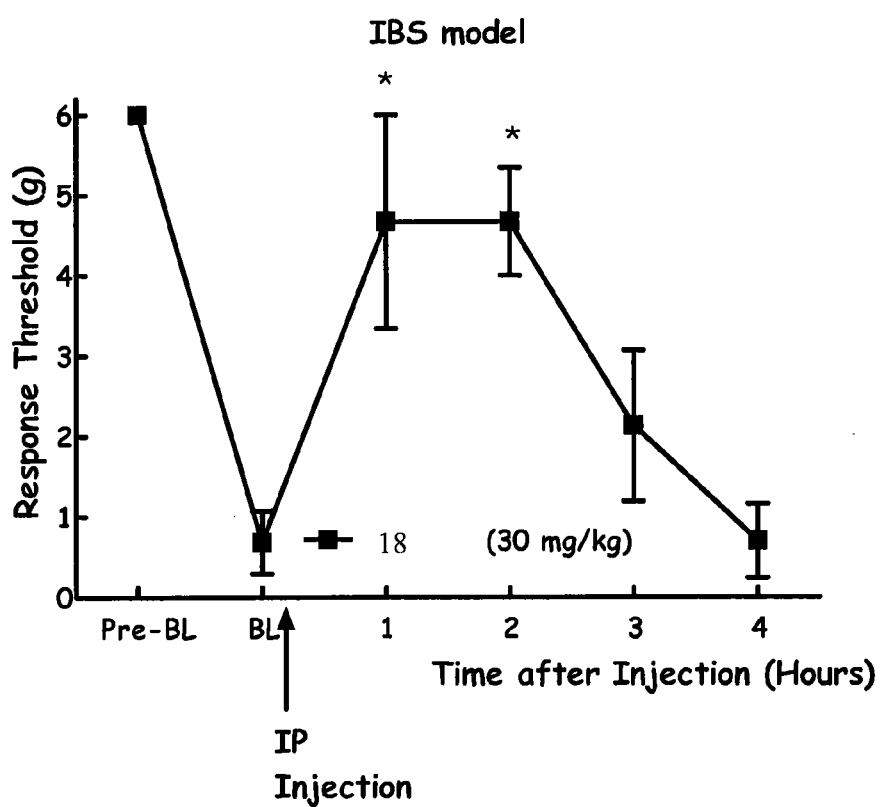

Figure 11. Effects of 6a in a pancreatitis visceral pain model.
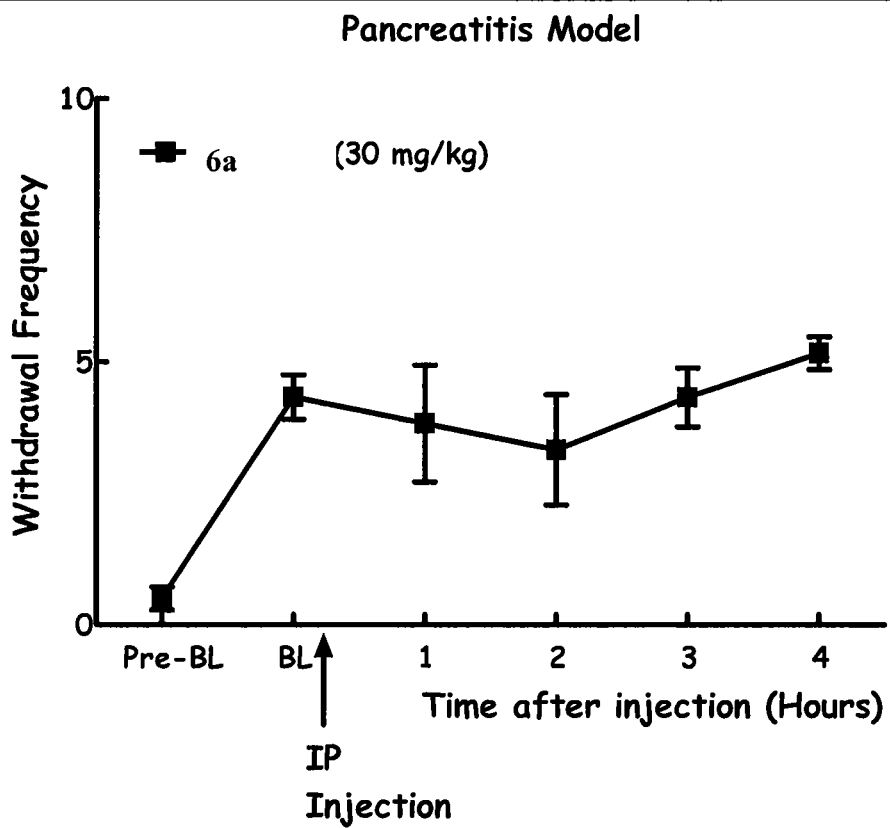

Figure 12. Effects of (27) in a pancreatitis visceral pain model.
Example 26 (Compound (27); 30mg/kg, i.p.) Reverts the Tactile Allodynia in Rats with Pancreatitis
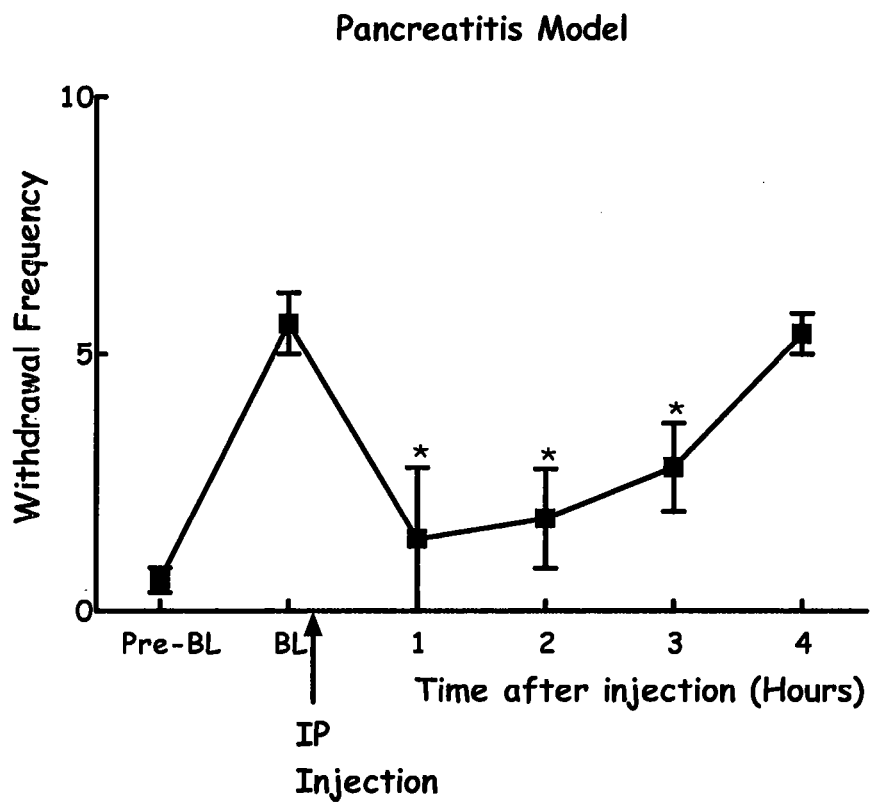
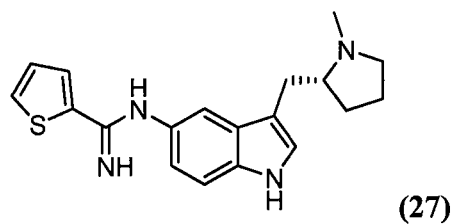
(27)

INDOLE COMPOUNDS AND METHODS FOR TREATING VISCERAL PAIN

CROSS-REFERENCE TO RELATED APPLICATIONS

This application claims benefit to U.S. Provisional Application Nos. 60/988,757, filed Nov. 16, 2007, and 61/133,930, filed Jul. 3, 2008, each of which is hereby incorporated by reference.

FIELD OF THE INVENTION

The invention relates to compounds and methods for treating visceral pain.

BACKGROUND OF THE INVENTION

Visceral pain is the most common form of pain and is one of the most difficult forms of pain to treat, often with the use of opioids. Visceral pain is distinct from somatic pain and is generally described as pain that originates from the body's internal cavities or organs and has five important clinical and sensory characteristics: (1) it is not evoked from all visceral organs (eg liver, kidney, lung); (2) it is not always linked to visceral injury (e.g., cutting an intestine does not evoke pain); (3) it is diffuse; (4) it is referred to other locations; and (5) it can be referred to other autonomic and motor reflexes (e.g., nausea, lower-back muscle tension from renal colic) (*Lancet*, 1999, 353, 2145-48). Several theories have been proposed for the mechanisms of visceral pain. In the first theory, the viscera are innervated by separate classes of neurons, one concerned with autonomic regulation and the other with sensory phenomena such as pain. The second theory suggests a single homogenous class of sensory receptors that are active at low frequencies (normal regulatory signals) or at high frequencies of activation (induced by intense pain signals). However, studies indicate that the viscera is innervated by two classes of nociceptive sensory receptors: high threshold (mostly mechanical receptors found in heart, vein, lung, airways, oesophagus, biliary system, small intestine, colon, ureter, airways, urinary bladder and uterus; activated by noxious stimuli) and low threshold intensity coding receptors that respond to innocuous and nocuous stimuli (heart, oesophagus, colon, urinary bladder and testes). Yet another theory suggests a component of afferent fibres that are normally unresponsive to stimuli (silent nociceptors) that can become activated or sensitized during inflammation (*Trends Neurosci.* 1992, 15, 374-78). Once sensitized, these nociceptors now respond to innocuous stimuli that normally occur in the internal organs resulting in an enhanced barrage of convergent input to the spinal cord and subsequently triggering central mechanisms that amplify the effect of the peripheral input.

Compounds for the treatment of visceral pain would therefore be highly desirable.

SUMMARY OF THE INVENTION

The invention features methods of treating visceral pain by administering to a patient in need thereof a therapeutically effective amount of a compound having the formula:

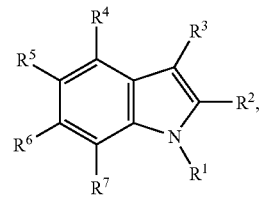

or a pharmaceutically acceptable salt or prodrug thereof, wherein, $R^1$ is H, optionally substituted $C_{1-6}$ alkyl, optionally substituted $C_{1-4}$ alkaryl, optionally substituted $C_{1-4}$ alkheterocyclyl, or optionally substituted $C_{3-8}$ cycloalkyl;

each of $R^2$ and $R^3$ is, independently, H, Hal, optionally substituted $C_{1-6}$ alkyl, optionally substituted $C_{6-10}$ aryl, optionally substituted $C_{1-4}$ alkaryl, optionally substituted $C_{2-9}$ bridged heterocyclyl, optionally substituted $C_{1-4}$ bridged alkheterocyclyl, optionally substituted $C_{2-9}$ heterocyclyl, or optionally substituted $C_{1-4}$ alkheterocyclyl;

each of $R^4$ and $R^7$ is, independently, H, F, $C_{1-6}$ alkyl, or $C_{1-6}$ alkoxy;

$R^5$ is H, $R^{5A}C(NH)NH(CH_2)_{r5}$, or $R^{5B}NHC(S)NH(CH_2)_{r5}$, wherein r5 is an integer from 0 to 2, $R^{5A}$ is optionally substituted $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, optionally substituted aryloyl, or optionally substituted $C_{1-4}$ thioalkheterocyclyl; and $R^{5B}$ is optionally substituted $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, or optionally substituted aryloyl; and $R^6$ is H, F, $R^{6A}C(NH)NH(CH_2)_{r6}$, or $R^{6B}NHC(S)NH(CH_2)_{r6}$, wherein r6 is an integer from 0 to 2, $R^{6A}$ is optionally substituted $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, optionally substituted aryloyl, or optionally substituted $C_{1-4}$ thioalkheterocyclyl; and $R^{6B}$ is optionally substituted $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, or optionally substituted aryloyl.

In a preferred embodiment, $R^6$ is H.

In certain embodiments, $R^1$ is H, optionally substituted $C_{1-6}$ alkyl, optionally substituted $C_{1-4}$ alkaryl, or optionally substituted $C_{1-4}$ alkheterocyclyl. In preferred embodiments, $R^1$ is H.

The methods of the invention may treat visceral pain that is secondary to irritable bowel syndrome, inflammatory bowel syndrome, pancreatitis, diverticulitis, Crohn's disease, peritonitis, pericarditis, hepatitis, appendicitis, colitis, cholecystitis, gastroenteritis, endometriosis, dysmenorrhea, interstitial cystitis, prostatitis, pleuritis, upper gastrointestinal dyspepsia, renal colic, or biliary colic; visceral pain that is secondary to a disease of the liver, kidney, ovary, uterus, bladder, bowel, stomach, esophagus, duodenum, intestine, colon, spleen, pancreas, appendix, heart, or peritoneum; or visceral pain that results from a neoplasm or injury, or visceral pain that results from infection. Visceral pain treated by the methods of the invention may be inflammatory or non-inflammatory.

In certain embodiments, for the compounds employed $R^{5A}$ or $R^{6A}$ is methyl, fluoromethyl, ethyl, n-propyl, i-propyl, n-butyl, i-butyl, t-butyl, thiomethoxy, thioethoxy, thio-n-propyloxy, thio-i-propyloxy, thio-n-butyloxy, thio-i-butyloxy, thio-t-butyloxy, phenyl, benzyl, 2-thienyl, 3-thienyl, 2-furanyl, 3-furanyl, 2-oxazole, 4-oxazole, 5-oxazole, 2-thiazole, 4-thiazole, 5-thiazole, 2-isoxazole, 3-isoxazole, 4-isoxazole, 2-isothiazole, 3-isothiazole, and 4-isothiazole. In some embodiments, $R^1$, $R^2$, and $R^3$ are each H. In other embodiments, one or more of $R^1$, $R^2$, and $R^3$ is not H. For example, $R^1$ may be $(CH_2)_{m1}X^1$, wherein $X^1$ is selected from the group consisting of:

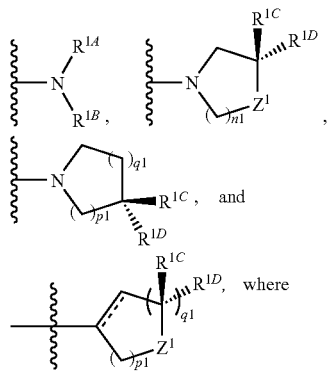

each of $R^{1A}$ and $R^{1B}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl;

each of $R^{1C}$ and $R^{1D}$ is, independently, H, F, OH, $CO_2R^{1E}$, or $NR^{1F}R^{1G}$, wherein each of $R^{1E}$, $R^{1F}$, and $R^{1G}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl, or $R^{1C}$ and $R^{1D}$ together with the carbon they are bonded to are C=O;

$Z^1$ is $NR^{1H}$, $NC(O)R^{1H}$, $NC(O)OR^{1H}$, $NC(O)NHR^{1H}$, $NC(S)R^{1H}$, $NC(S)NHR^{1H}$, $NS(O)_2R^{1H}$, O, S, S(O), or $S(O)_2$, wherein $R^{1H}$ is H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl;

m1 is an integer of 0 to 6;
n1 is an integer of 1 to 4;
p1 is an integer of 0 to 2; and
q1 is an integer of 0 to 5.

In some embodiments, where $X^1$ is

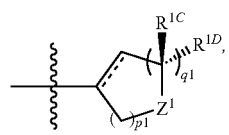

$X^1$ has a structure selected from

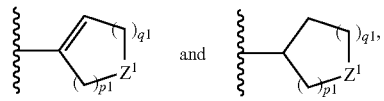

where $Z^1$, q1, and p1 are as defined herein.

$R^2$ may be $(CH_2)_m X^2$, wherein $X^2$ is selected from the group consisting of:

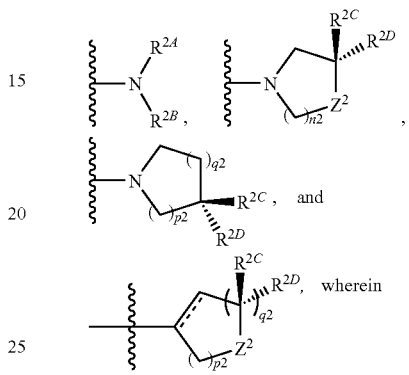

each of $R^{2A}$ and $R^{2B}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl;

each of $R^{2C}$ and $R^{2D}$ is, independently, H, F, OH, $CO_2R^{2E}$, or $NR^{2F}R^{2G}$, wherein each of $R^{2E}$, $R^{2F}$, and $R^{2G}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl, or $R^{2C}$ and $R^{2D}$ together with the carbon they are bonded to are C=O;

$Z^2$ is $NR^{2H}$, $NC(O)R^{2H}$, $NC(O)OR^{2H}$, $NC(O)NHR^{2H}$, $NC(S)R^{2H}$, $NC(S)NHR^{2H}$, $NS(O)_2R^{2H}$, O, S, S(O), or $S(O)_2$, wherein $R^{2H}$ is H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl;

m2 is an integer of 0 to 6;
n2 is an integer of 1 to 4;
p2 is an integer of 0 to 2; and
q2 is an integer of 0 to 5.

In some embodiments where $X^2$ is

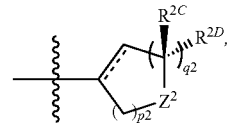

$X^2$ can have a structure selected from

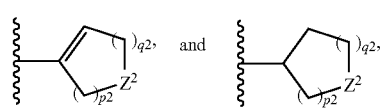

where $Z^2$, p2, and q2 are as defined herein.

$R^3$ may be $(CH_2)_m X^3$, wherein $X^3$ is selected from the group consisting of:

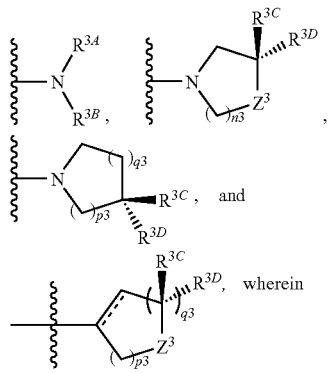

each of $R^{3A}$ and $R^{3B}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl;

each of $R^{3C}$ and $R^{3D}$ is, independently, H, F, OH, $CO_2 R^{3E}$, or $NR^{3F} R^{3G}$, wherein each of $R^{3E}$, $R^{3F}$, and $R^{3G}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl, or $R^{3C}$ and $R^{3D}$ together with the carbon they are bonded to are C=O;

$Z^3$ is $NR^{3H}$, $NC(O)R^{3H}$, $NC(O)OR^{3H}$, $NC(O)NHR^{3H}$, $NC(S)R^{3H}$, $NC(S)NHR^{3H}$, $NS(O)_2 R^{3H}$, O, S, S(O), or $S(O)_2$, wherein $R^{3H}$ is H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl;

m3 is an integer of 0 to 6;
n3 is an integer of 1 to 4;
p3 is an integer of 0 to 2; and
q3 is an integer of 0 to 5.

In some embodiments, where $R^3$ is

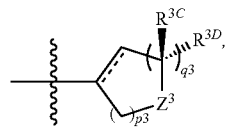

$R^3$ has a structure selected from

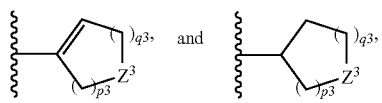

where $Z^3$, p3, and q3 are as defined herein.

In another embodiment of the invention, compounds of formula I wherein $R^5$ is $R^{5A}C(NH)NH(CH_2)_{r5}$ or $R^{5B}NHC(S)NH(CH_2)_{r5}$, $R^6$, $R^2$, and $R^1$ are H, and $R^3$ is $(CH_2)_{m3}X^3$ also bind to the serotonin 5HT1D/1B receptors. Preferably the $IC_{50}$ or $K_i$ value is between 10 and 0.001 micromolar. More preferably, the $IC_{50}$ or $K_i$ is less than 1 micromolar. Most preferably, the $IC_{50}$ or $K_i$ is less than 0.1. In other embodiments, compounds are agonists of the $5HT_{1B/1D}$ receptors.

In other embodiments, $R^2$ is

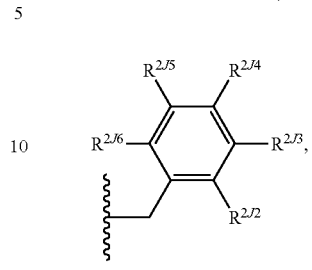

wherein each of $R^{2J2}$, $R^{2J3}$, $R^{2J4}$, $R^{2J5}$, and $R^{2J6}$ is, independently, H; $C_{1-6}$ alkyl; OH; $C_{1-6}$ alkoxy; SH; $C_{1-6}$ thioalkoxy; Halo; $NO_2$; CN; $CF_3$; $OCF_3$; $NR^{2Ja}R^{2Jb}$, where each of $R^{2Ja}$ and $R^{2Jb}$ is, independently, H or $C_{1-6}$ alkyl; $C(O)R^{2Jc}$, where $R^{2Jc}$ is H or $C_{1-6}$ alkyl; $CO_2 R^{2Jd}$, where $R^{2Jd}$ is H or $C_{1-6}$ alkyl; tetrazolyl; $C(O)NR^{2Je}R^{2Jf}$, where each of $R^{2Je}$ and $R^{2Jf}$ is, independently, H or $C_{1-6}$ alkyl; $OC(O)R^{2Jg}$, where $R^{2Jg}$ is $C_{1-6}$ alkyl; $NHC(O)R^{2Jh}$, where $R^{2Jh}$ is H or $C_{1-6}$ alkyl; $SO_3H$; $S(O)_2 NR^{2Ji}R^{2Jj}$, where each of $R^{2Ji}$ and $R^{2Jj}$ is, independently, H or $C_{1-6}$ alkyl; $S(O)R^{2Jk}$, where $R^{2Jk}$ is $C_{1-6}$ alkyl; and $S(O)_2 R^{2Jl}$, where $R^{2Jl}$ is $C_{1-6}$ alkyl.

Other compounds are those where $R^1$ or $R^3$ is

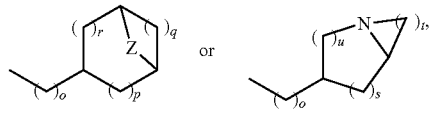

wherein Z is $NR^X$, o is an integer from 0-3, p is an integer from 1 to 2, q is an integer from 0 to 2, r is an integer from 0 to 1, s is an integer from 1 to 3, u is an integer from 0 to 1, and t is an integer from 3 to 7 (for example, from 5 to 7), wherein said $R^1$ or $R^3$ substituent includes 0 to 6 carbon-carbon double bonds or 0 or 1 carbon-nitrogen double bonds, and wherein $R^x$ is H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl.

Still other compounds have the formula:

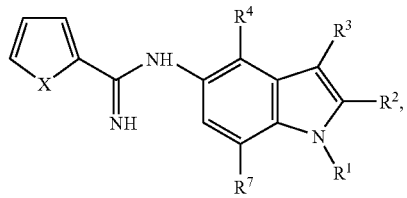

where X is O or S.

Compounds useful in the methods include 2-ethyl-1-(1H-indol-5-yl)-isothiourea; N-(1H-indol-5-yl)-thiophene-2-carboxamidine; N-[1-(2-dimethylamino-ethyl)-1H-indol-6-yl]-thiophene-2-carboxamidine; N-{1-[2-(1-methyl-pyrrolidin-2-yl)-ethyl]-1H-indol-6-yl}-thiophene-2-carboxamidine; 1-[1-(2-dimethylamino-ethyl)-1H-indol-6-yl]-2-ethyl-isothiourea; N-[1-(2-pyrrolidin-1-yl-ethyl)-1H-indol-6-yl]-thiophene-2-carboxamidine; N-(1-phenethyl-1H-indol-6-yl)-thiophene-2-carboxamidine; N-[3-(2-dimethylaminoethyl)-1H-indol-5-yl]-thiophene-2-carboxamidine; N-(1-{2-[2-(4-bromo-phenyl)-ethylamino]-ethyl}-1H-indol-6-yl)-thiophene-2-carboxamidine; (+)-N-{1-[2-(1-methyl-pyrrolidin-2-yl)-ethyl]-1H-indol-6-yl}-thiophene-2-carboxamidine; (−)-N-{1-[2-(1-methyl-pyrrolidin-2-yl)-ethyl]-1H-indol-6-yl}-thiophene-2-carboxamidine; N-[1-(1-methyl-azepan-4-yl)-1H-indol-6-yl]-thiophene-2-carboxamidine; and N-[1-(2-piperidin-1-yl-ethyl)-1H-indol-6-yl]-thiophene-2-carboxamidine.

Other exemplary compounds include:

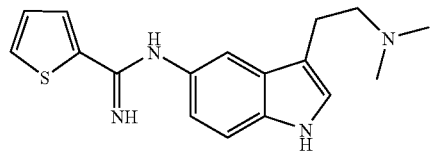

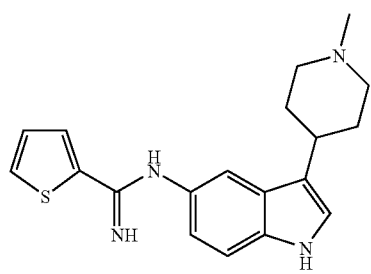

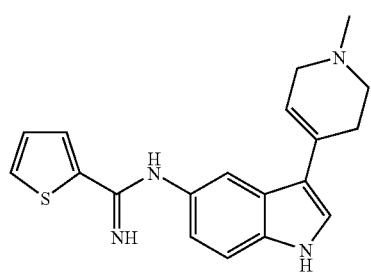

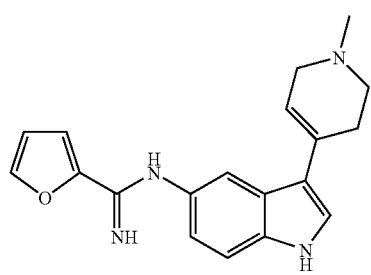

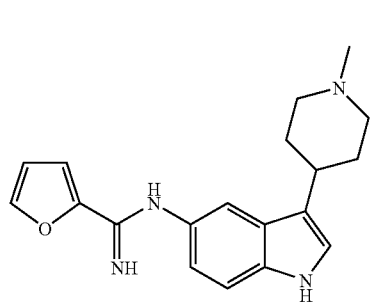

-continued

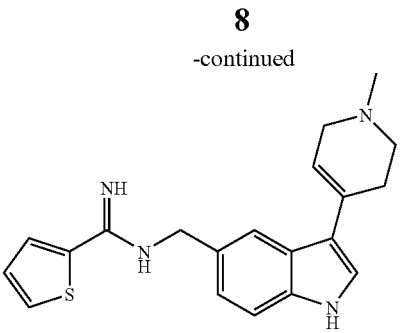

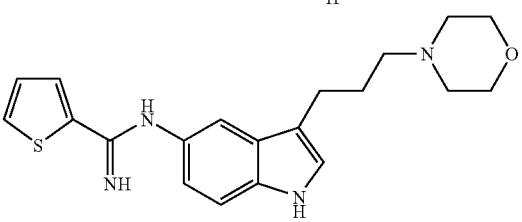

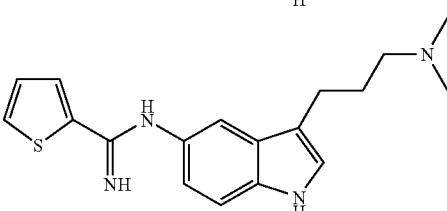

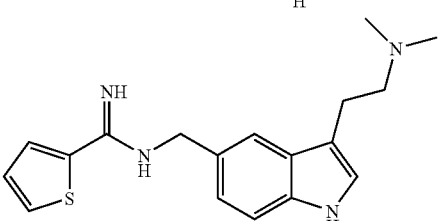

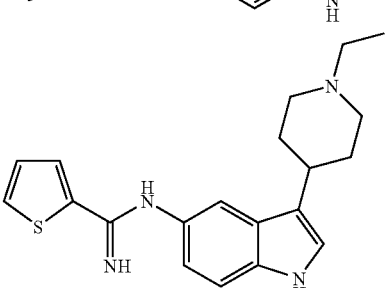

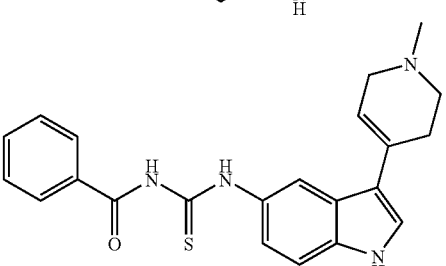

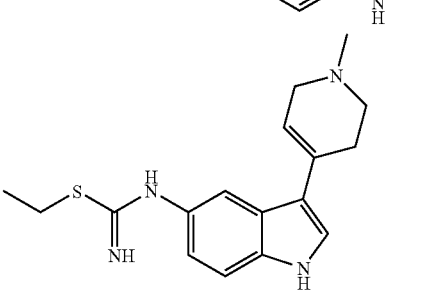

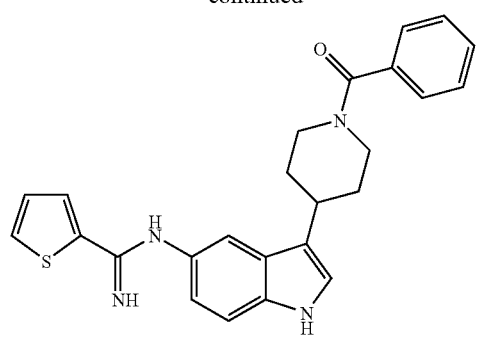
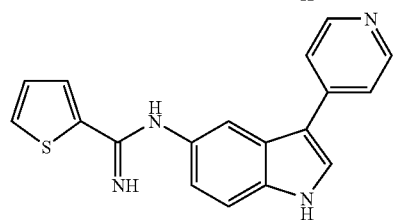
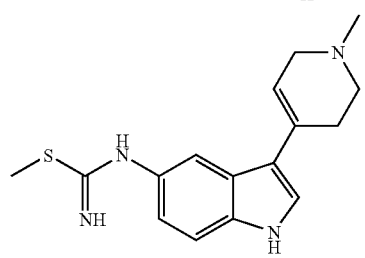
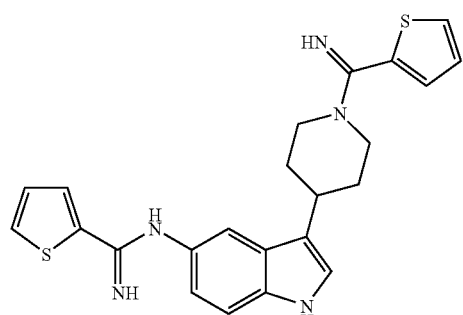
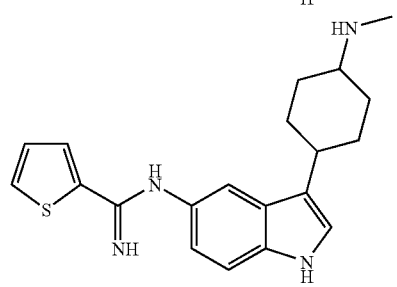
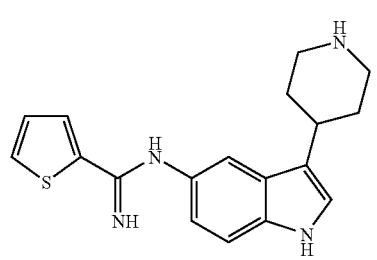
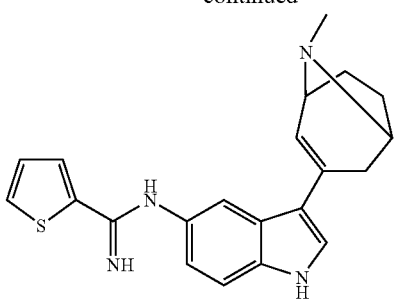
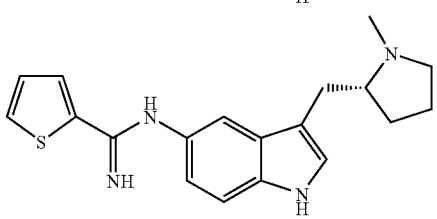
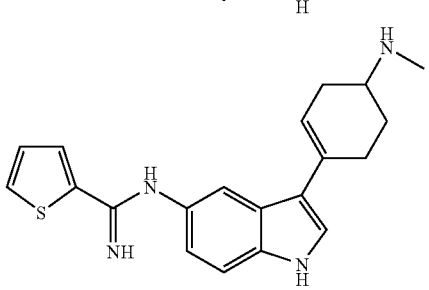
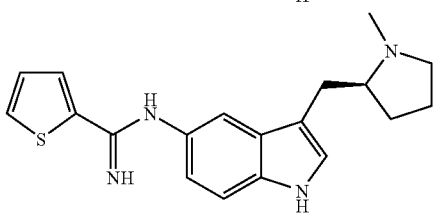
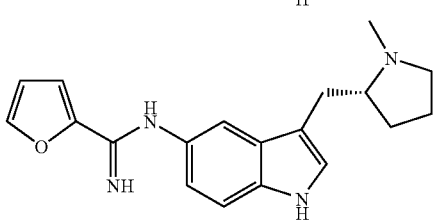
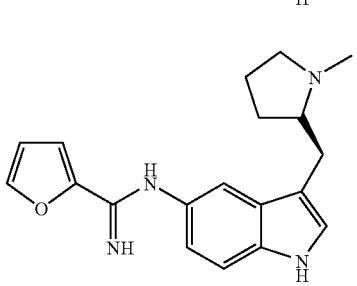
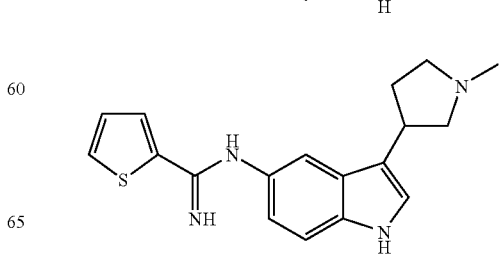

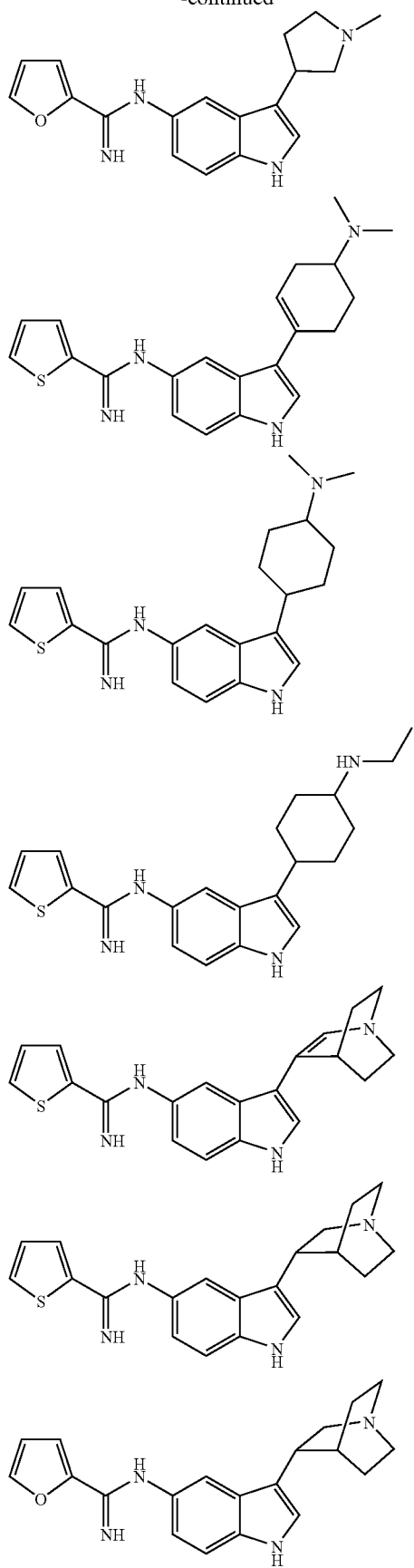
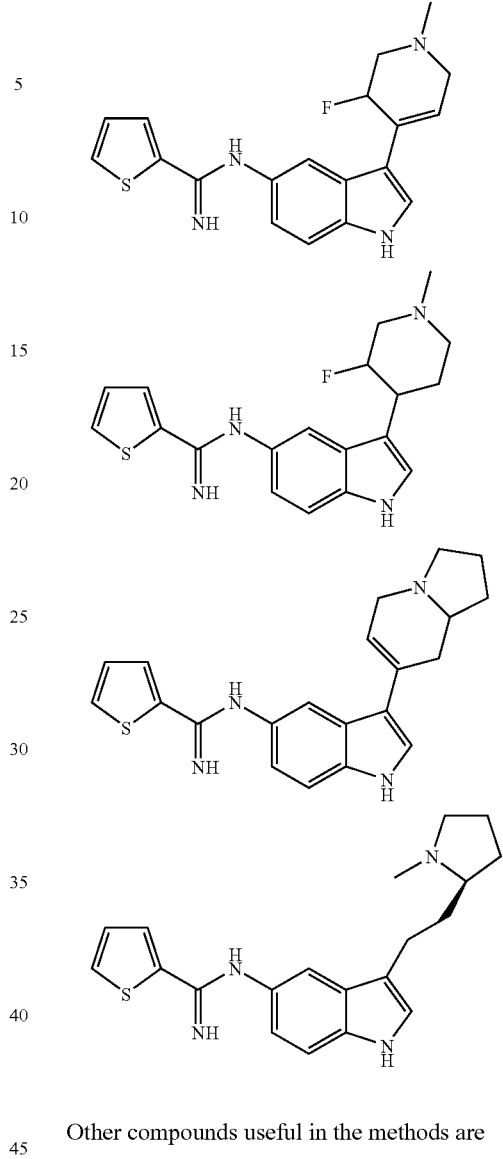
Other compounds useful in the methods are
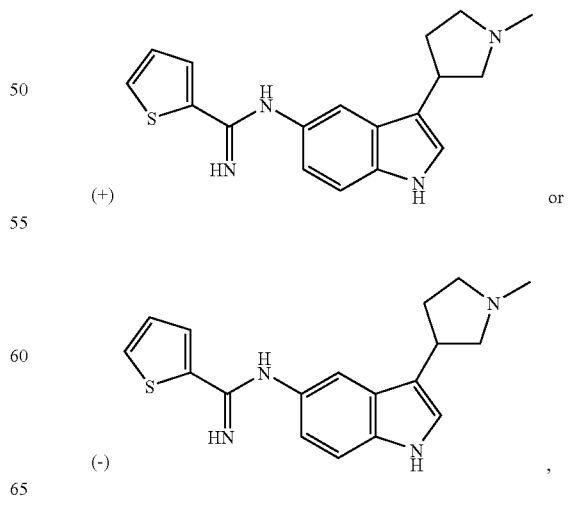
preferably the (+)-enantiomer.

Yet other compounds useful in the methods of the invention are

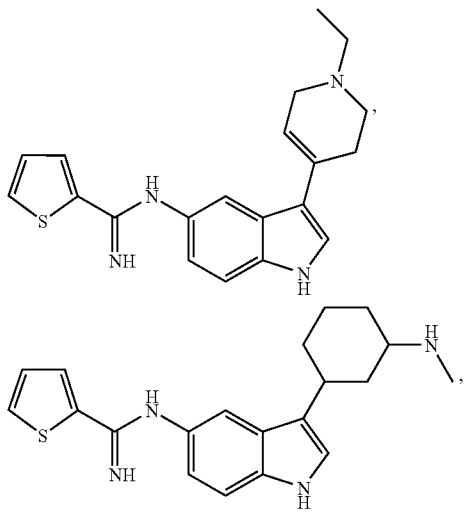

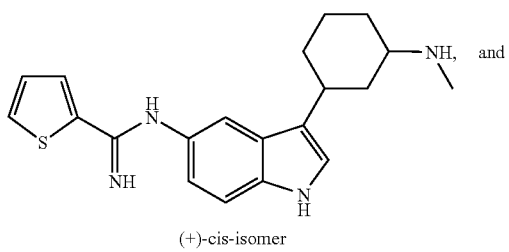

Mixture of cis-enantiomers

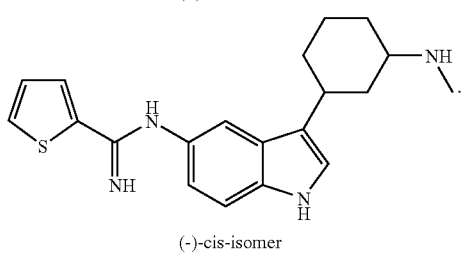

(+)-cis-isomer

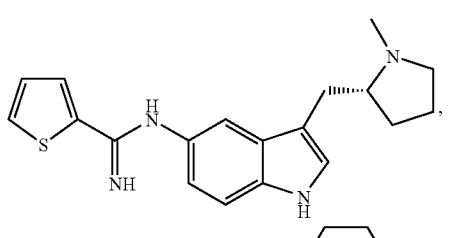

(-)-cis-isomer

Still other compounds useful in the methods of the invention are

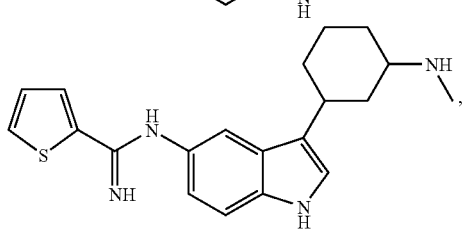

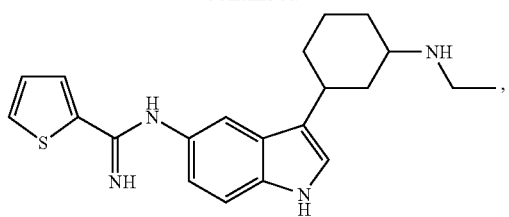

Mixture of trans-enantiomers

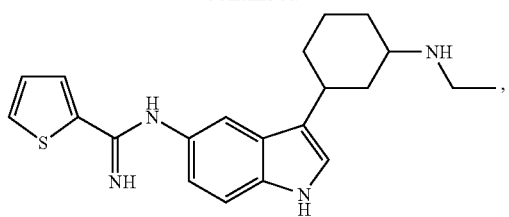

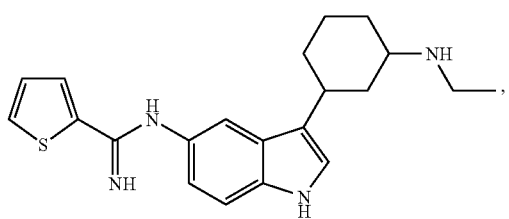

Mixture of trans-enantiomers

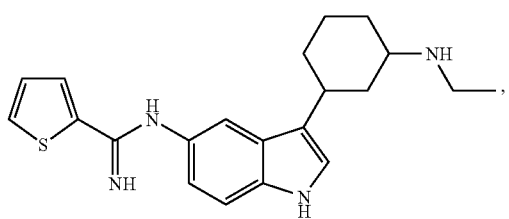

Mixture of cis-enantiomers

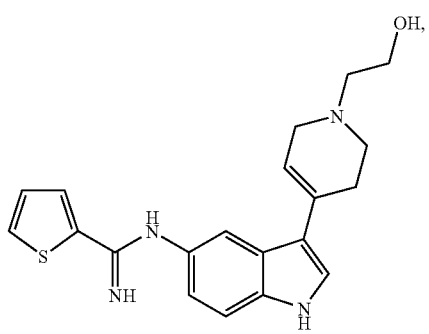

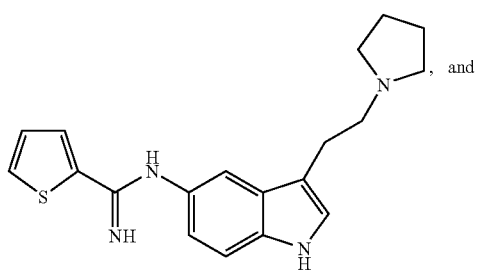

, and

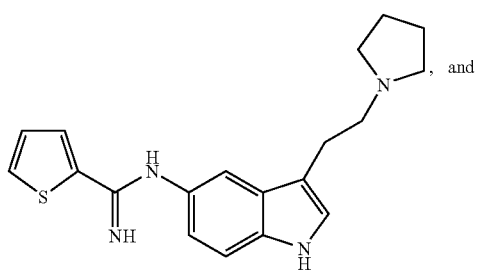

Mixture of four isomers

The method may further include administering a 5HT$_{1B}$ or 5HT$_{1D}$ receptor agonist, e.g., a triptan, such as sumatriptan, rizatriptan, naratriptan, zolmitriptan, eletriptan, almotriptan, or frovatriptan.

The methods may also include administering one or more agents selected from the group consisting of analgesics, antidepressants, and anticonvulsants.

The invention further features the compounds

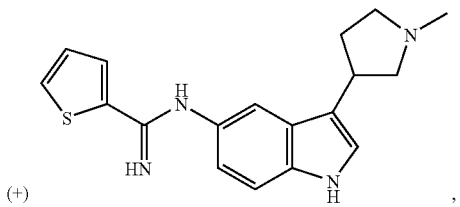 [SMILES: CN1CCC(c2c[nH]c3ccc(NC(=N)c4cccs4)cc23)C1]

(+)

or a pharmaceutically acceptable salt thereof; and

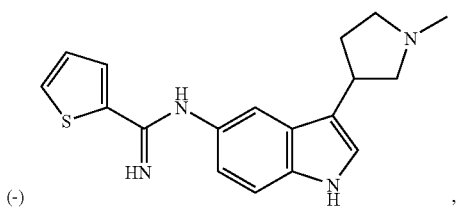 [SMILES: CN1CCC(c2c[nH]c3ccc(NC(=N)c4cccs4)cc23)C1]

(−)

or a pharmaceutically acceptable salt thereof.

The invention yet further features the compound

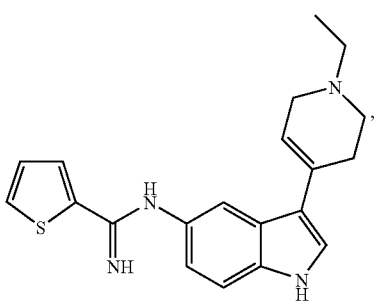 [SMILES: CCN1CC=C(c2c[nH]c3ccc(NC(=N)c4cccs4)cc23)CC1]

or a pharmaceutically acceptable salt thereof, or

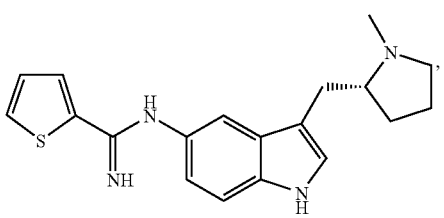 [SMILES: CN1CCC[C@@H]1Cc1c[nH]c2ccc(NC(=N)c3cccs3)cc12]

or a pharmaceutically acceptable salt thereof.

The invention further features pharmaceutical compositions of any of the above compounds in combination with a pharmaceutically acceptable carrier.

The invention also features the mixture of compounds:

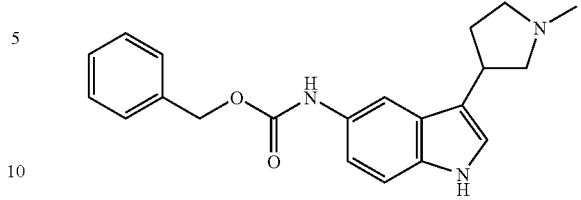

or a salt thereof, and the individual (+) or (−) enantiomers thereof.

The invention also features a method of synthesizing an enantiomer, e.g., (+) or (−) of

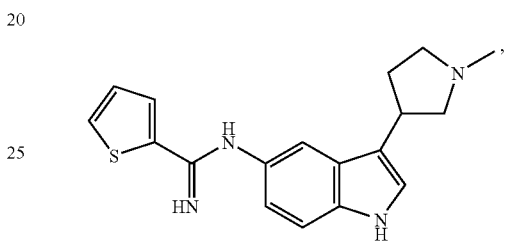

by a. reacting 3-(1-methylpyrrolidin-3-yl)-1H-indol-5-amine with benzyl chloroformate to form (±) benzyl 3-(1-methylpyrrolidin-3-yl)-1H-indol-5-ylcarbamate;

b. subjecting (±) benzyl 3-(1-methylpyrrolidin-3-yl)-1H-indol-5-ylcarbamate to chiral HPLC or SFC (supercritical fluid chromatography) to resolve the enantiomers of benzyl 3-(1-methylpyrrolidin-3-yl)-1H-indol-5-ylcarbamate;

c. deprotecting one enantiomer of benzyl 3-(1-methylpyrrolidin-3-yl)-1H-indol-5-ylcarbamate by hydrogenation to yield one enantiomer 3-(1-methylpyrrolidin-3-yl)-1H-indol-5-amine; and d. reacting one enantiomer of 3-(1-methylpyrrolidin-3-yl)-1H-indol-5-amine with methyl thiophene-2-carbimidothioate.

In yet another aspect, the invention features a method of treating a condition in a mammal, such as, for example, a human, caused by the action of nitric oxide synthase (NOS), and particularly nNOS, that includes administering an effective amount of a compound of the formula

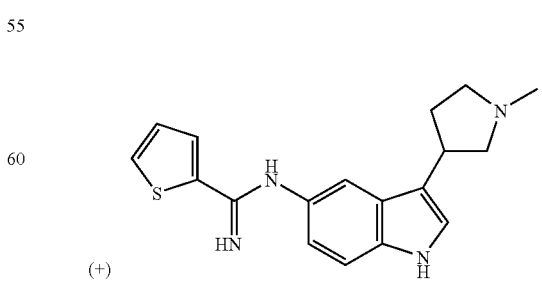

(+)

or a pharmaceutically acceptable salt thereof;

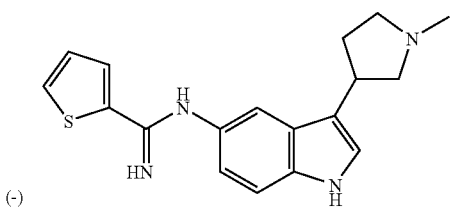 [SMILES: CN1CCC(c2c[nH]c3ccc(NC(=N)c4cccs4)cc23)C1]

or a pharmaceutically acceptable salt thereof, or

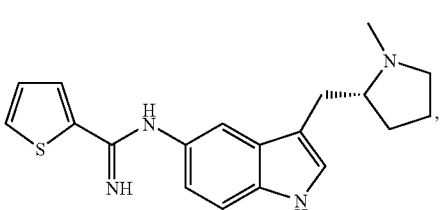

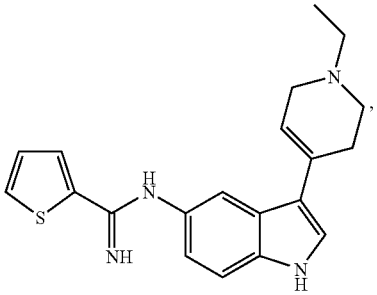

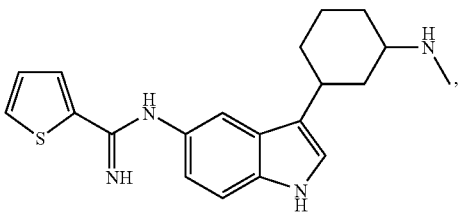

Mixture of cis-enantiomers

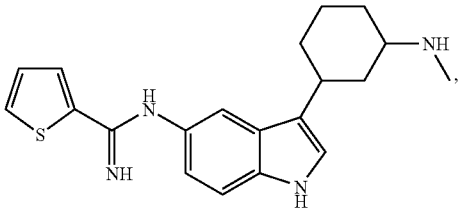

(+)-cis-isomer

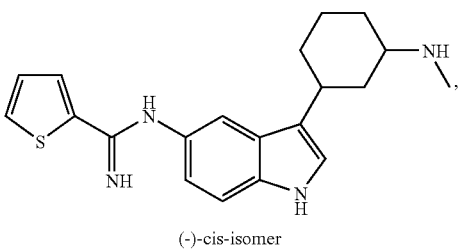

(−)-cis-isomer

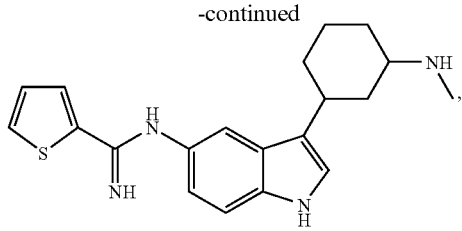

Mixture of trans-enantiomers

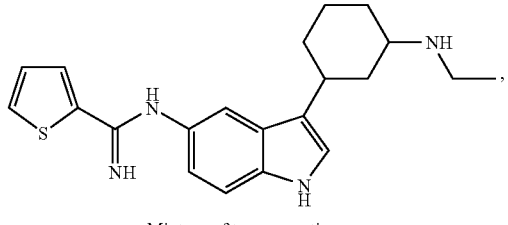

Mixture of trans-enantiomers

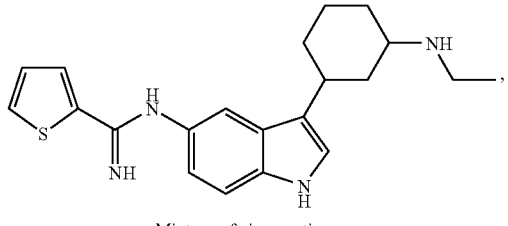

Mixture of cis-enantiomers

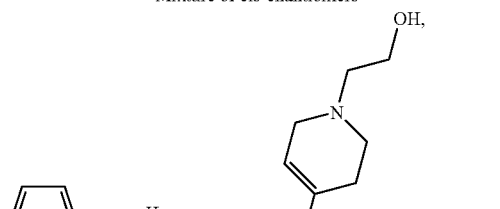

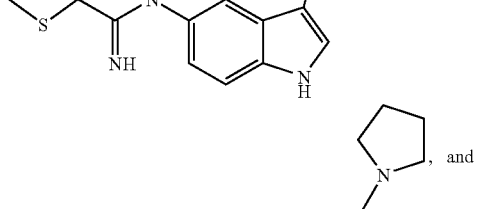

, and

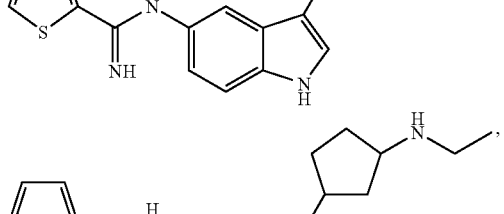

Mixture of four isomers or a pharmaceutically acceptable salt thereof, to the mammal.

Examples of conditions that can be prevented or treated include migraine headache (with or without aura), chronic tension type headache (CTTH), migraine with allodynia, neuropathic pain, post-stroke pain, chronic headache, chronic pain, acute spinal cord injury, diabetic neuropathy, trigeminal neuralgia, diabetic nephropathy, an inflammatory disease, stroke, reperfusion injury, head trauma, cardiogenic shock, CABG associated neurological damage, HCA, AIDS associated dementia, neurotoxicity, Parkinson's disease, Alzheimer's disease, ALS, Huntington's disease, multiple sclerosis, methamphetamine-induced neurotoxicity, drug addiction, morphine/opioid induced tolerance, dependence, hyperalgesia, or withdrawal, ethanol tolerance, dependence, or withdrawal, epilepsy, anxiety, depression, attention deficit hyperactivity disorder, and psychosis. Compounds of the invention are particularly useful for treating stroke, reperfusion injury, neurodegeneration, head trauma, CABG associated neurological damage, migraine headache (with or without aura), migraine with allodynia, chronic tension type headache, neuropathic pain, post-stroke pain, opioid induced hyperalgesia, or chronic pain. In particular, 3,5-substituted indole compounds are useful for treating migraine, with or without aura, and CTTH.

These compounds of the invention can also be used in combination with one or more other therapeutic agents for the prevention or treatment of one of the aforementioned conditions. Examples of classes of therapeutic agents and some specific examples that are useful in combination with a compound of the invention are listed in Table 1.

Other agents useful in combination with these compounds, include antiarrhythmics; DHP-sensitive L-type calcium channel antagonists; omega-conotoxin (Ziconotide)-sensitive N-type calcium channel antagonists; P/Q-type calcium channel antagonists; adenosine kinase antagonists; adenosine receptor $A_1$ agonists; adenosine receptor $A_{2a}$ antagonists; adenosine receptor $A_3$ agonists; adenosine deaminase inhibitors; adenosine nucleoside transport inhibitors; vanilloid VR1 receptor agonists; Substance P/$NK_1$ antagonists; cannabinoid CB1/CB2 agonists; GABA-B antagonists; AMPA and kainate antagonists, metabotropic glutamate receptor antagonists; alpha-2-adrenergic receptor agonists; nicotinic acetylcholine receptor agonists (nAChRs); cholecystokinin B antagonists; sodium channel blockers; a $K_{ATP}$ potassium channel, $K_{v1.4}$ potassium channel, $Ca^{2+}$-activated potassium channel, SK potassium channel, BK potassium channel, IK potassium channel, or KCNQ2/3 potassium channel opening agent (eg. retigabine); $5HT_{1A}$ agonists; muscarinic M3 antagonists, M1 agonists, M2/M3 partial agonist/antagonists; and antioxidants.

TABLE 1

Therapeutic agents useful in combination with compounds of the invention

| Class | Examples |
|---|---|
| Opioid | alfentanil, butorphanol, buprenorphine, codeine, dextromoramide, dextropropoxyphene, dezocine, dihydrocodeine, diphenoxylate, etorphine, fentanyl, hydrocodone, hydromorphone, ketobemidone, levorphanol, levomethadone, methadone, meptazinol, morphine, morphine-6-glucuronide, nalbuphine, naloxone, oxycodone, oxymorphone, pentazocine, pethidine, piritramide, remifentanil, sulfentanyl, tilidine, or tramadol |
| Antidepressant (selective serotonin re-uptake inhibitor) | citalopram, escitalopram, fluoxetine, fluvoxamine, paroxetine, or sertraline |
| Antidepressant (norepinephrine-reuptake inhibitor) | clomipramine, doxepin, imipramine, imipramine oxide, trimipramine; adinazolam, amiltriptylinoxide, amoxapine, desipramine, maprotiline, nortriptyline, protriptyline, amineptine, butriptyline, demexiptiline, dibenzepin, dimetacrine, dothiepin, fluacizine, iprindole, lofepramine, melitracen, metapramine, norclolipramine, noxiptilin, opipramol, perlapine, pizotyline, propizepine, quinupramine, reboxetine, atomoxetine, bupropion, reboxetine, or tianeptine |
| Antidepressant (dual serotonin/norepinephrine reuptake inhibitor) | duloxetine, milnacipran, mirtazapine, nefazodone, or venlafaxine |
| Antidepressant (monoamine oxidase inhibitor) | amiflamine, iproniazid, isocarboxazid, M-3-PPC (Draxis), moclobemide, pargyline, phenelzine, tranylcypromine, or vanoxerine |
| Antidepressant (reversible monoamine oxidase type A inhibitor) | bazinaprine, befloxatone, brofaromine, cimoxatone, or clorgyline |
| Antidepressant (tricyclic) | amitriptyline, clomipramine, desipramine, doxepin, imipramine, maprotiline, nortryptyline, protriptyline, or trimipramine |
| Antidepressant (other) | adinazolam, alaproclate, amineptine, amitriptyline/chlordiazepoxide combination, atipamezole, azamianserin, bazinaprine, befuraline, bifemelane, binodaline, bipenamol, brofaromine, caroxazone, cericlamine, cianopramine, cimoxatone, citalopram, clemeprol, clovoxamine, dazepinil, deanol, demexiptiline, dibenzepin, dothiepin, droxidopa, enefexine, estazolam, etoperidone, femoxetine, fengabine, fezolamine, fluotracen, idazoxan, indalpine, indeloxazine, iprindole, levoprotiline, lithium, litoxetine; lofepramine, medifoxamine, metapramine, metralindole, mianserin, milnacipran, minaprine, mirtazapine, montirelin, nebracetam, nefopam, nialamide, nomifensine, norfluoxetine, orotirelin, oxaflozane, pinazepam, pirlindone, pizotyline, ritanserin, rolipram, sercloremine, setiptiline, sibutramine, sulbutiamine, sulpiride, teniloxazine, thozalinone, thymoliberin, tianeptine, tiflucarbine, trazodone, tofenacin, |

TABLE 1-continued

Therapeutic agents useful in combination with compounds of the invention

| Class | Examples |
|---|---|
| | tofisopam, toloxatone, tomoxetine, veralipride, viloxazine, viqualine, zimelidine, or zometapine |
| Antiepileptic | carbamazepine, flupirtine, gabapentin, lamotrigine, oxcarbazepine, phenytoin, retigabine, topiramate, or valproate |
| Non-steroidal anti-inflammatory drug (NSAID) | acemetacin, aspirin, celecoxib, deracoxib, diclofenac, diflunisal, ethenzamide, etofenamate, etoricoxib, fenoprofen, flufenamic acid, flurbiprofen, lonazolac, lornoxicam, ibuprofen, indomethacin, isoxicam, kebuzone, ketoprofen, ketorolac, naproxen, nabumetone, niflumic acid, piroxicam, meclofenamic acid, mefenamic acid, meloxicam, metamizol, mofebutazone, oxyphenbutazone, parecoxib, phenidine, phenylbutazone, piroxicam, propacetamol, propyphenazone, rofecoxib, salicylamide, sulindac, suprofen, tiaprofenic acid, tenoxicam, tolmetin, valdecoxib, 4-(4-cyclohexyl-2-methyloxazol-5-yl)-2-fluorobenzenesulfonamide, N-[2-(cyclohexyloxy)-4-nitrophenyl]methanesulfonamide, 2-(3,4-difluorophenyl)-4-(3-hydroxy-3-methylbutoxy)-5-[4-(methylsulfonyl)phenyl]-3(2H)-pyridazinone, or 2-(3,5-difluorophenyl)-3-[4-(methylsulfonyl)phenyl]-2-cyclopenten-1-one) |
| $5HT_{1B/1D}$ agonist | almotriptan, eletriptan, frovatriptan, naratriptan, rizatriptan, sumatriptan, or zolmitriptan |
| Anti-inflammatory compounds | aspirin, celecoxib, cortisone, deracoxib, diflunisal, etoricoxib, fenoprofen, ibuprofen, ketoprofen, naproxen, prednisolone, sulindac, tolmetin, piroxicam, mefenamic acid, meloxicam, phenylbutazone, rofecoxib, suprofen, valdecoxib, 4-(4-cyclohexyl-2-methyloxazol-5-yl)-2-fluorobenzenesulfonamide, N-[2-(cyclohexyloxy)-4-nitrophenyl]methanesulfonamide, 2-(3,4-difluorophenyl)-4-(3-hydroxy-3-methylbutoxy)-5-[4-(methylsulfonyl)phenyl]-3(2H)-pyridazinone, or 2-(3,5-difluorophenyl)-3-[4-(methylsulfonyl)phenyl]-2-cyclopenten-1-one |
| N-methyl-D-aspartate antagonist | amantadine; aptiganel; besonprodil; budipine; conantokin G; delucemine; dexanabinol; dextromethorphan; dextropropoxyphen; felbamate; fluorofelbamate; gacyclidine; glycine; ipenoxazone; kaitocephalin; ketamine; ketobemidone; lanicemine; licostinel; midafotel; memantine; D-methadone; D-morphine; milnacipran; neramexane; orphenadrine; remacemide; sulfazocine; FPL-12,495 (racemide metabolite); topiramate; ($\alpha$R)-$\alpha$-amino-5-chloro-1-(phosphonomethyl)-1H-benzimidazole-2-propanoic acid; 1-aminocyclopentane-carboxylic acid; [5-(aminomethyl)-2-[[[(5S)-9-chloro-2,3,6,7-tetrahydro-2,3-dioxo-1H-,5H-pyrido[1,2,3-de]quinoxalin-5-yl]acetyl]amino]phenoxy]-acetic acid; $\alpha$-amino-2-(2-phosphonoethyl)-cyclohexanepropanoic acid; $\alpha$-amino-4-(phosphonomethyl)-benzeneacetic acid; (3E)-2-amino-4-(phosphonomethyl)-3-heptenoic acid; 3-[(1E)-2-carboxy-2-phenylethenyl]-4,6-dichloro-1H-indole-2-carboxylic acid; 8-chloro-2,3-dihydropyridazino[4,5-b]quinoline-1,4-dione 5-oxide salt with 2-hydroxy-N,N,N-trimethyl-ethanaminium; N'-[2-chloro-5-(methylthio)phenyl]-N-methyl-N-[3-(methylthio)phenyl]-guanidine; N'-[2-chloro-5-(methylthio)phenyl]-N-methyl-N-[3-[(R)-methylsulfinyl]phenyl]-guanidine; 6-chloro-2,3,4,9-tetrahydro-9-methyl-2,3-dioxo-1H-indeno[1,2-b]pyrazine-9-acetic acid; 7-chlorothiokynurenic acid; (3S,4aR,6S,8aR)-decahydro-6-(phosphonomethyl)-3-isoquinolinecarboxylic acid; (−)-6,7-dichloro-1,4-dihydro-5-[3-(methoxymethyl)-5-(3-pyridinyl)-4-H-1,2,4-triazol-4-yl]-2,3-quinoxalinedione; 4,6-dichloro-3-[(E)-(2-oxo-1-phenyl-3-pyrrolidinylidene)methyl]-1H-indole-2-carboxylic acid; (2R,4S)-rel-5,7-dichloro-1,2,3,4-tetrahydro-4-[[(phenylamino)carbonyl]amino]-2-quinolinecarboxylic acid; (3R,4S)-rel-3,4-dihydro-3-[4-hydroxy-4-(phenylmethyl)-1-piperidinyl-]-2H-1-benzopyran-4,7-diol; 2-[(2,3-dihydro-1H-inden-2-yl)amino]-acetamide; 1,4-dihydro-6-methyl-5-[(methylamino)methyl]-7-nitro-2,3-quinoxalinedione; [2-(8,9-dioxo-2,6-diazabicyclo[5.2.0]non-1(7)-en-2-yl)ethyl]-phosphonic acid; (2R,6S)-1,2,3,4,5,6-hexahydro-3-[(2S)-2-methoxypropyl]-6,11,11-trimethyl-2,6-methano-3-benzazocin-9-ol; 2-hydroxy-5-[[(pentafluorophenyl)methyl]amino]-benzoic acid; 1-[2-(4-hydroxyphenoxy)ethyl]-4-[(4-methylphenyl)methyl]-4-piperidinol; 1-[4-(1H-imidazol-4-yl)-3-butynyl]-4-(phenylmethyl)-piperidine; 2-methyl-6-(phenylethynyl)-pyridine; 3-(phosphonomethyl)-L-phenylalanine; or 3,6,7-tetrahydro-2,3-dioxo-N-phenyl-1H,5H-pyrido[1,2,3-de]quinoxaline-5-acetamide |

Asymmetric or chiral centers may exist in any of the compounds of the present invention. The present invention contemplates the various stereoisomers and mixtures thereof. These stereochemical mixtures can be resolved using methods exemplified by (1) attachment of a racemic mixture of enantiomers, designated (+/−), to a chiral auxiliary, separation of the resulting diastereomers by recrystallization or chromatography and liberation of the optically pure product from the auxiliary or (2) direct separation of the mixture of optical enantiomers on chiral chromatographic columns. Enantiomers are designated herein by the symbols "R," or "S," depending on the configuration of substituents around the chiral carbon atom. Alternatively, enantiomers are designated as (+) or (−) depending on whether a solution of the enantiomer rotates the plane of polarized light clockwise or counterclockwise, respectively.

Geometric isomers may also exist in the compounds of the present invention. The present invention contemplates the various geometric isomers and mixtures thereof resulting from the arrangement of substituents around a carbon-carbon double bond and designates such isomers as of the Z or E configuration, where the term "Z" represents substituents on the same side of the carbon-carbon double bond and the term "E" represents substituents on opposite sides of the carbon-carbon double bond. It is also recognized that for structures in which tautomeric forms are possible, the description of one tautomeric form is equivalent to the description of both, unless otherwise specified. For example, amidine structures of the formula —C(=$NR^Q$)$NHR^T$ and —C($NHR^Q$)=$NR^T$, where $R^T$ and $R^Q$ are different, are equivalent tautomeric structures and the description of one inherently includes the other.

It is understood that substituents and substitution patterns on the compounds of the invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

Other features and advantages will be apparent from the following description and the claims.

Definitions

The terms "acyl" or "alkanoyl," as used interchangeably herein, represent an alkyl group, as defined herein, or hydrogen attached to the parent molecular group through a carbonyl group, as defined herein, and is exemplified by formyl, acetyl, propionyl, butanoyl and the like. Exemplary unsubstituted acyl groups include from 2 to 7 carbons.

The terms "$C_{x-y}$ alkaryl" or "$C_{x-y}$ alkylenearyl," as used herein, represent a chemical substituent of formula —RR', where R is an alkylene group of x to y carbons and R' is an aryl group as defined elsewhere herein. Similarly, by the terms "$C_{x-y}$ alkheteroaryl" or "$C_{x-y}$ alkyleneheteroaryl," is meant a chemical substituent of formula —RR", where R is an alkylene group of x to y carbons and R" is a heteroaryl group as defined elsewhere herein. Other groups preceded by the prefix "alk-" or "alkylene-" are defined in the same manner. Exemplary unsubstituted alkaryl groups are of from 7 to 16 carbons.

The term "alkcycloalkyl" represents a cycloalkyl group attached to the parent molecular group through an alkylene group.

The term "alkenyl," as used herein, represents monovalent straight or branched chain groups of, unless otherwise specified, from 2 to 6 carbons containing one or more carbon-carbon double bonds and is exemplified by ethenyl, 1-propenyl, 2-propenyl, 2-methyl-1-propenyl, 1-butenyl, 2-butenyl, and the like.

The term "alkheterocyclyl" represents a heterocyclic group attached to the parent molecular group through an alkylene group. Exemplary unsubstituted alkheterocyclyl groups are of from 3 to 14 carbons.

The term "alkoxy" represents a chemical substituent of formula —OR, where R is an alkyl group of 1 to 6 carbons, unless otherwise specified.

The term "alkoxyalkyl" represents an alkyl group which is substituted with an alkoxy group. Exemplary unsubstituted alkoxyalkyl groups include between 2 to 12 carbons.

The terms "alkyl" and the prefix "alk-," as used herein, are inclusive of both straight chain and branched chain saturated groups of from 1 to 6 carbons, unless otherwise specified. Alkyl groups are exemplified by methyl, ethyl, n- and isopropyl, n-, sec-, iso- and tert-butyl, neopentyl, and the like, and may be optionally substituted with one, two, three or, in the case of alkyl groups of two carbons or more, four substituents independently selected from the group consisting of: (1) alkoxy of one to six carbon atoms; (2) alkylsulfinyl of one to six carbon atoms; (3) alkylsulfonyl of one to six carbon atoms; (4) amino; (5) aryl; (6) arylalkoxy; (7) aryloyl; (8) azido; (9) carboxaldehyde; (10) cycloalkyl of three to eight carbon atoms; (11) halo; (12) heterocyclyl; (13) (heterocycle)oxy; (14) (heterocycle)oyl; (15) hydroxyl; (16) N-protected amino; (17) nitro; (18) oxo; (19) spiroalkyl of three to eight carbon atoms; (20) thioalkoxy of one to six carbon atoms; (21) thiol; (22) —$CO_2R^A$, where $R^A$ is selected from the group consisting of (a) alkyl, (b) aryl and (c) alkaryl, where the alkylene group is of one to six carbon atoms; (23) —C(O)$NR^BR^C$, where each of $R^B$ and $R^C$ is, independently, selected from the group consisting of (a) hydrogen, (b) alkyl, (c) aryl and (d) alkaryl, where the alkylene group is of one to six carbon atoms; (24) —$SO_2R^D$, where $R^D$ is selected from the group consisting of (a) alkyl, (b) aryl and (c) alkaryl, where the alkylene group is of one to six carbon atoms; (25) —$SO_2NR^ER^F$, where each of $R^E$ and $R^F$ is, independently, selected from the group consisting of (a) hydrogen, (b) alkyl, (c) aryl and (d) alkaryl, where the alkylene group is of one to six carbon atoms; and (26) —$NR^GR^H$, where each of $R^G$ and $R^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, with the proviso that no two groups are bound to the nitrogen atom through a carbonyl group or a sulfonyl group.

The term "alkylene," as used herein, represents a saturated divalent hydrocarbon group derived from a straight or branched chain saturated hydrocarbon by the removal of two hydrogen atoms, and is exemplified by methylene, ethylene, isopropylene, and the like.

The term "alkylsulfinyl," as used herein, represents an alkyl group attached to the parent molecular group through an —S(O)— group. Exemplary unsubstituted alkylsulfinyl groups are of from 1 to 6 carbons.

The term "alkylsulfonyl," as used herein, represents an alkyl group attached to the parent molecular group through an —$SO_2$— group. Exemplary unsubstituted alkylsulfonyl groups are of from 1 to 6 carbons.

The term "alkylsulfinylalkyl," as used herein, represents an alkyl group, as defined herein, substituted by an alkylsulfinyl group. Exemplary unsubstituted alkylsulfinylalkyl groups are of from 2 to 12 carbons.

The term "alkylsulfonylalkyl," as used herein, represents an alkyl group, as defined herein, substituted by an alkylsulfonyl group. Exemplary unsubstituted alkylsulfonylalkyl groups are of from 2 to 12 carbons.

The term "alkynyl," as used herein, represents monovalent straight or branched chain groups of from two to six carbon atoms containing a carbon-carbon triple bond and is exemplified by ethynyl, 1-propynyl, and the like.

The term "amidine," as used herein, represents a —C(=NH)NH$_2$ group.

The term "amino," as used herein, represents an —NH$_2$ group.

The term "aminoalkyl," as used herein, represents an alkyl group, as defined herein, substituted by an amino group.

The term "aryl," as used herein, represents a mono- or bicyclic carbocyclic ring system having one or two aromatic rings and is exemplified by phenyl, naphthyl, 1,2-dihydronaphthyl, 1,2,3,4-tetrahydronaphthyl, fluorenyl, indanyl, indenyl, and the like, and may be optionally substituted with one, two, three, four, or five substituents independently selected from the group consisting of: (1) alkanoyl of one to six carbon atoms; (2) alkyl of one to six carbon atoms; (3) alkoxy of one to six carbon atoms; (4) alkoxyalkyl, where the alkyl and alkylene groups are independently of one to six carbon atoms; (5) alkylsulfinyl of one to six carbon atoms; (6) alkylsulfinylalkyl, where the alkyl and alkylene groups are independently of one to six carbon atoms; (7) alkylsulfonyl of one to six carbon atoms; (8) alkylsulfonylalkyl, where the alkyl and alkylene groups are independently of one to six carbon atoms; (9) aryl; (10) amino; (11) aminoalkyl of one to six carbon atoms; (12) heteroaryl; (13) alkaryl, where the alkylene group is of one to six carbon atoms; (14) aryloyl; (15) azido; (16) azidoalkyl of one to six carbon atoms; (17) carboxaldehyde; (18) (carboxaldehyde)alkyl, where the alkylene group is of one to six carbon atoms; (19) cycloalkyl of three to eight carbon atoms; (20) alkcycloalkyl, where the cycloalkyl group is of three to eight carbon atoms and the alkylene group is of one to ten carbon atoms; (21) halo; (22) haloalkyl of one to six carbon atoms; (23) heterocyclyl; (24) (heterocyclyl)oxy; (25) (heterocyclyl)oyl; (26) hydroxy; (27) hydroxyalkyl of one to six carbon atoms; (28) nitro; (29) nitroalkyl of one to six carbon atoms; (30) N-protected amino; (31) N-protected aminoalkyl, where the alkylene group is of one to six carbon atoms; (32) oxo; (33) thioalkoxy of one to six carbon atoms; (34) thioalkoxyalkyl, where the alkyl and alkylene groups are independently of one to six carbon atoms; (35) —(CH$_2$)$_q$CO$_2$R$^A$, where q is an integer of from zero to four, and R$^A$ is selected from the group consisting of (a) alkyl, (b) aryl, and (c) alkaryl, where the alkylene group is of one to six carbon atoms; (36) —(CH$_2$)$_q$CONR$^B$R$^C$, where q is an integer of from zero to four and where R$^B$ and R$^C$ are independently selected from the group consisting of (a) hydrogen, (b) alkyl, (c) aryl, and (d) alkaryl, where the alkylene group is of one to six carbon atoms; (37) —(CH$_2$)$_q$SO$_2$R$^D$, where q is an integer of from zero to four and where R$^D$ is selected from the group consisting of (a) alkyl, (b) aryl, and (c) alkaryl, where the alkylene group is of one to six carbon atoms; (38) —(CH$_2$)$_q$SO$_2$NR$^E$R$^F$, where q is an integer of from zero to four and where each of R$^E$ and R$^F$ is, independently, selected from the group consisting of (a) hydrogen, (b) alkyl, (c) aryl, and (d) alkaryl, where the alkylene group is of one to six carbon atoms; (39) —(CH$_2$)$_q$NR$^G$R$^H$, where q is an integer of from zero to four and where each of R$^G$ and R$^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, with the proviso that no two groups are bound to the nitrogen atom through a carbonyl group or a sulfonyl group; (40) thiol; (41) perfluoroalkyl; (42) perfluoroalkoxy; (43) aryloxy; (44) cycloalkoxy; (45) cycloalkylalkoxy; and (46) arylalkoxy.

The term "arylalkoxy," as used herein, represents an alkaryl group attached to the parent molecular group through an oxygen atom. Exemplary unsubstituted arylalkoxy groups are of from 7 to 16 carbons.

The term "aryloxy" represents a chemical substituent of formula —OR', where R' is an aryl group of 6 to 18 carbons, unless otherwise specified.

The terms "aryloyl" and "aroyl" as used interchangeably herein, represent an aryl group that is attached to the parent molecular group through a carbonyl group. Exemplary unsubstituted aryloyl groups are of 7 or 11 carbons.

The term "azido" represents an N$_3$ group, which can also be represented as N=N=N.

The term "azidoalkyl" represents an azido group attached to the parent molecular group through an alkyl group.

The term "bridged heterocyclyl" represents a heterocyclic compound, as otherwise described herein, having a bridged multicyclic structure in which one or more carbon atoms and/or heteroatoms bridges two non-adjacent members of a monocyclic ring. An exemplary bridged heterocyclyl group is a quinuclidinyl group.

The term "bridged alkheterocyclyl" represents a bridged heterocyclic compound, as otherwise described herein, attached to the parent molecular group through an alkylene group.

The term "carbonyl," as used herein, represents a C(O) group, which can also be represented as C=O.

The term "carboxaldehyde" represents a CHO group.

The term "carboxaldehydealkyl" represents a carboxaldehyde group attached to the parent molecular group through an alkylene group.

The term "cycloalkyl," as used herein represents a monovalent saturated or unsaturated non-aromatic cyclic hydrocarbon group of from three to eight carbons, unless otherwise specified, and is exemplified by cyclopropyl, cyclobutyl, cyclopentyl, cyclohexyl, cycloheptyl, bicyclo[2.2.1.]heptyl and the like. The cycloalkyl groups of this invention can be optionally substituted with (1) alkanoyl of one to six carbon atoms; (2) alkyl of one to six carbon atoms; (3) alkoxy of one to six carbon atoms; (4) alkoxyalkyl, where the alkyl and alkylene groups are independently of one to six carbon atoms; (5) alkylsulfinyl of one to six carbon atoms; (6) alkylsulfinylalkyl, where the alkyl and alkylene groups are independently of one to six carbon atoms; (7) alkylsulfonyl of one to six carbon atoms; (8) alkylsulfonylalkyl, where the alkyl and alkylene groups are independently of one to six carbon atoms; (9) aryl; (10) amino; (11) aminoalkyl of one to six carbon atoms; (12) heteroaryl; (13) alkaryl, where the alkylene group is of one to six carbon atoms; (14) aryloyl; (15) azido; (16) azidoalkyl of one to six carbon atoms; (17) carboxaldehyde; (18) (carboxaldehyde)alkyl, where the alkylene group is of one to six carbon atoms; (19) cycloalkyl of three to eight carbon atoms; (20) alkcycloalkyl, where the cycloalkyl group is of three to eight carbon atoms and the alkylene group is of one to ten carbon atoms; (21) halo; (22) haloalkyl of one to six carbon atoms; (23) heterocyclyl; (24) (heterocyclyl)oxy; (25) (heterocyclyl)oyl; (26) hydroxy; (27) hydroxyalkyl of one to six carbon atoms; (28) nitro; (29) nitroalkyl of one to six carbon atoms; (30) N-protected amino; (31) N-protected aminoalkyl, where the alkylene group is of one to six carbon atoms; (32) oxo; (33) thioalkoxy of one to six carbon atoms; (34) thioalkoxyalkyl, where the alkyl and alkylene groups are independently of one to six carbon atoms; (35) —(CH$_2$)$_q$CO$_2$R$^A$, where q is an integer of from zero to four, and R$^A$ is selected from the group consisting of (a) alkyl, (b) aryl, and (c) alkaryl, where the alkylene group is of one to six carbon atoms; (36) —(CH$_2$)$_q$CONR$^B$R$^C$, where q is an integer of from zero to four and where R$^B$ and R$^C$ are independently selected from the group consisting of (a) hydrogen, (b) alkyl, (c) aryl, and (d) alkaryl, where the alkylene group is of one to six carbon atoms; (37) —(CH$_2$)$_q$SO$_2$R$^D$, where q is an integer of from zero to four and where R$^D$ is selected from the group consisting of (a) alkyl, (b) aryl, and (c) alkaryl, where the alkylene group is of one to six carbon atoms; (38) —(CH$_2$)$_q$SO$_2$NR$^E$R$^F$, where q is an integer of from zero to four and where each of R$^E$ and R$^F$ is, independently, selected from the group consisting of (a) hydrogen, (b) alkyl, (c) aryl, and (d) alkaryl, where the alkylene group is of one to six carbon atoms; (39) —(CH$_2$)$_q$NR$^G$R$^H$, where q is an integer of from zero to four and where each of R$^G$ and R$^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, with the proviso that no two groups are bound to the nitrogen atom through a carbonyl group or a sulfonyl group; (40) thiol; (41) perfluoroalkyl; (42) perfluoroalkoxy; (43) aryloxy; (44) cycloalkoxy; (45) cycloalkylalkoxy; and (46) arylalkoxy.

The terms "cycloalkyloxy" or "cycloalkoxy", as used interchangeably herein, represent a cycloalkyl group, as defined herein, attached to the parent molecular group through an oxygen atom. Exemplary unsubstituted cycloalkyloxy groups are of from 3 to 8 carbons.

The term an "effective amount" or a "sufficient amount" of an agent, as used herein, is that amount sufficient to effect beneficial or desired results, such as clinical results, and, as such, an "effective amount" depends upon the context in which it is being applied. For example, in the context of administering an agent that is an inhibitor of NOS, an effective amount of an agent is, for example, an amount sufficient to achieve a reduction in NOS activity as compared to the response obtained without administration of the agent.

The terms "halide" or "halogen" or "Hal" or "halo," as used herein, represent bromine, chlorine, iodine, or fluorine.

The term "haloalkyl," as used herein, represents an alkyl group, as defined herein, substituted by a halo group.

The term "heteroaryl," as used herein, represents that subset of heterocycles, as defined herein, which are aromatic: i.e., they contain 4n+2 pi electrons within the mono- or multicyclic ring system.

The terms "heterocycle" or "heterocyclyl," as used interchangeably herein represent a 5-, 6- or 7-membered ring, unless otherwise specified, containing one, two, three, or four heteroatoms independently selected from the group consisting of nitrogen, oxygen and sulfur. The 5-membered ring has zero to two double bonds and the 6- and 7-membered rings have zero to three double bonds. The term "heterocycle" also includes bicyclic, tricyclic and tetracyclic groups in which any of the above heterocyclic rings is fused to one, two, or three rings independently selected from the group consisting of an aryl ring, a cyclohexane ring, a cyclohexene ring, a cyclopentane ring, a cyclopentene ring and another monocyclic heterocyclic ring, such as indolyl, quinolyl, isoquinolyl, tetrahydroquinolyl, benzofuryl, benzothienyl and the like. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidiniyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazoyl, triazolyl, tetrazolyl, oxadiazolyl, uricyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl and the like. Heterocyclic groups also include compounds of the formula

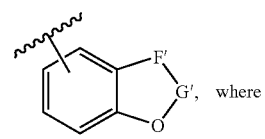, where

F' is selected from the group consisting of —CH$_2$—, —CH$_2$O— and —O—, and G' is selected from the group consisting of —C(O)— and —(C(R')(R''))$_v$—, where each of R' and R'' is, independently, selected from the group consisting of hydrogen or alkyl of one to four carbon atoms, and v is one to three and includes groups, such as 1,3-benzodioxolyl, 1,4-benzodioxanyl, and the like. Any of the heterocycle groups mentioned herein may be optionally substituted with one, two, three, four or five substituents independently selected from the group consisting of: (1) alkanoyl of one to six carbon atoms; (2) alkyl of one to six carbon atoms; (3) alkoxy of one to six carbon atoms; (4) alkoxyalkyl, where the alkyl and alkylene groups are independently of one to six carbon atoms; (5) alkylsulfinyl of one to six carbon atoms; (6) alkylsulfinylalkyl, where the alkyl and alkylene groups are independently of one to six carbon atoms; (7) alkylsulfonyl of one to six carbon atoms; (8) alkylsulfonylalkyl, where the alkyl and alkylene groups are independently of one to six carbon atoms; (9) aryl; (10) amino; (11) aminoalkyl of one to six carbon atoms; (12) heteroaryl; (13) alkaryl, where the alkylene group is of one to six carbon atoms; (14) aryloyl; (15) azido; (16) azidoalkyl of one to six carbon atoms; (17) carboxaldehyde; (18) (carboxaldehyde)alkyl, where the alkylene group is of one to six carbon atoms; (19) cycloalkyl of three to eight carbon atoms; (20) alkcycloalkyl, where the cycloalkyl group is of three to eight carbon atoms and the alkylene group is of one to ten carbon atoms; (21) halo; (22) haloalkyl of one to six carbon atoms; (23) heterocyclyl; (24) (heterocyclyl)oxy; (25) (heterocyclyl)oyl; (26) hydroxy; (27) hydroxyalkyl of one to six carbon atoms; (28) nitro; (29) nitroalkyl of one to six carbon atoms; (30) N-protected amino; (31) N-protected aminoalkyl, where the alkylene group is of one to six carbon atoms; (32) oxo; (33) thioalkoxy of one to six carbon atoms; (34) thioalkoxyalkyl, where the alkyl and alkylene groups are independently of one to six carbon atoms; (35) —(CH$_2$)$_q$CO$_2$R$^A$, where q is an integer of from zero to four, and R$^A$ is selected from the group consisting of (a) alkyl, (b) aryl, and (c) alkaryl, where the alkylene group is of one to six carbon atoms; (36) —(CH$_2$)$_q$CONR$^B$R$^C$, where q is an integer of from zero to four and where R$^B$ and R$^C$ are independently selected from the group consisting of (a) hydrogen, (b) alkyl, (c) aryl, and (d) alkaryl, where the alkylene group is of one to six carbon atoms; (37) —(CH$_2$)$_q$SO$_2$R$^D$, where q is an integer of from zero to four and where R$^D$ is selected from the group consisting of (a)

alkyl, (b) aryl, and (c) alkaryl, where the alkylene group is of one to six carbon atoms; (38) —$(CH_2)_q SO_2 NR^E R^F$, where q is an integer of from zero to four and where each of $R^E$ and $R^F$ is, independently, selected from the group consisting of (a) hydrogen, (b) alkyl, (c) aryl, and (d) alkaryl, where the alkylene group is of one to six carbon atoms; (39) —$(CH_2)_q NR^G R^H$, where q is an integer of from zero to four and where each of $R^G$ and $R^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, with the proviso that no two groups are bound to the nitrogen atom through a carbonyl group or a sulfonyl group; (40) thiol; (41) perfluoroalkyl; (42) perfluoroalkoxy; (43) aryloxy; (44) cycloalkoxy; (45) cycloalkylalkoxy; and (46) arylalkoxy.

The terms "heterocyclyloxy" and "(heterocycle)oxy," as used interchangeably herein, represent a heterocycle group, as defined herein, attached to the parent molecular group through an oxygen atom.

The terms "heterocyclyloyl" and "(heterocycle)oyl," as used interchangeably herein, represent a heterocycle group, as defined herein, attached to the parent molecular group through a carbonyl group.

The term "hydroxy" or "hydroxyl," as used herein, represents an —OH group.

The term "hydroxyalkyl," as used herein, represents an alkyl group, as defined herein, substituted by one to three hydroxy groups, with the proviso that no more than one hydroxy group may be attached to a single carbon atom of the alkyl group and is exemplified by hydroxymethyl, dihydroxypropyl, and the like.

The terms "inhibit" or "suppress" or "reduce," as relates to a function or activity, such as NOS activity, means to reduce the function or activity when compared to otherwise same conditions except for a condition or parameter of interest, or alternatively, as compared to another condition.

The term "N-protected amino," as used herein, refers to an amino group, as defined herein, to which is attached an N-protecting or nitrogen-protecting group, as defined herein.

The term "N-protected aminoalkyl," as used herein, represents an alkyl group, as defined herein, substituted by an amino group to which is attached an N-protecting or nitrogen-protecting group, as defined herein.

The terms "N-protecting group" and "nitrogen protecting group," as used herein, represent those groups intended to protect an amino group against undesirable reactions during synthetic procedures. Commonly used N-protecting groups are disclosed in Greene, "Protective Groups In Organic Synthesis," $3^{rd}$ Edition (John Wiley & Sons, New York, 1999), which is incorporated herein by reference. N-protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, phenylalanine, and the like; sulfonyl groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, arylalkyl groups such as benzyl, triphenylmethyl, benzyloxymethyl, and the like and silyl groups such as trimethylsilyl, and the like. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —$NO_2$ group.

The term "nitroalkyl," as used herein, represents an alkyl group, as defined herein, substituted by a nitro group.

The term "oxo" or (O) as used herein, represents =O.

The term "perfluoroalkyl," as used herein, represents an alkyl group, as defined herein, where each hydrogen radical bound to the alkyl group has been replaced by a fluoride radical. Perfluoroalkyl groups are exemplified by trifluoromethyl, pentafluoroethyl, and the like.

The term "perfluoroalkoxy," as used herein, represents an alkoxy group, as defined herein, where each hydrogen radical bound to the alkoxy group has been replaced by a fluoride radical.

The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, S. M Berge et al. describe pharmaceutically acceptable salts in detail in *J. Pharmaceutical Sciences* 66:1-19, 1977. The salts can be prepared in situ during the final isolation and purification of the compounds of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The term "pharmaceutically acceptable prodrugs" as used herein, represents those prodrugs of the compounds of the present invention which are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "Ph" as used herein means phenyl.

The term "prodrug," as used herein, represents compounds which are rapidly transformed in vivo to the parent compound of the above formula, for example, by hydrolysis in blood. Prodrugs of the compounds of the invention may be conventional esters. Some common esters which have been utilized as prodrugs include, but are not limited to, phenyl esters, aliphatic ($C_8$-$C_{24}$) esters, acyloxymethyl esters, carbamates, and amino acid esters. For example, a compound of the invention that contains an OH group may be acylated at this position in its prodrug form. A thorough discussion is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and Judkins et al., *Synthetic Communications* 26(23):4351-4367, 1996, each of which is incorporated herein by reference.

Each of the terms "selectively inhibits nNOS" or "a selective nNOS inhibitor" refers to a substance, such as, for example, a compound of the invention, that inhibits or binds the nNOS isoform more effectively than the eNOS and/or iNOS isoform by an in vitro assay, such as, for example, those assays described herein. Selective inhibition can be expressed in terms of an $IC_{50}$ value, a $K_i$ value, or the inverse of a percent inhibition value which is lower when the substance is tested in an nNOS assay than when tested in an eNOS and/or iNOS assay. Preferably, the $IC_{50}$ or $K_i$ value is 2 times lower. More preferably, the $IC_{50}$ or $K_i$ value is 5 times lower. Most preferably, the $IC_{50}$ or $K_i$ value is 10, or even 50 times lower.

The term "prophylaxis" refers to preventive or pre-emptive treatment for an event expected to result in a condition, for example, visceral pain, and encompasses procedures designed to target individuals at risk of suffering from a condition, such as visceral pain.

The term "solvate" as used herein means a compound of the invention wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate."

The term "spiroalkyl," as used herein, represents an alkylene diradical, both ends of which are bonded to the same carbon atom of the parent group to form a spirocyclic group.

The term "sulfonyl," as used herein, represents an —$S(O)_2$— group.

The term "thioalkaryl," as used herein, represents a thioalkoxy group substituted with an aryl group.

The term "thioalkheterocyclyl," as used herein, represents a thioalkoxy group substituted with a heterocyclyl group.

The term "thioalkoxy," as used herein, represents an alkyl group attached to the parent molecular group through a sulfur atom. Exemplary unsubstituted alkylthio groups are of from 1 to 6 carbons.

The term "thioalkoxyalkyl" represents an alkyl group which is substituted with a thioalkoxy group. Exemplary unsubstituted thioalkoxyalkyl groups include between 2 to 12 carbons.

The term "thiol" represents an —SH group.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Treatment" can also mean prolonging survival as compared to expected survival if not receiving treatment. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

By "visceral pain" is meant any pain felt by a subject secondary to a disease, disorder, or condition of an internal organ. Conditions that result in visceral pain include, but are not limited to, irritable bowel syndrome, inflammatory bowel syndrome, pancreatitis, diverticulitis, Crohn's disease, peritonitis, pericarditis, hepatitis, appendicitis, colitis, cholecystitis, gastroenteritis, renal pain, interstitial cystitis, ovarian (e.g., cysts), endometriosis, dysmenorrhea, uterine pain, pain resulting from a cancer of a visceral organ, pain from injury, infection in an internal organ, gynecological pain, bladder pain, bowel pain, stomach pain, esophageal pain, referred cardiac pain, upper gastrointestinal dyspepsia, and colic (including renal and biliary colic). Visceral pain can be experienced by an animal with a disease or condition of an internal organ.

As used herein, by a "$5HT_{1B}$ agonist" and "$5HT_{1D}$ agonist" are meant, respectively, an agent that enhances the activity of 5-hydroxytryptamine/serotonin receptors 1B and/or 1D, e.g., by directly binding and activating $5HT_{1B}$ or $5HT_{1D}$ receptors (e.g., as with a triptan) or by inhibiting reuptake of serotonin (e.g., as with an SSRI). Agonists of $5HT_{1B/1D}$ receptors include, but are not limited to, antidepressants or antianxiety drugs (e.g., citalopram), amphetamines (e.g., dextroamphetamine and levoamphetamine), antiemetics or anxiolytics (e.g., benzodiazepines), anticonvulsants (e.g., sodium valproate), and triptans (e.g., sumatriptan). An agonist of $5HT_{1B}$ receptors may also agonize $5HT_{1D}$ receptors; conversely, an agonist of $5HT_{1D}$ receptors may also agonize $5HT_{1B}$ receptors.

By "analgesic" is meant any member of the diverse group of drugs used to relieve pain. Analgesic drugs act in various ways on the peripheral and central nervous systems. They include, but are not limited to, paracetamol (i.e., acetaminophen), the nonsteroidal anti-inflammatory drugs (NSAIDs), and opiate drugs such as morphine.

By "antidepressant" is meant any member of the diverse group of drugs used to relieve depression or dysthymia. Classes of antidepressants include selective serotonin reuptake inhibitors (SSRIs), serotonin-norepinephrine reuptake inhibitors (SNRIs), noradrenergic and specific serotonergic antidepressants (NASSAs), norepinephrine (noradrenaline) reuptake inhibitors (NRIs), norepinephrine-dopamine reuptake inhibitors (NDRIs), tricyclic antidepressants (TCAs), and monoamine oxidase inhibitors (MAOIs). Examples of antidepressant agents include, but are not limited to, amitriptyline, citalopram, desipramine, duloxetine, escitalopram, fluoxetine, fluvoxamine, paroxetine, sertraline, amitriptyline, desmethylamitriptyline, clomipramine, doxepin, imipramine, imipramine oxide, trimipramine; adinazolam, amil-triptylinoxide, amoxapine, desipramine, maprotiline, nortriptyline, protriptyline, amineptine, butriptyline, demexiptiline, dibenzepin, dimetacrine, dothiepin, fluacizin, iprindole, lofepramine, melitracen, metapramine, norclolipramine, noxiptilin, opipramol, perlapine, pizotyline, propizepine, quinupramine, reboxetine, atomoxetine, bupropion, reboxetine, tomoxetine, duloxetine, milnacipran, mirtazapine, nefazodone, venlafaxine, amiflamine, iproniazid, isocarboxazid, M-3-PPC (Draxis), moclobemide, pargyline, phenelzine, tranylcypromine, vanoxerine, bazinaprine, befloxatone, brofaromine, cimoxatone, clorgyline, amitriptyline, clomipramine, desipramine, doxepin, imipramine, maprotiline, nortryptyline, protriptyline, trimipramine, adinazolam, alaproclate, amineptine, amitriptyline/chlordiazepoxide combination, atipamezole, azamianserin, bazinaprine, befuraline, bifemelane, binodaline, bipenamol, brofaromine, caroxazone, cericlamine, cianopramine, cimoxatone; citalopram, clemeprol, clovoxamine, dazepinil, deanol, demexiptiline, dibenzepin, dothiepin, droxidopa, enefexine, estazolam, etoperidone, femoxetine, fengabine, fezolamine, fluotracen, idazoxan, indalpine, indeloxazine, iprindole, levoprotiline, lithium, litoxetine; lofepramine, medifoxamine, metapramine, metralindole, mianserin, milnacipran, minaprine, mirtazapine, montirelin, nebracetam, nefopam, nialamide, nomifensine, norfluoxetine, orotirelin, oxaflozane, pinazepam, pirlindone, pizotyline, ritanserin, rolipram, sercloremine, setiptiline, sibutramine, sulbutiamine, sulpiride, teniloxazine, thozalinone, thymoliberin, tianeptine, tiflucarbine, trazodone, tofenacin, tofisopam, toloxatone, tomoxetine, veralipride, viloxazine, viqualine, zimelidine, and zometapine.

By "anticonvulsive" is meant any of a diverse group of agents used in prevention of the occurrence of epileptic seizures (i.e., antiepileptic). The goal of an anticonvulsant is to suppress the rapid and excessive firing of neurons that start a seizure. Many anticonvulsants block sodium ($Na^+$) channels, calcium ($Ca^{2+}$) channels, AMPA receptors, or NMDA receptors. Some anticonvulsants inhibit the metabolism of GABA or increase its release. Examples of anticonvulsants include, but are not limited to, carbamazepine, flupirtine, gabapentin, lamotrigine, oxcarbazepine, phenyloin, retigabine, topiramate, and valproate.

By "cyclooxygenase-2 (COX-2) inhibitor" is meant any agent that inhibits the activity of the COX-2 enzyme. Examples of COX-2 inhibitors include, but are not limited to NSAIDS, paracetamol (i.e., acetaminophen), celecoxib, etoricoxib. lumiracoxib, parecoxib, rofecoxib, and valdecoxib.

By "non-steroidal anti-inflammatory drug" (NSAID) is meant an agent that exhibits analgesic, anti-inflammatory, and antipyretic effects on a treated subject. Examples of NSAIDS include, but are not limited to, aspirin, amoxiprin, benorilate, choline magnesium salicylate, faislamine, methyl salicylate, magnesium salicylate, salicyl salicylate (salsalate), aceclofenac, bromfenac, etodolac, sulindac, carprofen, fenbufen, loxoprofen, oxaprozin, azapropazone, sulfinpyrazone, nimesulide, licofelone acemetacin, celecoxib, deracoxib, diclofenac, diflunisal, ethenzamide, etofenamate, etoricoxib, fenoprofen, flufenamic acid, flurbiprofen, lonazolac, lomoxicam, ibuprofen, indomethacin, isoxicam, kebuzone, ketoprofen, ketorolac, naproxen, nabumetone, niflumic acid, sulindac, tolmetin, piroxicam, meclofenamic acid, mefenamic acid, meloxicam, metamizol, mofebutazone, oxyphenbutazone, parecoxib, phenidine, phenylbutazone, piroxicam, propacetamol, propyphenazone, rofecoxib, salicylamide, suprofen, tiaprofenic acid, tenoxicam, valdecoxib, 4-(4-cyclohexyl-2-methyloxazol-5-yl)-2-fluorobenzenesulfonamide, N-[2-(cyclohexyloxy)-4-nitrophenyl]methanesulfonamide, 2-(3,4-difluorophenyl)-4-(3-hydroxy-3-methylbutoxy)-5-[4-(methylsulfonyl)phenyl]-3(2H)-pyridazinone, and 2-(3,5-difluorophenyl)-3-[4-(methylsulfonyl)phenyl]-2-cyclopenten-1-one).

By "opiate" is meant any agent, natural or synthetic, that exerts an analgesic effect upon binding to an opioid receptor in the central nervous system. Examples of opiates include, but are not limited to, alfentanil, butorphanol, buprenorphine, codeine, dextromoramide, dextropropoxyphene, dezocine, dihydrocodeine, diphenoxylate, etorphine, fentanyl, hydrocodone, hydromorphone, ketobemidone, levorphanol, levomethadone, methadone, meptazinol, morphine, morphine-6-glucuronide, nalbuphine, naloxone, oxycodone, oxymorphone, pentazocine, pethidine, piritramide, remifentanil, sulfentanyl, tapentadol, tilidine, and tramadol.

BRIEF DESCRIPTION OF DRAWINGS

FIG. 1 shows the metabolic stability of compounds 6a and 6b incubated in the presence of human liver microsomes.

FIG. 2 shows the metabolic stability of compound 18 incubated in the presence of human liver micromes.

FIG. 3 shows the reversal of thermal hyperalgesia after i.p. administration of compound 6b in the Chung Model of nerve injury-induced neuropathic-like pain.

FIG. 4 shows the effect on the reversal of thermal hyperalgesia after i.p. administration of compound 6a in the Chung Model of nerve injury-induced neuropathic-like pain.

FIG. 5 and FIG. 6 show, respectively, a reversal of tactile hyperthesia following the i.p. administration of compound 6b but not 6a to test animals.

FIG. 7 shows the general testing protocol for a pancreatitis visceral pain model.

FIG. 8 shows the effects of compound 18 in a pancreatitis visceral pain model

FIG. 9 shows the effects of compound 6b in a pancreatitis visceral pain model.

FIG. 10 shows the effects of compound 18 in an IBS visceral pain model.

FIG. 11 shows the effects of compound 6a in a pancreatitis visceral pain model.

FIG. 12 shows the effects of compound 27 in a pancreatitis visceral pain model.

DETAILED DESCRIPTION OF THE INVENTION

We have discovered that certain indole compounds, such as 3,5-substituted indole compounds, are useful in treating visceral pain. Visceral pain may be caused by disease or injury to an internal organ, which refers pain to other parts of the body. Exemplary forms of visceral pain treated by the methods described herein include that secondary to irritable bowel syndrome, inflammatory bowel syndrome, pancreatitis, diverticulitis, Crohn's disease, peritonitis, pericarditis, hepatitis, appendicitis, colitis, cholecystitis, gastroenteritis, endometriosis, dysmenorrhea, interstitial cystitis, prostatitis, pleuritis, upper gastrointestinal dyspepsia, renal colic, or biliary colic. Other forms are described herein, and still others are known in the art. Particularly desirable compounds are disclosed in US 2006/0258721 and herein and have the formula:

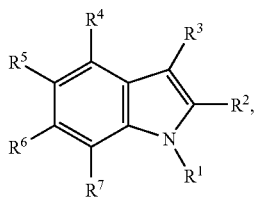

(I)

or a pharmaceutically acceptable salt or prodrug thereof, wherein, $R^1$ is H, optionally substituted $C_{1-6}$ alkyl, optionally substituted $C_{1-4}$ alkaryl, optionally substituted $C_{1-4}$ alkheterocyclyl, or optionally substituted $C_{3-8}$ cycloalkyl;

each of $R^2$ and $R^3$ is, independently, H, Hal, optionally substituted $C_{1-6}$ alkyl, optionally substituted $C_{6-10}$ aryl, optionally substituted $C_{1-4}$ alkaryl, optionally substituted $C_{2-9}$ bridged heterocyclyl, optionally substituted $C_{1-4}$ bridged alkheterocyclyl, optionally substituted $C_{2-9}$ heterocyclyl, optionally substituted $C_{1-4}$ alkheterocyclyl, or optionally substituted $C_{3-8}$ cycloalkyl;

each of $R^4$ and $R^7$ is, independently, H, F, $C_{1-6}$ alkyl, or $C_{1-6}$ alkoxy;

$R^5$ is H, $R^{5A}C(NH)NH(CH_2)_{r5}$, or $R^{5B}NHC(S)NH(CH_2)_{r5}$, wherein r5 is an integer from 0 to 2, $R^{5A}$ is optionally substituted $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, optionally substituted aryloyl, or optionally substituted $C_{1-4}$ thioalkheterocyclyl; and $R^{5B}$ is $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, or optionally substituted aryloyl; and $R^6$ is H, F, $R^{6A}C(NH)NH(CH_2)_{r6}$, or $R^{6B}NHC(S)NH(CH_2)_{r6}$, wherein r6 is an integer from 0 to 2, $R^{6A}$ is optionally substituted $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, optionally substituted aryloyl, or optionally substituted $C_{1-4}$ thioalkheterocyclyl; and $R^{6B}$ is $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, or optionally substituted aryloyl.

In a preferred embodiment, $R^6$ is H.

Specific examples of these compounds include those in Table 2.

TABLE 2

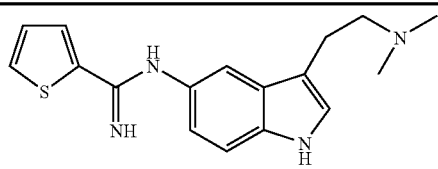

TABLE 2-continued

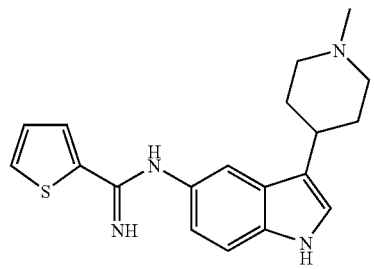

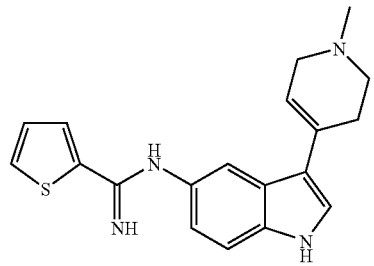

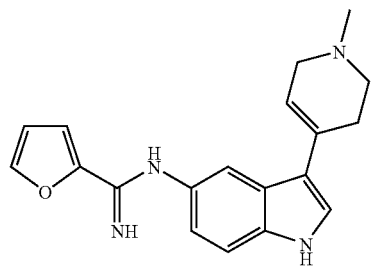 [SMILES: CN1CC=C(c2c[nH]c3ccc(NC(=N)c4ccco4)cc23)CC1]

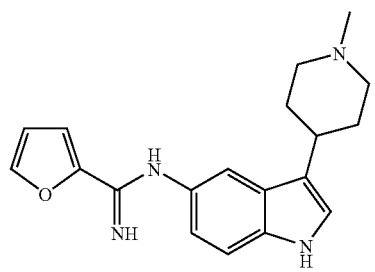 [SMILES: CN1CCC(c2c[nH]c3ccc(NC(=N)c4ccco4)cc23)CC1]

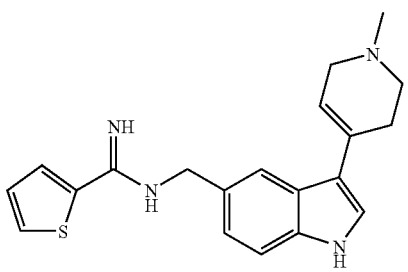 [SMILES: CN1CC=C(c2c[nH]c3ccc(CNC(=N)c4cccs4)cc23)CC1]

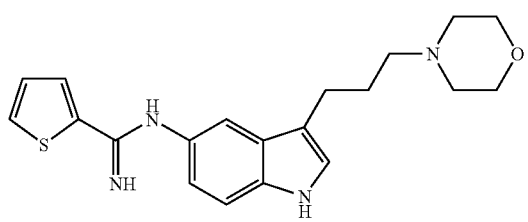 [SMILES: N=C(Nc1ccc2[nH]cc(CCCN3CCOCC3)c2c1)c1cccs1]

TABLE 2-continued
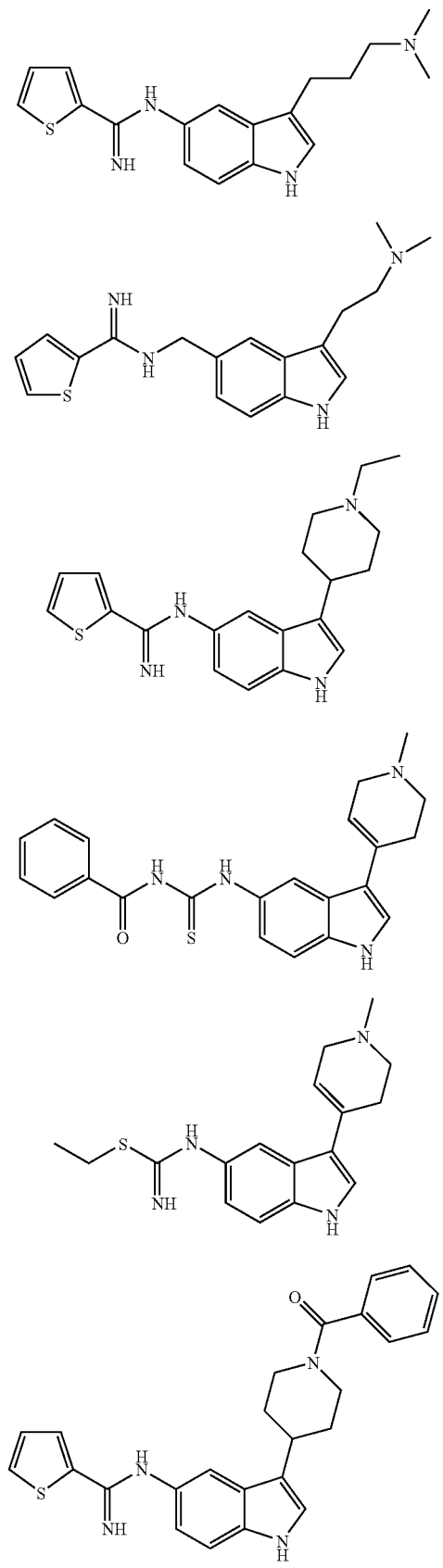
TABLE 2-continued
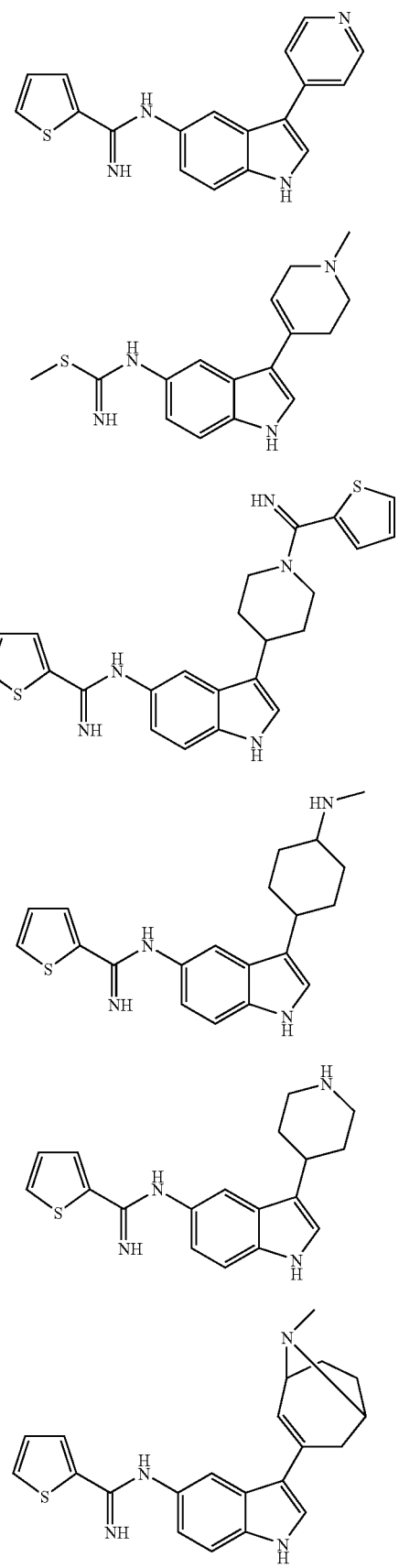

TABLE 2-continued
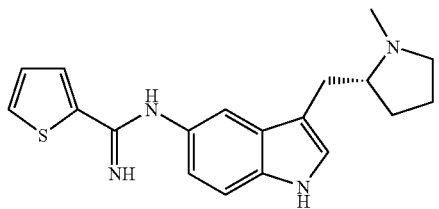
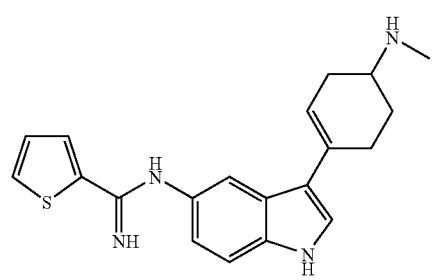 [SMILES: CNC1CC=C(c2c[nH]c3ccc(NC(=N)c4cccs4)cc23)CC1]
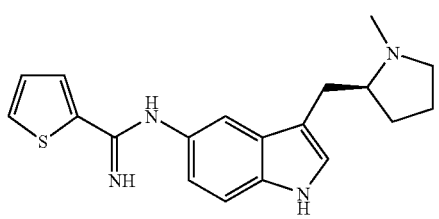 [SMILES: CN1CCC[C@H]1Cc1c[nH]c2ccc(NC(=N)c3cccs3)cc12]
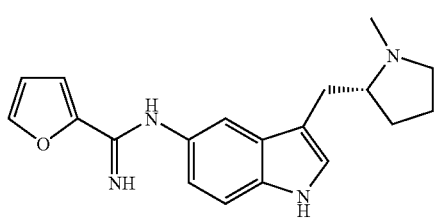 [SMILES: CN1CCC[C@@H]1Cc1c[nH]c2ccc(NC(=N)c3ccco3)cc12]
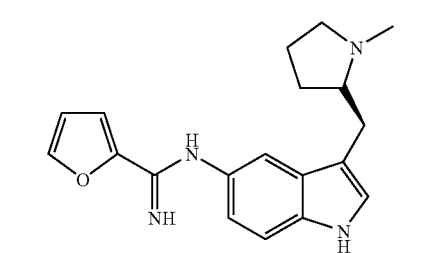
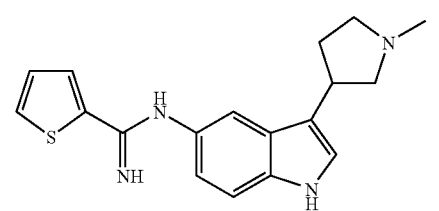 [SMILES: CN1CCC(c2c[nH]c3ccc(NC(=N)c4ccco4)cc23)C1]
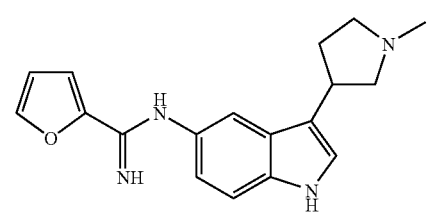
TABLE 2-continued
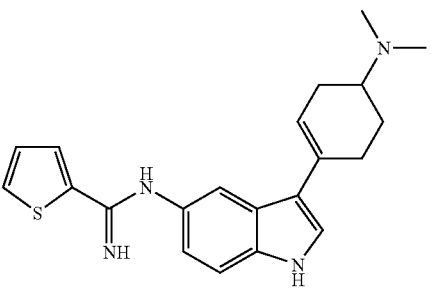 [SMILES: CN(C)C1CC=C(c2c[nH]c3ccc(NC(=N)c4cccs4)cc23)CC1]
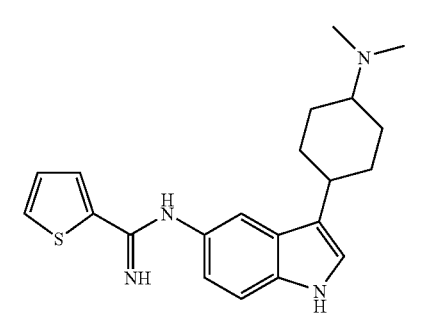 [SMILES: CN(C)C1CCC(c2c[nH]c3ccc(NC(=N)c4cccs4)cc23)CC1]
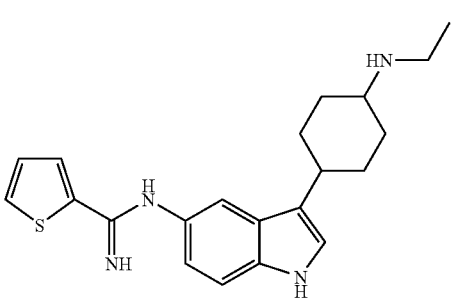 [SMILES: CCNC1CCC(c2c[nH]c3ccc(NC(=N)c4cccs4)cc23)CC1]
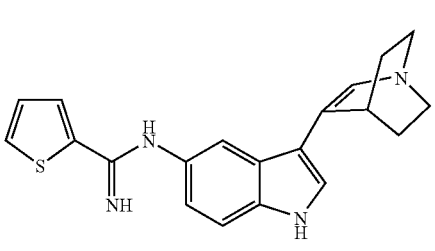 [SMILES: N=C(Nc1ccc2[nH]cc(C3=CN4CCC3CC4)c2c1)c1cccs1]
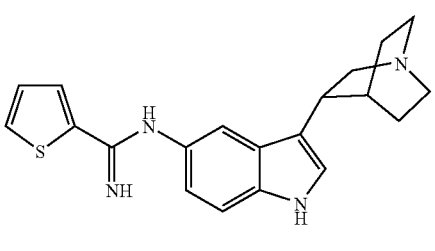 [SMILES: N=C(Nc1ccc2[nH]cc(C3CN4CCC3CC4)c2c1)c1cccs1]
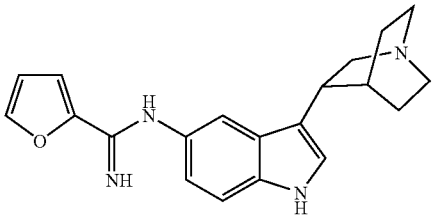 [SMILES: N=C(Nc1ccc2[nH]cc(C3CN4CCC3CC4)c2c1)c1ccco1]

TABLE 2-continued

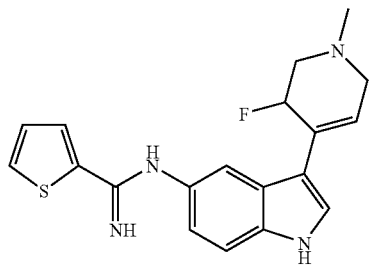 [SMILES: CN1CC=C(c2c[nH]c3ccc(NC(=N)c4cccs4)cc23)C(F)C1]

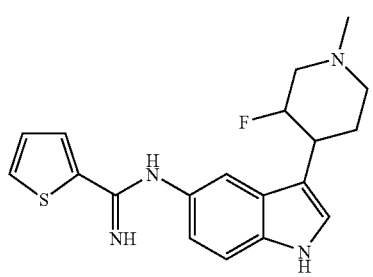 [SMILES: CN1CCC(c2c[nH]c3ccc(NC(=N)c4cccs4)cc23)C(F)C1]

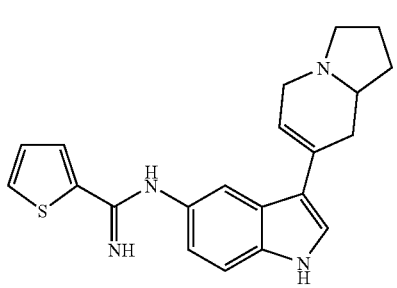 [SMILES: N=C(Nc1ccc2[nH]cc(C3=CCN4CCCC4C3)c2c1)c1cccs1]

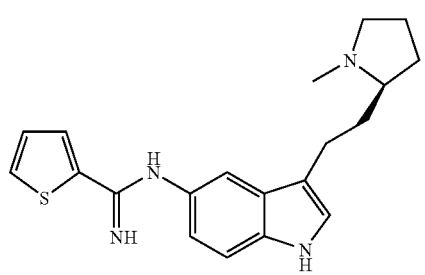 [SMILES: CN1CCC[C@H]1CCc1c[nH]c2ccc(NC(=N)c3cccs3)cc12]

Methods of synthesizing each of the compounds in Table 2 are provided in US 2006/0258721, hereby incorporated by reference.

Preferred compounds include

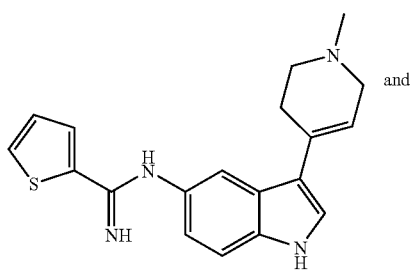

and

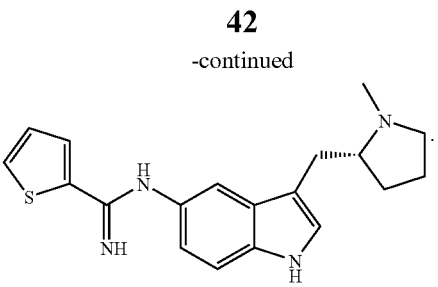

Additional 3,5 substituted indoles include

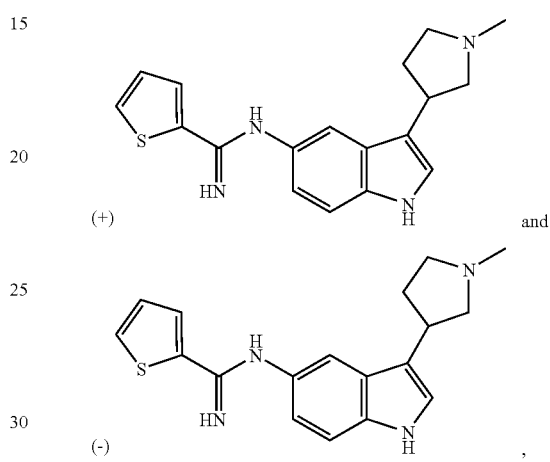

(+) and (−), the racemic mixture of which is disclosed in US 2006/0258721.

Another preferred compound is

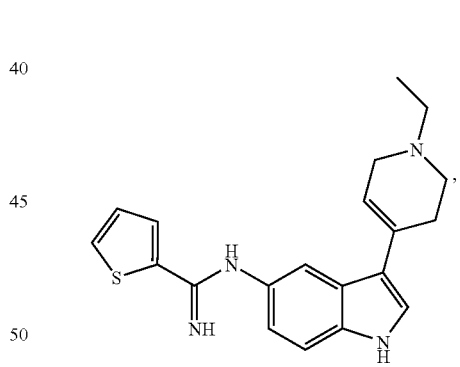

the synthesis of which is described herein.

Additional preferred compounds include:

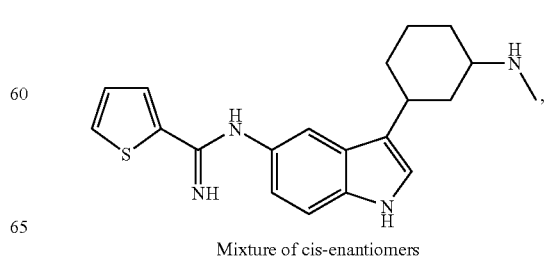

Mixture of cis-enantiomers

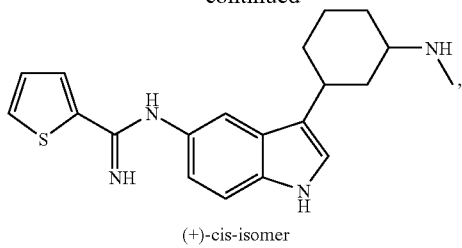

(+)-cis-isomer

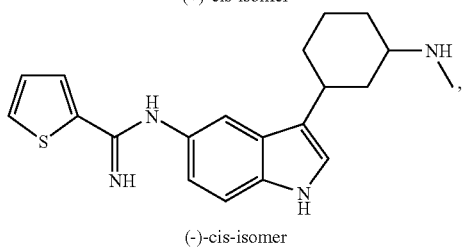

(−)-cis-isomer

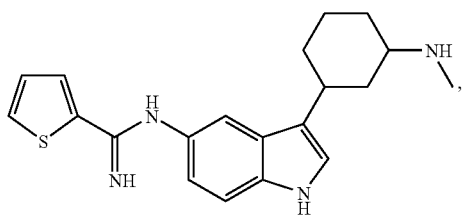

Mixture of trans-enantiomers

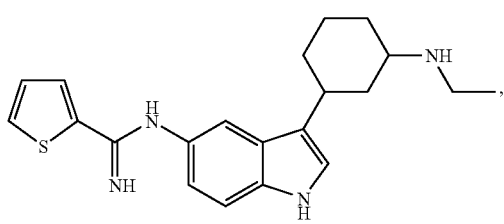

Mixture of trans-enantiomers

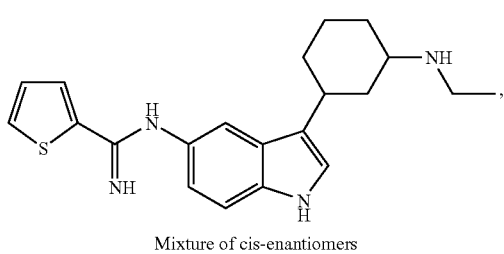

Mixture of cis-enantiomers

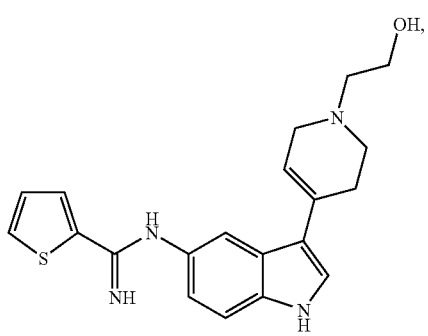

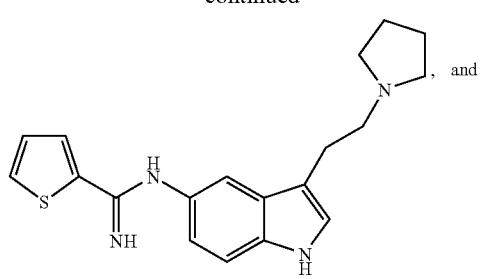

and

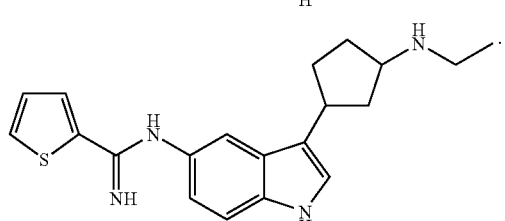

Mixture of four isomers

Methods of Preparing Compounds of the Invention

The synthesis of 3,5-substituted indoles is described generally in U.S. Pat. No. 7,375,219, herein incorporated by reference, and additional examples are described herein. The synthesis for 1,3-disubstituted hexane ring is shown below:

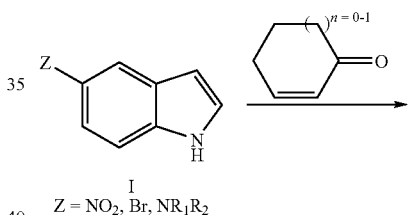

I
Z = NO$_2$, Br, NR$_1$R$_2$

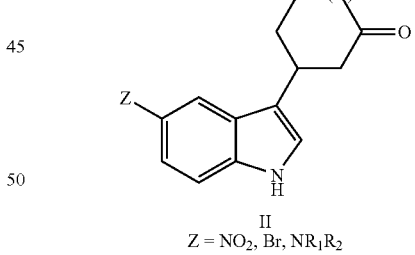

II
Z = NO$_2$, Br, NR$_1$R$_2$

Reductive amination

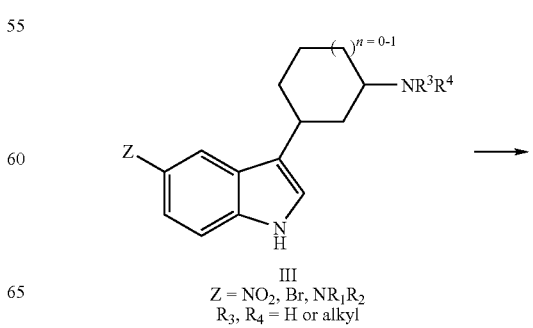

III
Z = NO$_2$, Br, NR$_1$R$_2$
R$_3$, R$_4$ = H or alkyl

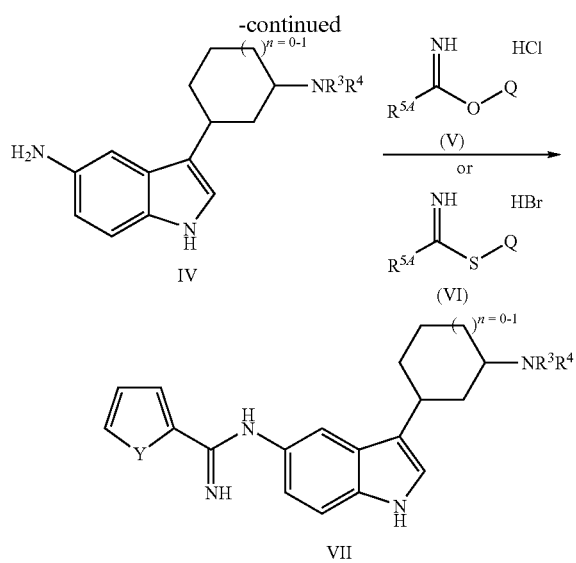

The Michael addition of a suitable indole derivative to enone was carried according to the literature proceed reported in *J. Org. Chem.* 68: 2109-2114 (2003). Compound III can be synthesized by the standard reductive amination with various primary and secondary amines in presence of sodium triacetoxy borohydride and an acid, preferably acetic acid. If the product is a secondary amine (where the reductive amination was carried with primary amine), it can be protected with a suitable protective group such as tert-butoxy carbonyl before proceeding further. The amine of formula IV can be achieved by the reduction of the nitro group under Pd—C/$H_2$ reduction conditions. In case of bromo-substitution, it can be converted into a primary amine under standard Buchwald amination conditions using $Pd_2(dba)_3$ (see, e.g., U.S. Pat. No. 7,375, 219). The primary amine IV can be converted into compound V by reaction with amidine reagent as described in U.S. Pat. No. 7,375,219.

Pharmaceutical Compositions

The compounds of the invention are preferably formulated into pharmaceutical compositions for administration to human subjects in a biologically compatible form suitable for administration in vivo. Accordingly, in another aspect, the present invention provides a pharmaceutical composition comprising a compound of the invention in admixture with a suitable diluent or carrier.

The compounds of the invention may be used in the form of the free base, in the form of salts, solvates, and as prodrugs. All forms are within the scope of the invention. In accordance with the methods of the invention, the described compounds or salts, solvates, or prodrugs thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound of the invention may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound of the invention may be incorporated with an excipient and used in the form of ingestible tablets, buccal tablets, troches, capsules, elixirs, suspensions, syrups, wafers, and the like.

A compound of the invention may also be administered parenterally. Solutions of a compound of the invention can be prepared in water suitably mixed with a surfactant, such as hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2003-20th edition) and in The United States Pharmacopeia: The National Formulary (USP 24 NF19), published in 1999.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe.

Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant, such as fluorochlorohydrocarbon. The aerosol dosage forms can also take the form of a pump-atomizer.

Compositions suitable for buccal or sublingual administration include tablets, lozenges, and pastilles, where the active ingredient is formulated with a carrier, such as sugar, acacia, tragacanth, or gelatin and glycerine. Compositions for rectal administration are conveniently in the form of suppositories containing a conventional suppository base, such as cocoa butter.

The compounds of the invention may be administered to an animal alone or in combination with pharmaceutically acceptable carriers, as noted above, the proportion of which is determined by the solubility and chemical nature of the compound, chosen route of administration, and standard pharmaceutical practice.

The dosage of the compounds of the invention, and/or compositions comprising a compound of the invention, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds of the invention may be administered initially in a suitable dosage that may be adjusted as required, depending on the clinical response. In general, satisfactory results may be obtained when the compounds of the invention are administered to a human at a daily dosage of between 0.05 mg and 3000 mg (measured as the solid form). A preferred dose ranges between 0.05-500 mg/kg, more preferably between 0.05-50 mg/kg.

A compound of the invention can be used alone or in combination with other agents that have NOS activity, or in combination with other types of treatment (which may or may not inhibit NOS) to treat, prevent, and/or reduce the risk of stroke, neuropathic or migraine pain, or other disorders that benefit from NOS inhibition. In combination treatments, the dosages of one or more of the therapeutic compounds may be reduced from standard dosages when administered alone. In this case, dosages of the compounds when combined should provide a therapeutic effect. Such additional agents include a $5HT_{1B}$ and/or $5HT_{1D}$ receptor agonist, e.g., a triptan, such as sumatriptan, rizatriptan, naratriptan, zolmitriptan, eletriptan, almotriptan, or frovatriptan.

Other agents include analgesics, antidepressants, and anticonvulsants. Specific examples are provided herein.

Example 1

N-(3-(1-Methylpyrrolidin-3-yl)-1H-indol-5-yl) thiophene-2-carboximidamide (6a and 6b)

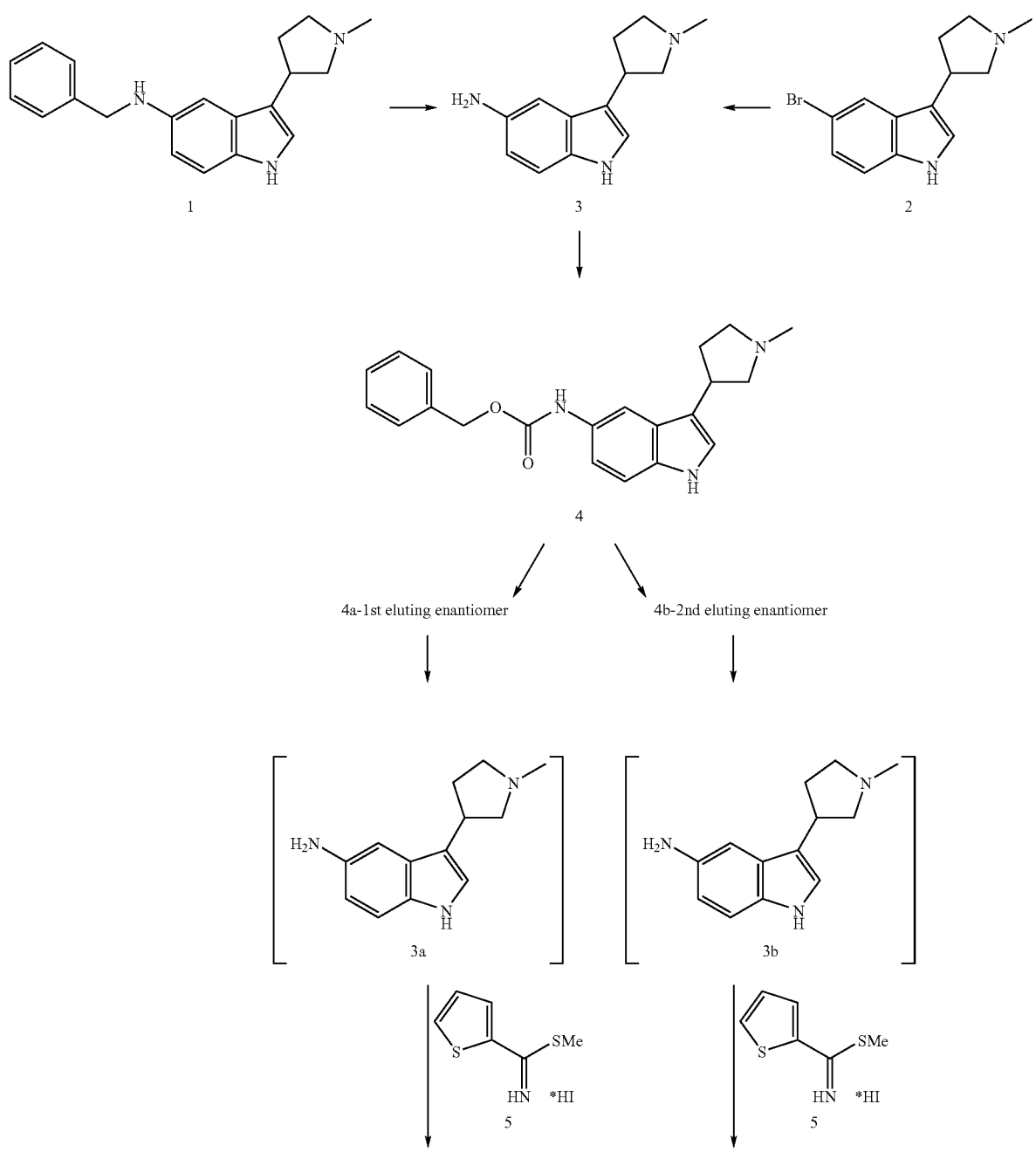

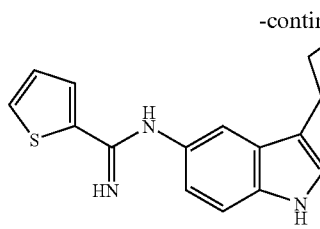
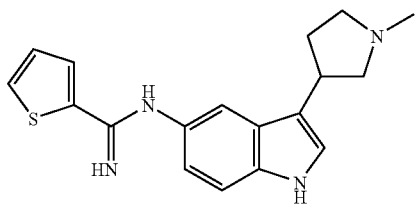

6a-2nd eluting enantiomer | 6b-1st eluting enantiomer (a) N-Benzyl-3-(1-methylpyrrolidin-3-yl)-1H-indol-5-anine (1)

Macor, J. E et. al J. Med. Chem., 37, 2509-2512, (1994).

(b) 5-Bromo-3-(1-methylpyrrolidin-3-yl)-1H-indol-5-amine (2)

Macor, J. E et al Synthesis, (1997), 443-449.

(c) 3-(1-Methylpyrrolidin-3-yl)-1H-indol-5-amine (3)

Method (1): N-benzyl-3-(1-methylpyrrolidin-3-yl)-1H-indol-5-amine 1, (4.0 g, 13.097 mmol) was dissolved in anhydrous ethanol (60 mL) in a dry argon purged flask. Palladium hydroxide, 20 wt % on carbon, wet (1.92 g, 2.734 mmol) is quickly added and the atmosphere from the flask evacuated by vacuum pump and replaced with hydrogen from a balloon. The atmosphere is evacuated from the flask and replaced with hydrogen twice more and the mixture stirred under a hydrogen atmosphere at room temperature. After 48 hours, the mixture is filtered through a pad of celite to remove insolubles, the pad washed with anhydrous ethanol (30 mL) and the solvent evaporated. The crude amine is purified via chromatography on silica gel (2M $NH_3$ in $MeOH:CH_2Cl_2$, 1:9 to 1:4) to yield a pale yellow foam, 3 (1.50 g, 53.6% yield). $^1H$ NMR (DMSO-$d_6$): δ 1.80-1.92 (m, 1H), 2.10-2.24 (m, 1H), 2.30 (s, 3H), 2.40 (t, 2H, J=8.4 Hz), 2.66-2.78 (m, 1H), 2.93 (t, 1H, J=8.2 Hz), 3.35-3.46 (m, 1H), 4.42 (br s, 2H), 6.46 (dd, 1H, J=2.1, 8.5 Hz), 6.70 (d, 1H, J=2.0 Hz), 6.92 (d, 1H, J=2.3 Hz), 7.01 (d, 1H, J=8.5 Hz), 10.23 (br s, 1H); MS (ESI+) m/z (%): 216 (MH+, 100), 173 (41).

Method (2): 5-Bromo-3-(1-methylpyrrolidin-3-yl)-1H-indole 2, (405 mg, 1.4507 mmol), Tris(dibenzylideneacetone) dipalladium (0) (132.8 mg, 0.1450 mmol) and anhydrous tetrahydrofuran (20 mL) were charged to a dry argon purged flask fitted with magnetic stir bar and condenser. A solution of tri-tert-butylphosphine (10 wt % in hexane, 863 μL, 0.2901 mmol) is added followed by drop wise addition of a 1M tetrahydrofuran solution of Lithium bis(trimethylsilyl)amide (4.35 mL, 4.35 mmol) and the mixture was refluxed for a period of 70 minutes. The mixture was cooled to room temperature then to 0° C., quenched with 1M HCl (10 mL) and stirred for 10 minutes. The solution was diluted with ethyl acetate and 5M $NH_4OH$ added to adjust pH to 10. The mixture was transferred to a separatory funnel and the organic layer collected. The aqueous layer was further extracted with ethyl acetate and the combined organic layers were washed with brine, dried over magnesium sulphate, filtered, concentrated and the residue purified via dry chromatography on silica gel, eluting with ~25 mL portions of solvent system 20% 2M $NH_3$ in methanol/80% dichloromethane to yield a yellow residue, 3 (162 mg, 51.9% yield).

$^1H$ NMR (DMSO-$d_6$): Identical to that prepared via Method 1 above.

(d) Benzyl 3-(1-methylpyrrolidin-3-yl)-1H-indol-5-ylcarbamate ((±)-4)

Method (1): 3-(1-Methylpyrrolidin-3-yl)-1H-indol-5-amine 3, (96 mg, 0.446 mmol), Dioxane (6 mL), 1M NaOH (0.89 mL, 0.89 mmol) and water (0.11 mL) were charged to a flask fitted with a stir bar and Argon atmosphere and the mixture cooled to 0° C. in an ice-bath. Benzyl chloroformate (0.125 mL, 0.892 mmol) dissolved in dioxane (2 mL) is added dropwise at <5° C. The ice-bath was removed and mixture allowed to warm to room temperature. After 1 hour the mixture was partitioned between ethyl acetate (50 mL) and saturated aqueous $NaHCO_3$ (10 mL) and the organic layer collected. The aqueous layer was further extracted with ethyl acetate and the combined organic layers were washed with brine, dried over sodium sulphate, filtered, concentrated and the residue purified via chromatography on silica gel (10% 2M $NH_3$ in methanol/90% dichloromethane) to yield an off-white solid (±)-4 (110 mg, 70.6% yield). $^1H$ NMR (DMSO-$d_6$): δ 1.82-1.93 (m, 1H), 2.12-2.27 (m, 1H), 2.30 (s, 3H), 2.40 (t, 2H, J=8.4 Hz), 2.68-2.79 (m, 1H), 2.95 (t, 1H, J=8.2 Hz), 3.40-3.52 (m, 1H), 5.14 (s, 2H), 7.04-7.10 (2 m, 2H), 7.20-7.25 (m, 1H), 7.29-7.46 (m, 5H), 7.71 (br s, 1H), 9.45 (br s, 1H), 10.67 (br s, 1H); MS (ESI+) m/z (%): 350 (MH+, 100).

Method (2): Alternatively, (±)-4 was synthesized directly from N-benzyl-3-(1-methylpyrrolidin-3-yl)-1H-indol-5-amine, 1, without purification of the intermediate amine 3. N-benzyl-3-(1-methylpyrrolidin-3-yl)-1H-indol-5-amine 1, (4.8 g, 15.716 mmol) was dissolved in anhydrous ethanol (250 mL) in a dry argon purged flask. Palladium hydroxide, 20 wt % on carbon, wet (2.688 g) is quickly added and the atmosphere from the flask evacuated by vacuum pump and replaced with hydrogen from a balloon. The atmosphere is evacuated from the flask and replaced with hydrogen twice more and the mixture stirred under a hydrogen atmosphere at room temperature. After 44 hours, thin layer chromatography in a solvent system of (15% 2M $NH_3$ in methanol/85% dichloromethane) shows complete conversion to 3,3-(1-methylpyrrolidin-3-yl)-1H-indol-5-amine. The mixture is filtered through a pad of celite to remove insolubles, the pad washed with anhydrous ethanol (50 mL) and the solvent evaporated and compound dried briefly on vacuum pump, yielding 3.40 grams of a pink-purple solid. A stir bar and Argon atmosphere is charged to the flask. Dioxane (135 mL), 1M NaOH (31.43 mL, 31.43 mmol, 2.0 equiv) and water (3.8 mL) are added and the mixture cooled to 0° C. in an ice-bath. Benzyl chloroformate (4.42 mL, 31.432 mmol) dissolved in dioxane (40 mL) is added drop wise over ~20 mins at <5° C. The ice-bath was removed and mixture allowed to warm to room temperature. After 1 hour, the mixture was partitioned between ethyl acetate (500 mL) and saturated $NaHCO_3$ (50 mL) and the organic layer collected. The aqueous layer was further extracted with ethyl acetate and the combined organic layers were washed with brine, dried over sodium sulphate, filtered, concentrated and the residue purified via chromatography on silica gel (7.5% 2M $NH_3$ in methanol/92.5% dichloromethane to 10% 2M $NH_3$ in methanol/90% dichloromethane) to yield a off-white solid (±)-4 (3.18 g, 57.9% yield). $^1$H NMR (DMSO-$d_6$): identical to that prepared via Method 1 above.

(e) Benzyl 3-(1-methylpyrrolidin-3-yl)-1H-indol-5-ylcarbamate (4a and 4b)

Compounds 4a and 4b were separated from the corresponding racemate (±)-4 by preparative HPLC using a Chiralpak AD-H column, 5 cm×25 cm, eluting with Hexane/Isopropanol/Diethylamine (80/20/0.1) at a flow rate of 120 mL/minute.
Chiral HPLC Purity Conditions:
Column: ChiralPak AD-H, 4.6×250 mm.
Mobile Phase Hexane/Isopropanol/Diethylamine (80/20/0.1)
Flow Rate: 1 mL/minute
UV Detection: 240 nm
Sample Preparation: 1 mg/mL in mobile phase.
Injection Volume: 5 µL.
Compound 4a (first eluting isomer at 14.7 min.): $^1$H NMR (DMSO-$d_6$): δ 1.82-1.93 (m, 1H), 2.12-2.27 (m, 1H), 2.30 (s, 3H), 2.40 (t, 2H, J=8.4 Hz), 2.68-2.79 (m, 1H), 2.95 (t, 1H, J=8.2 Hz), 3.43-3.52 (m, 1H), 5.14 (s, 2H), 7.04-7.10 (2 m, 2H), 7.20-7.24 (m, 1H), 7.29-7.45 (m, 5H), 7.71 (br s, 1H), 9.43 (br s, 1H), 10.65 (br s, 1H); MS (ESI+) m/z (%): 350 (MH$^+$, 100). Compound 4b (second eluting isomer at 19.6 min.): $^1$H NMR (DMSO-$d_6$): δ 1.83-1.96 (m, 1H), 2.13-2.27 (m, 1H), 2.30 (s, 3H), 2.40 (t, 2H, J=8.4 Hz), 2.67-2.78 (m, 1H), 2.95 (t, 1H, J=8.2 Hz), 3.43-3.54 (m, 1H), 5.14 (s, 2H), 7.04-7.13 (2 m, 2H), 7.20-7.24 (m, 1H), 7.30-7.48 (m, 5H), 7.71 (br s, 1H), 9.43 (br s, 1H), 10.65 (br s, 1H); MS (ESI+) m/z (%): 350 (MH$^+$, 100).

(f) N-(3-(1-Methylpyrrolidin-3-yl)-1H-indol-5-yl)thiophene-2-carboximidamide (6a and 6b)

Benzyl 3-(1-methylpyrrolidin-3-yl)-1H-indol-5-yl carbamate 4b, (>99% ee, 1.90 g, 5.437 mmol) was dissolved in anhydrous ethanol (60 mL) in a dry argon purged flask. Palladium, 10 wt % on carbon (578.5 mg, 0.544 mmol) is quickly added and the atmosphere from the flask evacuated by vacuum pump and replaced with hydrogen from a balloon. The atmosphere is evacuated from the flask and replaced with hydrogen twice more and the mixture stirred under a hydrogen atmosphere at room temperature. After 5 hours, thin layer chromatography in a solvent system of (20% 2M $NH_3$ in methanol/80% dichloromethane) shows complete conversion to 3b, 3-(1-methylpyrrolidin-3-yl)-1H-indol-5-amine. The mixture is filtered through a pad of celite to remove insolubles, the pad washed with anhydrous ethanol (30 mL). To the ethanolic solution of 3b is charged a stir bar and Argon atmosphere and methyl thiophene-2-carbimidothioate hydroiodide 5 (2.48 g, 8.699 mmol; prepared according to a known procedure, see US 20060258721) is added to the flask and the reaction was stirred under Ar at ambient temperature for 19 hours. At that time, the solvent was evaporated and the residue was partitioned between $H_2O$ and ethyl acetate and 1M NaOH solution added to adjust pH to 10. The mixture was transferred to a separatory funnel and the organic layer collected. The aqueous layer was further extracted with ethyl acetate and the combined organic layers were washed with brine, dried over magnesium sulphate, filtered, concentrated and the residue purified via dry chromatography, eluting with ~50 mL portions of solvent system 15% 2M $NH_3$ in methanol/85% dichloromethane to 20% 2M $NH_3$ in methanol/80% dichloromethane to yield a yellow residue 6b (1.40 g, 79.4% yield).

In a like manner starting from Benzyl 3-(1-methylpyrrolidin-3-yl)-1H-indol-5-yl carbamate, 4a (>99% ee, 2.0 g, 5.723 mmol) was prepared as a yellow solid 6a (1.10 g, 59.3% yield).

Chiral HPLC Purity Conditions:
Column: ChiralPak AD-H, 4.6×250 mm.
Mobile Phase Hexane/Ethanol/Diethylamine (90/10/0.1)
Flow Rate: 0.4 mL/minute
UV Detection: 254, 230 nm
Sample Preparation: 1 mg/mL in Ethanol.
Injection Volume: 5 µL
Compound 6b (first eluting isomer at 75.0 min.): $^1$H NMR (DMSO-$d_6$) δ: 1.83-1.98 (m, 1H), 2.16-2.28 (m, 1H), 2.32 (s, 3H), 2.50-2.60 (m, 2H), 2.66-2.74 (m, 1H), 2.95 (t, 1H, J=8.4 Hz), 3.45-3.56 (m, 1H), 6.32 (br s, 2H), 6.64 (dd, 1H, J=8.4, 1.8 Hz), 7.02 (d, 1H, J=1.4 Hz), 7.08-7.11 (m, 2H), 7.27 (d, 1H, J=8.5 Hz), 7.59 (d, 1H, J=4.5 Hz), 7.71 (d, 1H, J=3.3 Hz), 10.60 (br s, 1H). MS (ESI+) m/z (%): 325 (MH$^+$, 89), 282 (90), 163 (100). EI-HRMS calculated for $C_{18}H_{20}N_4S$ (M$^+$) 324.1409; observed: 324.1407.

Compound 6a (second eluting isomer at 83.1 min.): $^1$H NMR (DMSO-$d_6$) δ: 1.83-1.96 (m, 1H), 2.19-2.28 (m, 1H), 2.33 (s, 3H), 2.50-2.62 (m, 2H), 2.66-2.74 (m, 1H), 2.95 (t, 1H, J=8.4 Hz), 3.45-3.56 (m, 1H), 6.32 (br s, 2H), 6.64 (dd, 1H, J=8.4, 1.8 Hz), 7.02 (d, 1H, J=1.4 Hz), 7.08-7.11 (m, 2H), 7.27 (d, 1H, J=8.5 Hz), 7.59 (m, 1H) 7.71 (d, 1H, J=3.3 Hz), 10.62 (br s, 1H). MS (ESI+) m/z (%): 325 (MH$^+$, 89), 282 (90), 163 (100). EI-HRMS calculated for $C_{18}H_{20}N_4S$ (M$^+$) 324.1409; observed: 324.1404.

(g) Dihydrochloride salt of N-(3-(1-methylpyrrolidin-3-yl)-1H-indol-5-yl)thiophene-2-carboximidamide (6b)

N-(3-(1-Methylpyrrolidin-3-yl)-1H-indol-5-yl)thiophene-2-carboximidamide 6b, (2.40 g, 7.398 mmol) was dissolved in anhydrous methanol (70 mL) in a dry argon purged flask and treated with 1M HCl/Et$_2$O (22.2 mL, 22.2 mmol) for 60 minutes at room temperature. The solvent was evaporated and the residue dried to yield a pale yellow solid 6b.2HCl, (2.60 g, 88.5% yield). $[α_D]^{29}$ (c=1.0, MeOH)=+13.0

(h) Dihydrochloride salt of N-(3-(1-methylpyrrolidin-3-yl)-1H-indol-5-yl)thiophene-2-carboximidamide (6a)

N-(3-(1-Methylpyrrolidin-3-yl)-1H-indol-5-yl)thiophene-2-carboximidamide 6a, (1.10 g, 3.391 mmol) was dissolved in anhydrous methanol (25 mL) in a dry argon purged flask and treated with 1M HCl/Et$_2$O (10.17 mL, 10.17 mmol) for 30 minutes at room temperature. The solvent was evaporated and the residue dried to yield a pale yellow solid 6a.2HCl, (1.15 g, 85.4% yield). $[\alpha_D]^{29}$ (c=1.0, MeOH)=−13.0

Example 2

Attempted resolution of N-benzyl-3-(1-methylpyrrolidin-3-yl)-1H-indol-5-amine (1)

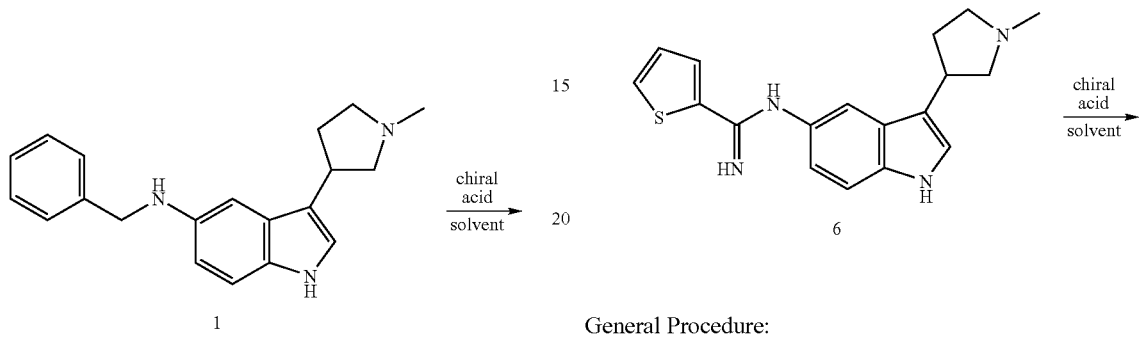

General Procedure:

N-Benzyl-3-(1-methylpyrrolidin-3-yl)-1H-indol-5-amine 1, (1.0 g, 3.274 mmol) was dissolved in an anhydrous solvent (~10 mL) in a dry argon purged flask. To this solution was added a solution of chiral acid (0.5 equiv.) in anhydrous solvent (~10 mL) with swirling. If an immediate cloudiness appeared in the solution, further anhydrous solvent was added slowly with heating until the mixture was homogeneous. The mixture was allowed to cool slowly. If a viscous gum precipitated on the walls of the flask, further anhydrous solvent was added with heating until homogenous, and the solution allowed to cool to RT. Where no precipitation was observed at RT the flask was cooled to 0° C. overnight, and/or an antisolvent was added to try to induce crystallization. Results are summarized in Table 3 below.

Example 3

Attempted resolution of N-(3-(1-methylpyrrolidin-3-yl)-1H-indol-5-yl)thiophene-2-carboximidamide (6)

General Procedure:

N-(3-(1-methylpyrrolidin-3-yl)-1H-indol-5-yl)thiophene-2-carboximidamide 6, (0.78 g, 2.404 mmol) was dissolved in an anhydrous solvent (~10 mL) in a dry argon purged flask. To this solution was added a solution of chiral acid (0.5 equiv.) in anhydrous solvent (~10 mL) with swirling. If an immediate cloudiness appeared in the solution, further anhydrous solvent was added slowly with heating until the mixture was homogeneous. The mixture was allowed to cool slowly. If a viscous gum precipitated on the walls of the flask, further anhydrous solvent was added with heating until homogenous, and the solution allowed to cool to RT. Where no precipitation was observed at room temperature the flask was cooled to 0° C. overnight to try to induce crystallization. Results are summarized in Table 4 below.

TABLE 3

Attempted resolution of N-benzyl-3-(1-methylpyrrolidin-3-yl)-1H-indol-5-amine (1):

| | MeOH | MeOH + Et$_2$O | EtOH | IPA | Acetone |
|---|---|---|---|---|---|
| Dibenzoyl-tartaric acid-(L) | | | Gum, dilute, add Acetone-no ppt. | | |
| Di-p-toluoyl-tartaric acid-(L) | | | Gum or no ppt. | Gum, dilute, add Et$_2$O-no ppt. | No ppt. Add Et$_2$O-gum |
| Dibenzoyl-tartaric acid-(D) | | | Gum 0% ee gum 0% ee filtrate | | |
| Di-p-toluoyl-tartaric acid-(D) | | | Gum 0% ee gum 0% ee filtrate | | |
| (R)-camphor sulfonic acid | No ppt 0° C.-no ppt | Cloudy-no ppt. | | Gum | No ppt Add Et$_2$O |
| (S)-camphor sulfonic acid | No ppt 0° C.-no ppt | | | Gum | No ppt Add Et$_2$O |
| (R)-mandelic acid | No ppt 0° C.-no ppt | Cloudy-no ppt | | Solid ~6% ee gum ~6% ee filtrate | |
| (S)-mandelic acid | No ppt 0° C.-no ppt | | | Solid ~6% ee gum ~6% ee filtrate | |

TABLE 4

Attempted resolution of N-(3-(1-methylpyrrolidin-3-yl)-1H-indol-5-yl)thiophene-2-carboximidamide (6):

| | MeOH | MeOH + EtOH | EtOH |
|---|---|---|---|
| Tartaric acid-(L) | No ppt 0° C.-no ppt | Gum | Gum |
| Dibenzoyl-tartaric acid-(L) | No ppt 0° C.-no ppt | Gum | Gum |
| Di-p-toluoyl-tartaric acid-(L) | | | No ppt 0° C.-no ppt |
| (S)-camphor sulfonic acid | | | No ppt 0° C.-no ppt |
| (S)-mandelic acid | | | No ppt 0° C.-no ppt |

Example 4

Attempted resolution of 5-bromo-3-(1-methylpyrrolidin-3-yl)-1H-indol-5-amine (2)

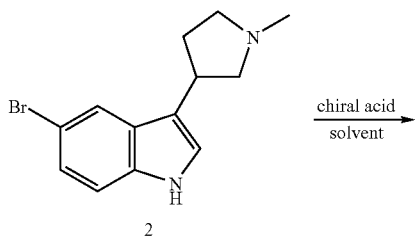 [SMILES: CN1CCC(c2c[nH]c3ccc(Br)cc23)C1]

General Procedure:

5-Bromo-3-(1-methylpyrrolidin-3-yl)-1H-indol-5-amine 2, (0.544 g, 1.949 mmol) was dissolved in an anhydrous solvent (~8 mL) in a dry argon purged flask. To this solution was added a solution of chiral acid (0.5 equiv.) in anhydrous solvent (~2.5 mL) with swirling. The mixture was allowed to cool slowly to RT. Where no precipitation was observed at RT the flask was cooled to 0° C. overnight, and/or an antisolvent was added to try to induce crystallization. Results are summarized in Table 5 below.

TABLE 5

Attempted resolution of 5-bromo-3-(1-methylpyrrolidin-3-yl)-1H-indol-5-amine (2):

| | MeOH, RT | MeOH, 0° C. | Conc to ½ volume. | Add IPA until cloudy |
|---|---|---|---|---|
| (L)-tartaric acid | No ppt. | No ppt. | No ppt. | gum |
| Di-benzoyl-(L)-tartaric acid | No ppt. | No ppt. | No ppt. | gum |
| Di-p-toluyl-(L)-tartaric acid | No ppt. | No ppt. | No ppt. | gum |
| (1S)-camphor sulfonic acid | No ppt. | No ppt. | No ppt. | No ppt. |
| (S)-mandelic acid | No ppt. | No ppt. | No ppt. | No ppt. |

Example 5

Attempted chiral HPLC separation of enantiomers of N-(3-(1-methylpyrrolidin-3-yl)-1H-indol-5-yl)thiophene-2-carboximidamide (6)

N-(3-(1-Methylpyrrolidin-3-yl)-1H-indol-5-yl)thiophene-2-carboximidamide (6), was subjected to a screening protocol to determine the feasibility of a large scale chromatographic enantioselective separation.

Results are outlined in Table 6 below.

TABLE 6

Attempted chiral HPLC/SFC separation of enantiomers of N-(3-(1-methylpyrrolidin-3-yl)-1H-indol-5-yl)thiophene-2-carboximidamide (6): Chiral Screening Summary Company Name:
Compound Name:
Date:

| | LC Results | | | SFC Results | | |
|---|---|---|---|---|---|---|
| Columns Tested: | Baseline resolved | Partially resolved | Not resolved | Baseline resolved | Partially resolved | Not resolved |
| Whelk-0 1 | | ✓ | | | ✓ | |
| ULMO | | | | | ✓ | |
| DACH-DNB | | ✓ | | | | |
| Pirkle 1-J | | ✓ | | | | |
| β-Gem | | ✓ | | | | |
| α-Burke 2 | | ✓ | | | | |
| Phenylglycine | | ✓ | | | | |
| Leucine | | ✓ | | | | |
| Chiralpak AD | | | | | | ✓ |
| Chiracel OJ | | | | | | ✓ |
| ChiralpakAS | | | | | | ✓ |
| RegisCell | | | | | | ✓ |

Example 6

Attempted chiral HPLC/SFC separation of enantiomers of N-benzyl-3-(1-methylpyrrolidin-3-yl)-1H-indol-5-amine (1); 5-bromo-3-(1-methylpyrrolidin-3-yl)-1H-indol-5-amine (2); 3-(5-bromo-1H-indol-3-yl)-1-methylpyrrolidine-2,5-dione (7) and N-(3-(1-methyl-2,5-dioxopyrrolidin-3-yl)-1H-indol-5-yl)benzamide (8)

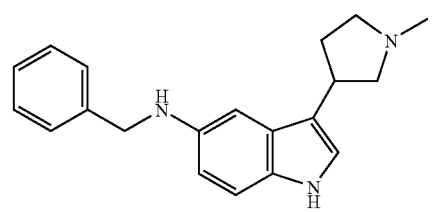

1

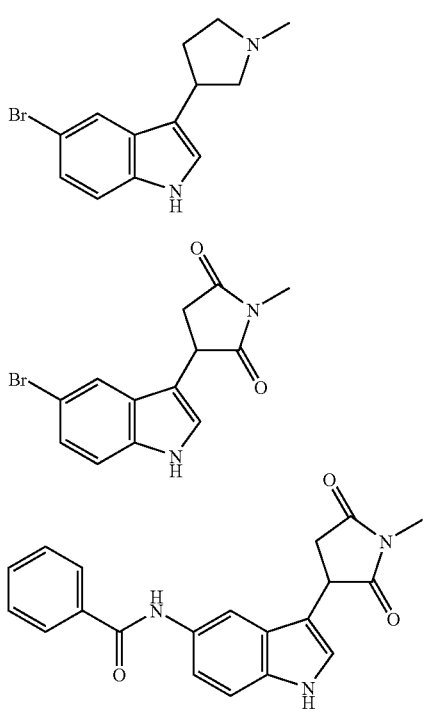

In a like manner, N-benzyl-3-(1-methylpyrrolidin-3-yl)-1H-indol-5-amine (1); 5-bromo-3-(1-methylpyrrolidin-3-yl)-1H-indol-5-amine (2); 3-(5-bromo-1H-indol-3-yl)-1-methylpyrrolidine-2,5-dione (7) (prepared according to Macor et al., *Synthesis*, 443-449 (1997)) and N-(3-(1-methyl-2,5-dioxopyrrolidin-3-yl)-1H-indol-5-yl)benzamide (8) (prepared according to Macor et al., *Synthesis*, 443-449 (1997)) were subjected to a screening protocol to determine the feasibility of a large scale chromatographic enantioselective separation. In all cases, the compounds either showed insufficient resolution or exhibited limited chiral stability on isolation.

For example, compound 1 was screened utilizing columns; Chiralpak AD-H, Chiralpak AS-H, Chiralcel OJ-H, Chiralcel OD-H, Chiralcel OB-H, Sepapak-3 and Whelk-01 (R,R) with solvents MeOH, EtOH, IPA, ACN with or without added 0.1% diethylamine or added 0.1% methane sulfonic acids where appropriate.

Example 7

1-((5-Bromo-3-(1-methylpyrrolidin-3-yl)-1H-indol-1-ylsulfonyl)methyl)-7,7-dimethylbicyclo[2.2.1]heptan-2-one (9)

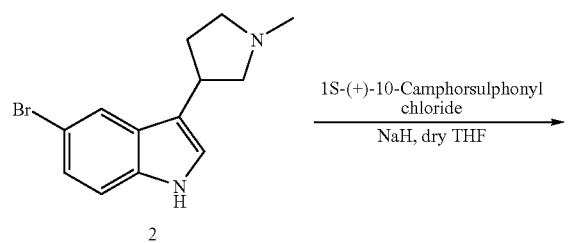

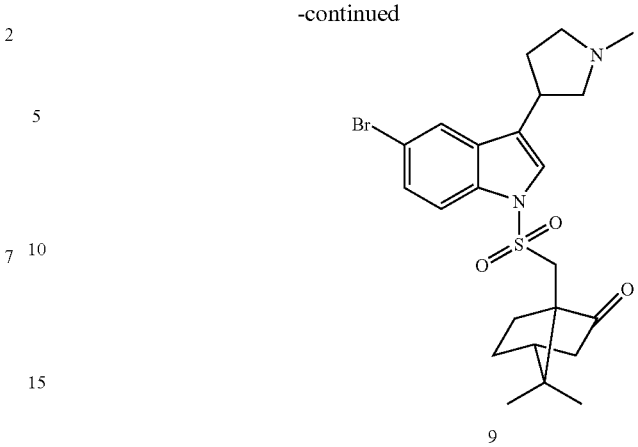

A solution of compound 2 (0.095 g, 0.34 mmol) in dry THF (3 mL) was treated with NaH (0.027 g, 0.680 mmol, 60% in mineral oil) at 0° C. The reaction was brought to room temperature and stirred for 30 min. 1S-(+)-10-Camphorsulphonyl chloride (0.085 g, 0.340 mmol) was added at 0° C., brought to room temperature over 1 h and stirred for further 1 h. The reaction was quenched with saturated NH$_4$Cl solution (15 mL) followed by water (10 mL), and the product was extracted into ethyl acetate (2×15 mL). The combined ethyl acetate layer was washed with brine (15 mL) and dried (Na$_2$SO$_4$). Solvent was evaporated and crude was purified by column chromatography on silica gel (4% 2 M NH$_3$ in methanol/96% dichloromethane) to obtain compound 9 (0.11 g, 66%) as a solid. $^1$H NMR (DMSO-d$_6$): δ 0.77 (s, 3H), 1.01 (s, 3H), 1.40-1.48 (m, 1H), 1.58-1.67 (m, 1H), 1.77-2.01 (m, 3H), 2.07 (t, 1H, J=4.2 Hz), 2.19-2.39 (s+m, 6H), 2.50-2.64 (m, 2H), 2.67-2.76 (m, 1H), 2.84 (t, 1H, J=8.6 Hz), 3.42-3.63 (m, 3H), 7.45 (s, 1H), 7.55 (dd, 1H, J=1.8, 8.8 Hz), 7.84 (d, 1H, J=8.8 Hz), 8.00 (brs, 1H); MS (ESI+) m/z (%): 493/495 (MH$^+$, 100). The separation of the diastereomeric mixture of compounds was not possible by regular column chromatography.

The same reaction with 1R-(−)-10-camphorsulphonyl chloride did not yield any product. In this case only starting material was recovered.

Example 8

Attempted preparation of 1-(7,7-dimethyl-2-oxobicyclo[2.2.1]heptan-1-yl)-N-(3-(1-methylpyrrolidin-3-yl)-1H-indol-5-yl)methanesulfonamide

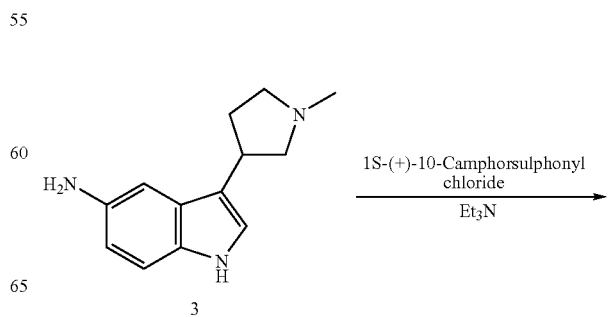

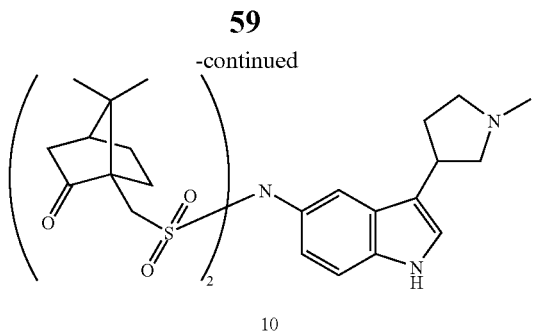

10

11

To a solution of 3-(1-methylpyrrolidin-3-yl)-1H-indol-5-amine, 3 (62 mg, 0.288 mmol) in anhydrous dichloromethane (10 mL) was added triethylamine (72.9 mg, 0.720 mmol), and the mixture briefly cooled in an ice-bath. 1S-(+)-10-Camphorsulphonyl chloride (75.8 mg, 0.302 mmol) was added at 0° C., the reaction brought to room temperature stirred for further 16 h. The reaction was concentrated, and the crude residue purified via chromatography on silica gel (5% methanol/95% dichloromethane to 10% methanol/90% dichloromethane) to yield (bis)sulphonamide 10, and (tris)sulphonamide 11.

Compound 10: 1-(7,7-dimethyl-2-oxobicyclo[2.2.1]heptan-1-yl)-N-((7,7-dimethyl-2-oxobicyclo[2.2.1]heptan-1-yl)methylsulfonyl)-N-(3-(1-methylpyrrolidin-3-yl)-1H-indol-5-yl)methanesulfonamide. MS (ESI+) m/z (%): 644 (MH+, 100), ESI-HRMS calculated for $C_{33}H_{46}N_3O_6S_2$ (MH+) 644.2822; observed: 644.2829.

Compound 11: 1-(7,7-dimethyl-2-oxobicyclo[2.2.1]heptan-1-yl)-N-((7,7-dimethyl-2-oxobicyclo[2.2.1]heptan-1-yl)methylsulfonyl)-N-(1-((7,7-dimethyl-2-oxobicyclo[2.2.1]heptan-1-yl)methylsulfonyl)-3-(1-methylpyrrolidin-3-yl)-1H-indol-5-yl)methanesulfonamide. MS (ESI+) m/z (%): 858 (MH+, 100), ESI-HRMS calculated for $C_{43}H_{60}N_3O_9S_3$ (MH+) 858.3492; observed: 858.3497.

Example 9

3-(1-Methylpyrrolidin-3-yl)-N—((R)-1-phenylethyl)-1H-indol-5-amine (13)

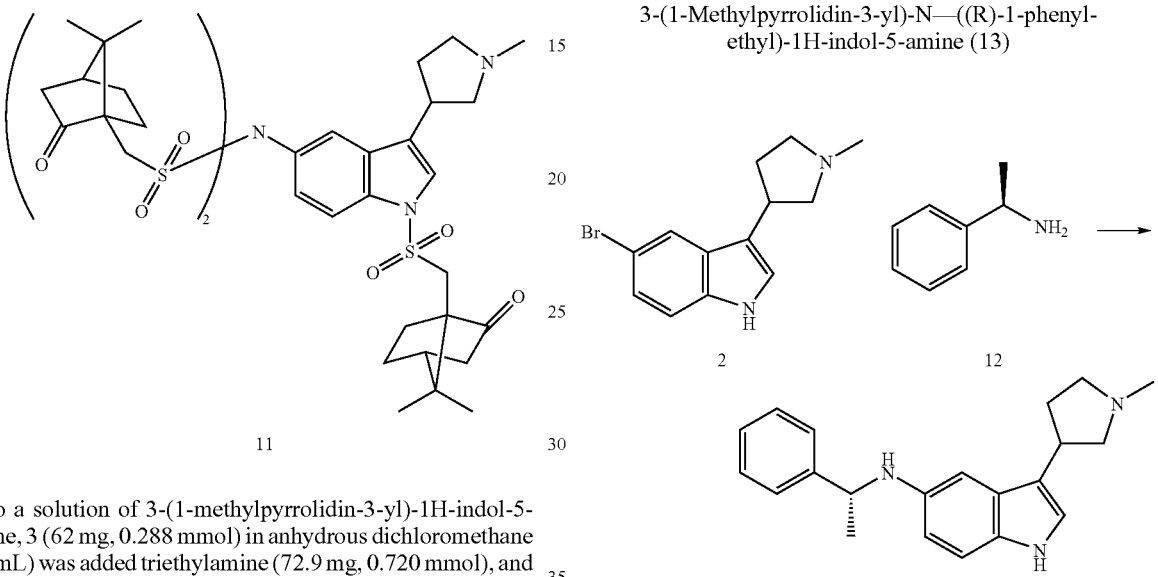

General Procedure:

5-Bromo-3-(1-methylpyrrolidin-3-yl)-1H-indole 2, (100 mg, 0.358 mmol), Tris(dibenzylideneacetone)dipalladium (0), (R)-1-phenylethanamine 12, (52.1 mg, 0.430 mmol, 1.2 equiv.), (±)-BINAP, sodium tert-butoxide, and anhydrous solvent were charged to a 20 mL microwave vial with a magnetic stirbar under an atmosphere of Argon. The vial was sealed and heated in an oil bath as per the conditions outlined in Table 7.

TABLE 7

Attempted cross-coupling with (R)-1-phenylethanamine.

| Palladium source (equiv) | Ligand (equiv) | Solvent | Base (equiv) | Reaction Temp, Time | Results (TLC) |
|---|---|---|---|---|---|
| Pd$_2$dba$_3$ (2 mol %) | BINAP (4 mol %) | Toluene | NaOtBu (1.4 equiv) | 70° C., 21 hrs | Negligible Reaction |
| Pd$_2$dba$_3$ (2 mol %) | BINAP (4 mol %) | Toluene | NaOtBu (3.0 equiv) | 70° C., 21 hrs | Negligible Reaction |
| Pd$_2$dba$_3$ (5 mol %) | BINAP (10 mol %) | Toluene | NaOtBu (2.5 equiv) | 100° C., 21 hrs | Negligible Reaction |
| Pd$_2$dba$_3$ (5 mol %) | BINAP (10 mol %) | Dioxane | NaOtBu (2.5 equiv) | 100° C., 21 hrs | Negligible Reaction |
| Pd$_2$dba$_3$ (5 mol %) | BINAP (10 mol %) | THF | NaOtBu (2.5 equiv) | 65° C., 21 hrs | Negligible Reaction |

Example 10

3-(5-Bromo-1H-indol-3-yl)-1-methylpyrrolidine-2,5-dione (7)

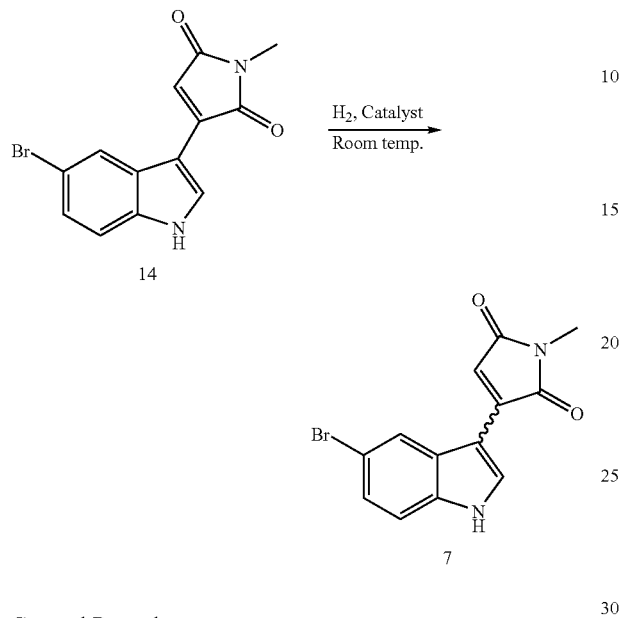

General Procedure:

A solution of 3-(5-bromo-1H-indol-3-yl)-1-methyl-1H-pyrrole-2,5-dione 14, (prepared according to a known method, EP 1 224 932 A1) in the corresponding solvent (as shown in Table 8) was treated with a metal catalyst and ligand at room temperature, and the reaction mixture was stirred at room temperature under an atmosphere of hydrogen as per the conditions outlined in Table 8. The reaction mixture was filtered through silica gel bed, and the solvent was evaporated to obtain crude product. The crude product was purified by flash column chromatography (60% Ethylacetate/40% Hexanes) to yield 3-(5-bromo-1H-indol-3-yl)-1-methylpyrrolidine-2,5-dione (7). The enantiomeric excess was determined with chiral HPLC.

Chiral HPLC Purity Conditions:
Column: ChiralPak AD-H, 4.6×250 mm.
Mobile Phase Hexane/Ethanol/Di ethyl amine (80/20/0.1)
Flow Rate: 1 mL/minute
UV Detection: 254, 230 nm
Sample Preparation: 1 mg/mL in Ethanol.
Injection Volume: 5 μL

Example 11

3-(5-Bromo-1-(tert-butyldimethylsilyl)-1H-indol-3-yl)-1-methylpyrrolidine-2,5-dione (17)

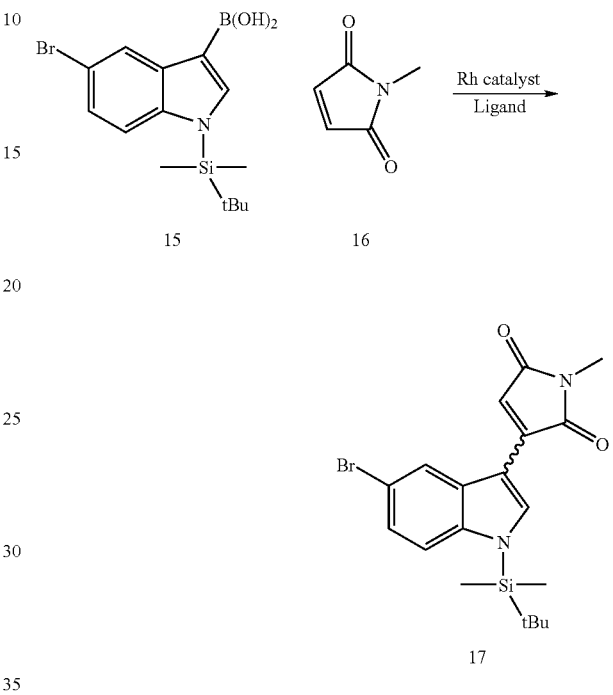

General Procedure:

To an oven dried, argon purged flask fitted with magnetic stir-bar is charged 5-bromo-1-(tert-butyldimethylsilyl)-1H-indol-3-ylboronic acid 15 (141.6 mg, 0.400 mmol), N-Methyl maleimide 16 (22.2 mg, 0.200 mmol), Rhodium catalyst (0.05 equiv.), anhydrous dioxane (1 mL) and stirring begun. $H_2O$ (0.05 mL) added, and mixture heated in an oil bath as per the conditions outlined in Table 9 below. The reaction mixture was filtered through silica gel bed, and the solvent was evaporated to obtain crude product. The crude product was purified via chromatography on silica gel (20% Ethylacetate/80% Hexanes) to yield 3-(5-bromo-1-(tert-butyldimethylsilyl)-1H-indol-3-yl)-1-methylpyrrolidine-2,5-dione 17. The enantiomeric excess was determined with chiral HPLC.

TABLE 8

Asymmetric hydrogenation of 3-(5-bromo-1H-indol-3-yl)-1-methyl-1H-pyrrole-2,5-dione, 14

| Metal precursor | Ligand | Solvent | $H_2$ pressure | Reaction Time | Result |
| --- | --- | --- | --- | --- | --- |
| Rh(COD)$_2$OTf | (R,R)-MeDuphos | MeOH/THF | balloon | 5 days | No reaction |
| Rh(COD)$_2$OTf | (R,R)-MeDuphos | MeOH/THF | 40 psi | 17.5 hr | Product obtained, 0% ee |
| Rh(COD)$_2$OTf | (R,R)-Me-BPE | MeOH/THF | 40-60 psi | 24 hr | No reaction |
| Rh(COD)$_2$OTf | (R)-Phanephos | MeOH | 80-100 psi | 32 hr | No reaction |
| (R)-Binaphane-Rh(COD)BF$_4$ | | MeOH/THF | 80 psi | 24 hr | No reaction |
| RuClphosphine ligand | | MeOH/THF | 80 psi | 24 hr | No reaction |

TABLE 9

Asymmetric 1,4 addition to N-Methyl maleimide 16.

| Rhodium Catalyst | Reaction Temp. | Time | Result |
|---|---|---|---|
| Rh(COD)$_2$BF$_4$ | 40° C. | .5 hrs | Negligible reaction, mainly s.material 15 (TLC) |
| Rh(COD)$_2$BF$_4$ | 45° C. | 16 hrs | Protodeborination |
| Rh(COD)$_2$BF$_4$ | 70° C. | 2.5 hrs | Isolate yield 23% |
| Rh(COD)$_2$OTf | 45° C. | 2 hrs | Isolated yield 65% |
| Rh(COD)(C$_{16}$H$_{24}$O$_3$P$_2$)BF$_4$ | 70° C. | 1 hr | Isolated yield 60%, 0% ee |
| Rh(COD)(C$_5$H$_5$(C$_7$H$_{14}$P)$_2$Fe)BF$_4$ | 70° C. | 1 hr | Isolated yield 45%, 0% ee |
| (R)-Binaphane-Rh(COD)BF$_4$ | 70° C. | 1.5 hrs | Isolated yield 45%, 0% ee |

Example 12 nNOS (Human), eNOS (Human) Enzyme Assay

Human nNOS and eNOS Protocol:
Reagents and Materials

| | |
|---|---|
| Enzymes: | Nitric oxide synthase (neuronal, human recombinant) nNOS I, Cat. No. ALX-201-068, Axxora LLC, CA 92121, USA; Nitric oxide synthase (endothelial, human recombinant) eNOS III, Cat. No. ALX-201-070, Axxora LLC |
| L-NMMA | N$^G$-monomethyl-L-arginine 1/04/05, Cat # A17933, Novabiochem |
| L-NAME | N$^G$-Nitro-L-arginine methyl ester Cat # N5751, Aldrich |
| 2× Reaction Buffer: | 50 mM Tris-HCl (pH 7.4), Cat. No. 93313, Sigma-Aldrich Co., St. Louis, MO |
| | 6 µM tetrahydrobiopterin (BH$_4$), Cat. No. T4425, Sigma |
| | 2 µM flavin adenine dinucleotide (FAD), Cat. No. F6625, Sigma |
| | 2 µM flavin adenine mononucleotide (FMN), Cat. No. F8399, Sigma |
| Stop Buffer: | 50 mM N-2-hydroxyethylpiperazine-N'-2-ethanesulfonic acid; (HEPES) (pH 5.5), H7523, Sigma and 5 mM Ethylene diamine tetra acetic acid (EDTA), Cat. No. EDS, Sigma |
| NADPH: | 10 mM freshly prepared on day of assay, Cat. No. N7505, Sigma |
| Calcium Chloride: | 6 mM, Cat. No. 21107, Sigma |
| Calmodulin: | 1 mM, Cat. No. P2277, Sigma |
| [$^3$H]-L-Arginine: | 1 µCi/reaction, 40-70 Ci/mmol, Cat. No. TRK-698, Amersham Biosciences |
| L-Arginine: | 2.5 µM (final assay concentration), Cat. No. A5131, Sigma |
| Equilibrated Resin: | AG-50W X8 Resin in HEPES buffer (pH 5.5), Cat. No. 1421441, Bio-Rad Laboratories Ltd. |
| Spin Cups & Holder: | Cat. No. C8163, Fisher Scientific |
| Liquid Scintillation Counter: | Tri-Carb 2000CA/LL, Canberra Packard Canada. |
| Liquid Scintillation Fluid: | Cat. No. 6012239, Ultima Gold, Perkin-Elmer Life and Analytical Sciences, MA |
| CO$_2$ Incubator: | Lab-Line Enviro Shaker. |
| Microcentrifuge: | Mikro 20. |
| Vortex Mixer: | Mini Vortex mixer, IKA |

Procedure for Human nNOS and eNOS

Primary stock solutions of test compounds at a concentration of 6 mM are prepared. The primary stock solutions of each test compound are prepared freshly in distilled water on the day of study. For determination of IC$_{50}$ values, 12 test compound concentrations are prepared as 3-fold serial dilutions. Concentration range of test compound utilized for nNOS are 0.001 to 300 µM and for eNOS are 0.003 to 1000 µM. The vehicle of the test compound or inhibitor is used as blank control. For non-specific activity, 100 µM L-NMMA is used. The IC$_{50}$ concentration of L-NAME was run in parallel as a control.

All incubations are performed in duplicate:

Prepare the reaction mixture on ice by adding the following components with a micropipette to a polypropylene microcentrifuge tube:

10 µL of test compound, inhibitor or control (vehicle or L-NMMA) solution
25 µL of Reaction Buffer {25 mM Tris-HCl, 0.6 µM BH4, -continued 0.2 µM FMN, 0.2 µM FAD}
5 µL of 10 mM NADPH solution {1 mM} (freshly prepared in 10 mM Tris-HCl (pH 7.4)
5 µL of 6 mM CaCl$_2$ {600 µM}
5 µL of 1 mM Calmodulin {100 µM}
5 µL of 0.02 µg/µL nNOS or 0.12 µg/µL eNOS Pre-incubate the above reaction mixture at room temperature for 15 mins.

Start the reaction by addition of the substrate (in 5 µL containing 1 µCi of [$^3$H]-L-Arginine+2.5 µM of unlabeled L-Arginine) to the reaction mixture. Total reaction volume is 60 µL.

Mix using a vortex mixer and incubate the above reaction mixture at 37° C. in an incubator for 30 minutes.

Add 400 µL of ice-cold Stop Buffer at the end of the incubation period to stop the reaction. (The EDTA in the Stop Buffer chelates all of the available calcium.)

Mix using a vortex mixer and transfer the reaction samples to spin cups and centrifuge using a microcentrifuge, at 13,000 rpm for 30 sec. at room temperature.

Remove the spin cups from the holder and transfer 450 μL of eluate (containing the unbound L-citrulline) to scintillation vials. Add 3 mL of scintillation fluid and quantify the radioactivity in a liquid scintillation counter.

Calculation of $IC_{50}$ Values:

Data is analyzed using a Sigmoidal dose-response (variable slope) curve to determine the $IC_{50}$ value of the test compound.

$$Y=\text{Bottom}+(\text{Top}-\text{Bottom})/(1+10^{((\text{Log } IC_{50}-X)*\text{Hill Slope})})$$

X is the logarithm of test compound or inhibitor concentration

Y is the amount of L-citrulline formation (pmol)

Bottom refers to the lowest Y value and Top refers to the highest Y value.

This is identical the "four parameter logistic equation."

The slope factor (also called Hill slope) describes the steepness of a curve. A standard competitive binding curve that follows the law of mass action has a slope of −1.0. If the slope is shallower, the slope factor will be a negative fraction, e.g., −0.85 or −0.60.

Human iNOS Assay:

iNOS activity was determined by measuring the conversion of [$^3$H]L-arginine to [$^3$H]L-citrulline by radiometric method. Recombinant human inducible NOS (iNOS) was produced in Baculovirus-infected Sf9 cells (ALEXIS). To measure constitutive isoforms NOS, 10 μL of enzyme is added to 100 μL of 40 mM HEPES, pH=7.4, containing 2.4 mM $CaCl_2$, 1 mM $MgCl_2$, 1 mg/ml BSA, 1 mM EDTA, 1 mM dithiotheitol, 1 μM FMN, 1 μM FAD, 10 μM tetrahydrobiopterin, 1 mM NADPH, 1.2 μM CaM.

1. 15 μL of test substances are added to the mixture with the specific enzyme and pre-incubated at RT for 15 min.
2. The reaction was initiated by addition of 20 μL-arginine containing 0.25 μCi of [$^3$H] arginine/ml and 24 μM L-arginine.
3. The incubation is carried out at 37° C. for 45 min.
4. The reaction is stopped by adding 20 μL of ice-cold buffer containing 100 mM HEPES, 3 mM EGTA, 3 mM EDTA, pH=5.5.
5. [$^3$H]L-citrulline is separated by DOWEX (ion-exchange resin DOWEX 50 W X 8-400, SIGMA).
6. The DOWEX is removed by spinning at 12,000 g for 10 min in the centrifuge.
7. An aliquot 70 μL of the supernatant is added to 100 μL scintillation fluid.
8. The samples are counted in a liquid scintillation counter (1450 Microbeta Jet, Wallac).

Specific NOS activity is reported as the difference between the activity (total) and that in the presence of the inhibitor L-NMMA (non-specific) in the final concentration 240 μM. The total volume of the reaction mixture is 150 μL in every well. All assays are performed at least in duplicate. Standard deviations are 10% or less. Results for exemplary compounds of the invention are shown in Table 10. These results again show the selectivity of the compounds of the invention for nNOS inhibition versus e or iNOS.

TABLE 10

Selective inhibition of human NOS by compounds of the Invention

| Compound | nNOSh (uM) | eNOSh (uM) | e/n | iNOSh (uM) |
|---|---|---|---|---|
| 6 | 0.4 | 38.7 | 97 | 35 |
| 6a | 0.68 | 45.5 | 67 | 25 |
| 6b | 0.205 | 20.6 | 100 | 20 |
| 18 | 0.92 | 51.1 | 55 | 20 |
| Sumatriptan | — | — | — | — |
| L-NMMA | 0.7 | 0.5 | 0.7 | — |

Example 13

Serotonin 5HT1D/1B Binding Assays

5-HT1D binding assays (agonist radioligand) were performed using bovine caudate membranes according to the methods of Heuring and Peroutka (*J. Neurosci.*, 7: 894-903 (1987)). 5-HT1B (rat cerebral cortex) binding assays (agonist radioligand) were performed according to the method of Hoyer et. al. (*Eur. J. Pharmacol.*, 118: 1-12 (1995)). For the purpose of result analysis, the specific ligand binding to the receptors is defined as the difference between the total binding and the nonspecific binding as determined in the presence of an excess of unlabelled ligand. The results are expressed as a percent of control specific binding obtained in the presence of the test compounds. $IC_{50}$ values (concentration causing a half-maximal inhibition of control specific binding) and Hill coefficients ($n_H$) were determined by non-linear regression analysis of the competition curves using Hill equation curve fitting and the inhibition constants ($K_i$) were calculated from the Cheng Prusoff equation ($K_i=IC_{50}/(1+(L/K_D))$), where L=concentration of radioligand in the assay, and $K_D$=affinity of the radioligand for the receptor). Results for the binding of selected compounds in 5HT1D and 1B are shown in Table 11.

TABLE 11

Binding of Compounds in bovine 1D and rat 1B receptors.

| Compound | 5HT1D (uM) | 5HT1B (uM) |
|---|---|---|
| 6 | 0.19 | 0.85 |
| 6a | 0.17 | 1.4 |
| 6b | 0.079 | 0.705 |
| 18 | 0.051 | 0.16 |
| Sumatriptan | 0.059 | 0.11 |
| L-NMMA | — | — |

Example 14

Human Liver Microsome In Vitro Metabolism Assays of Enantiomers 6a, 6b, and 18

General

The compounds (10 μM) were incubated with pooled human liver microsomes in the presence and absence of the co-factor, β-Nicotinamide adenine dinucleotide phosphate ($NADP^+$), required for oxidative metabolism by the Cytochrome P-450 (CYP) and flavin containing monooxygenase (FMO) enzymes. A tandem liquid chromatography mass spectrometry (LC-MS/MS) method was developed and/or qualified for each compound for measuring relative stability of 6a, 6b, and 18 in the terminated reaction mixtures. The relative disappearance of the test compounds following 15, 30, and 60 min of incubation with liver microsomes, NADP$^+$, and an NADPH-regenerating system was determined in duplicate samples. 6a, 6b, and 18 stability following 0 and 60 min of incubation with liver microsomes in the absence of NADP$^+$ was also determined. The metabolic stability of clozapine (10 µM) was determined in parallel as a positive control.

A 1 mM stock solution of each test compound was freshly prepared in distilled water on the day of the assay. The stock solutions were used for the metabolic stability assay as well as for preparation of calibration standards.

Reagents and Standards
1. Human Liver Microsomes (Pooled Mixed Gender, Cat. No. 452161, BD Gentest)
2. 0.5 M Potassium Phosphate Buffer, pH 7.4: prepared with 150 mL 0.5 M Potassium Phosphate monobasic (Cat No. P0662, Sigma Aldrich Co.) and 700 mL 0.5 M Potassium Phosphate dibasic (Cat No. P8281, Sigma Aldrich Co.).
3. 67 mM Potassium Phosphate Buffer, pH 7.4: prepared from a 0.5 M Potassium Phosphate Buffer pH 7.4 stock solution
4. Methanol (Cat No. MX0480-1, EMD)
5. Magnesium Chloride Hexahydrate ($MgCl_2$, Cat No. M0250, Sigma Aldrich Co.)
6. Distilled water (Cat No. 15230-162, Invitrogen Corp.)
7. NADP$^+$ (Cat. No. N0505, Sigma Aldrich Co.)
8. Glucose-6-phosphate (G6P, Cat. No. G7250, Sigma Aldrich Co.)
9. Glucose-6-phosphate dehydrogenase (G6PDH, Cat. No. G7877, Sigma Aldrich Co.)
10. Clozapine (Cat. No. C6305, Sigma Aldrich Co.)
11. Mianserin (4486B, Cat. No. 153619, ICN)

Equipment and Supplies
1. Microcentrifuge (Mikro20, Hettich)
2. Orbital shaker/incubator (Lab-Line Enviro Shaker)
3. 24-Well BD cluster plates (Cat No. 351147, VWR International)
4. 1.5 mL microcentrifuge tubes (Cat No. L-510-GRD, Rose Scientific Ltd.)
5. 15 mL Falcon tubes (Cat No. 35-2096, VWR International)
6. 50 mL Falcon tubes (Cat No. 21008-178, VWR International)

Bioanalysis
Bioanalytical Method Development and Qualification for the Test Compounds Method development and sample analysis was conducted using a PE Sciex API 4000 LC-MS/MS system equipped with an Agilent LC system with a binary pump, and solvent degasser, a suitable LC autosampler, as well as a divert valve (VIVI, Valco Instrument Co. Inc.) installed between the column and mass spectrometer inlet. Method qualification for each test compound included: the determination of the ion transition for the compound and the internal standard (i.e., identification of the parent and daughter ions), determination of the linear dynamic range, using 5 calibration standards in duplicate, intra-batch precision and accuracy and system check reproducibility (±20%) using neat compound.

Clozapine was used as an internal standard (IS) for the test compounds. The concentration of IS was 0.570 ng/mL for 6a, and 1.14 ng/mL for 6b. A detailed summary of the bioanalytical method for the analytes is included below.

Sample Analysis of 6a, 6b and 18*
*This compound was analyzed in a separate experiment in a similar fashion to 6a and 6b Samples for each test compound generated from the assay were analyzed as one batch by the qualified LC-MS/MS method. The sample batch consisted of the following: initial system check standards (three replicates), the assay samples (in duplicate) and the final system check standards (three replicates). A batch was considered acceptable if the system check injection acceptance criteria described above was met. Individual results for the % remaining following incubation with the test compounds were determined by comparing peak are ratios (analyte/internal standard) at each time point to the 0 hour (100% stable) value obtained.

Sample Analysis of Clozapine

Samples generated for clozapine from the human liver microsomal stability assays were analyzed by a validated LC-MS/MS method.

Metabolic Stability Assay
Human Liver Microsomes

The study was conducted with cryopreserved human liver microsomes, pooled from 15 donors (mixed pool of male and female donors). Pooled donor microsomes were used in order to represent an "average" metabolic activity. The microsomes have been characterized by the supplier for Phase I (CYP1A2, CYP2A6, CYP2B6, CYP2C8, CYP2C9, CYP2C19, CYP2D6, CYP2E1, CYP3A4, CYP4A11 and FMO) and Phase II (UGT1A1, UGT1A4 and UGT1A9) enzymatic activity.

Stability Assay
1. The assay was performed with 0.5 mg/mL human liver microsomes in 50 mM potassium phosphate buffer, pH 7.4 (PPB), and in the presence of an NADPH regenerating system (1.3 mM NADP$^+$, 3.3 mM glucose-6-phosphate, 0.4 U/mL glucose-6-phosphate dehydrogenase) and 3.3 mM $MgCl_2$. All incubations were performed in duplicate. One concentration of test compound was tested (10 µM).
2. A stock solution of microsomes (20 mg/mL) was thawed in a 37° C. water bath on the day of the assay and then immediately placed on ice. The microsomes were then diluted with an appropriate volume of PPB, such that the final protein concentration in the assay was 0.5 mg/mL, and the final PPB concentration was 50 mM.
3. An appropriate aliquot of the 1 mM stock solution of the test compounds (in water) was added to the diluted microsomes, and then the mixture was warmed to 37° C. for 5 min in an incubator. Two 75 µL aliquots of this warmed solution were added to chilled labeled polypropylene centrifuge tubes containing 100 µL of the appropriate ice cold internal standard solution in methanol and 25 µL of a 4-fold concentrated solution of the NADPH regenerating system (5.2 mM NADP$^+$, 13.2 mM glucose-6-phosphate, 1.6 U/mL glucose-6-phosphate dehydrogenase) and 13.2 mM $MgCl_2$. These samples represent the time zero samples.
4. An aliquot (375 µL) of the pre-warmed liver microsomes and test compound mixture was dispensed into a well of a 24-well plate. A 125 µL aliquot of pre-warmed (37° C. for 5 min) 4-fold concentrated NADPH regenerating system solution was then added to start the reaction. Reaction mixtures (0.5 mL) were incubated in a shaking incubator (150 rpm) at 37° C.
5. One hundred µL of the reaction mixture was sampled following 15, 30, and 60 min of incubation. Each sample with test compound was immediately added to a chilled labeled centrifuge tube containing 100 µL of ice cold methanol to terminate the reaction.
6. All samples were mixed by vortex and then centrifuged (15,000×g for 10 min at 4° C.) to pellet the protein. An aliquot of the supernatant from each sample was then transferred to a clean, labeled centrifuge tube and stored at −70° C. until bioanalysis.

7. The metabolic stability of clozapine (10 μM) was similarly monitored in parallel.

8. As a control, test compound was incubated with microsomes in the absence of NADP+. One hundred μL of the reaction mixture was sampled for control samples following 0 and 60 min of incubation as detailed above.

9. Data sheets with the date of the experiment, the Study No., the compound IDs, the sampling times, a plate map and any deviations to the protocol were recorded.

The data were analyzed by nonlinear regression analysis (GraphPad Prism software, Version 3.02) by curve fitting to the following equation for mono-exponential decay:

$$\% R_t = \% R_o e^{-kt}$$

where $\% R_t$ represents the % remaining at time t, $\% R_o$ denotes the initial percentage of the parent compound in the incubation mixture (i.e., at time zero), and k represents the rate constant for the decay. No weighting was used in the regression analysis. The half-life ($t_{1/2}$) for compound disappearance, where appropriate, was calculated as 0.693/k.

| Bioanalytical Method for 6a and 6b | |
|---|---|
| Analyte ID | 6a, 6b |
| Calibration Range | n/a (No standard curve. Using the ratio of compound/IS to compare change of concentration) |
| Internal Standard ID | Clozapine |
| Matrix | HLM |
| HPLC | Agilent 1100 Liquid Chromatograph with vacuum degasser (Model No. G1322A), quaternary pump (Model No. G1311A) and well plate auto-sampler (Model No. G1367A) |
| Injection Volume | 6b-10 μL, 6a-10 μL and Cloz-2.0 μL |
| Analytical Column | Onyx Momolithic C-18, 100 × 3.0 mm, Cat.# 051020-10, Phenomenex. Column #: 30 |
| Inline Filter | 0.5 μm (Cat. No. A-428, Upchurch Scientific) |
| Column Temperature | Ambient |
| Mobile Phase | A = 95% water with 10 mM AmF, pH3 (v/v) and 5% methanol. B = 95% methanol and 5% water with 10 mM AmF, pH3 (v/v) 80% B and 20% A |
| Flow Rate | 1.0 mL/min |
| Run Mode | Isocratic Elution |
| Needle Wash | 50% MeOH in water |
| Analysis Time | 1 min |
| Switching Valve | VICI, Model No. EHMA (Valco Instrument Co. Inc.) 0 to 0.2 min, column effluent diverted to waste 0.2 to 0.9 min, column effluent flows to mass spectrometer 0.9 to 1.0 min, column effluent diverted to waste |
| Detector | API 4000 LC-MS/MS System (Applied Biosystems/MDS Sciex) |
| Interface | APCI |
| Polarity (Mode) | Positive Ion Multiple Reaction Monitoring (MRM) |
| Curtain Gas | 40psig for all of analytes. |
| Ion Source Gas 1 | 65 psig for all of analytes. |
| Interface Temperature | 500° C. |
| Interface Heater | ON |
| Nebulizer Current | 5 uA |
| Dwell Time | 150 ms |
| Probe Position | X = 5, Y = 3 |
| Collision Activity | |
| Dissociation (CAD) Gas | 6 psig for all of analytes. |
| Declustering Potential | 100 V for all of analytes |
| Entrance Potential | 10 V for all of analytes |
| Collision Energy | 30 V for clozapine and 40 V for all of analytes. |
| Collision Cell Exit Potential | 15 V for all of analytes. |

Preparation of Blank Simulated Matrix

Ten mL of simulated blank matrix for use in the bioanalysis (preparation of calibration standards and QC samples) was prepared without microsomal protein as follows:

1. 1.25 mL of the 4-fold concentrated solution of the NADPH regenerating system was added to 0.05 mL of water and 3.70 mL of potassium phosphate buffer, pH 7.4 (50 mM final concentration) and mixed thoroughly by vortex.

2. Five mL of ice cold methanol was then added, and the mixture was again mixed by vortex. The simulated matrix was stored at −70° C. until use.

Calculations and Expression of Results

The mean of the test compound to the internal standard peak area ratios were calculated for the zero time sample. The duplicate peak area ratios following 15, 30, and 60 minutes of incubation, were individually compared to the mean zero time sample, and expressed as % remaining after 15, 30, and 60 minutes.

TABLE 12a

Summary of Analyte Ion Transitions and Retention Times.

| Analyte ID | Molecular Formula | Exact Mass (g/mol) | Ion Transitions (m/z) | | Retention Time (min) |
|---|---|---|---|---|---|
| | | | Precursor Ion | Product Ion | |
| Clozapine | $C_{18}H_{19}N_4Cl$ | 326.8 | 327.3 | 270.0 | 0.66-0.68 |
| 6a | $C_{18}H_{20}N_4S$ | 324.443 | 325.1 | 225.0 | 0.56-0.58 |
| 6b | $C_{18}H_{20}N_4S$ | 324.443 | 325.1 | 225.0 | 0.56-0.58 | m/z represents the mass to charge ratio

| SUMMARY OF THE LC-MS/MS METHOD FOR CLOZAPINE | |
|---|---|
| Analyte ID | Clozapine |
| Calibration Range | 0.010-6.00 µM |
| Matrix | Terminated human liver microsome reaction mixture |
| Internal Standard (IS) ID | Mianserin (250 ng/mL) |
| HPLC | Agilent 1100 Liquid Chromatograph with vacuum degasser (Model No. G1322A), binary pump (Model No. G1312A) and well plate autosampler (Model No. G1367A) |
| Injection Volume | 2.0 µL |
| Analytical Column | Discovery HS F5, 2.1 × 50 mm, 3.0 µm (Cat. No. 567500-U, Supelco) |
| Inline Filter | 0.5 µm (Cat. No. A-428, Upchurch Scientific) |
| Column Temperature | Ambient |
| Mobile Phase | 60% methanol and 40% water with 10 mM ammonium formate, pH 3.0 |
| Flow Rate | 0.5 mL/min |
| Run Mode | Isocratic |
| Needle Wash | Solvent: mobile phase<br>Wash time: 1 s |
| Analysis Time | 6.0 min |
| Switching Valve | VICI (Model No. EHMA, Valco Instrument Co. Inc.)<br>0 to 2.8 min, column effluent diverted to waste<br>2.9 to 5.8 min, column effluent flows to mass spectrometer<br>5.9 to 6.0 min, column effluent diverted to waste |
| Detector | API 4000 LC-MS/MS System (Applied Biosystems/MDS Sciex) |
| Interface | APCI |
| Polarity (Mode) | Positive Ion Multiple Reaction Monitoring (MRM) |
| Curtain Gas | 45 psig, Nitrogen |
| Ion Source Gas 1 | 65 psig, Nitrogen |
| Interface Temperature | 500° C. |
| Interface Heater | ON |
| Nebulizer Current | 1 µA |
| Dwell Time | 500 ms |
| Probe Position | X = 5, Y = 3 |
| Collision Activity | |
| Dissociation (CAD) Gas | 6 psig |
| Declustering Potential | 100 V for both analyte and IS |
| Entrance Potential | 10 V for both analyte and IS |
| Collision Energy | 30 V for both analyte and IS |
| Collision Cell Exit Potential | 15 V for analyte, 6 V for IS |

TABLE 12b

Summary of Analyte Ion Transitions and Retention Times.

| | | | Ion Transitions | | |
|---|---|---|---|---|---|
| Analyte ID | Molecular Formula | Formula Weight (g/mol) | Precursor Ion (m/z) | Product Ion (m/z) | Retention Time (min) |
| Clozapine | $C_{18}H_{19}N_4Cl$ | 326.8 | 327.3 | 270.0 | 4.07-4.32 |
| Mianserin | $C_{18}H_{20}N_2$ | 264.4 | 265.1 | 208.5 | 2.98-3.19 | m/z represents the mass to charge ratio

Results and Discussion

Bioanalytical Method Qualification and Sample Analysis

A detailed summary of the bioanalytical method for qualification of the test compounds in terminated microsomal reaction mixtures is included above. Results from the sample analyses are included in Table 13a. All acceptance criteria were met for both the method qualification and for analysis of the samples.

Metabolic Stability

The mean concentrations of clozapine and of the test compounds (6a and 6b) as a function of incubation time are summarized in Table 12c. The data (expressed as % remaining versus incubation time) are depicted in the Figures described below. Clozapine was used as a positive control as it has been demonstrated to be well absorbed (90-95%) in humans following oral dosing, but is subject to first-pass metabolism resulting in an absolute bioavailability of 50 to 60%. Clozapine is also known to be metabolized primarily to N-desmethyl clozapine and clozapine N-oxide, with several CYP subtypes implicated in their formation.

The disappearance of clozapine upon incubation with human liver microsomes was NADPH-dependent (Table 12c). The estimated half-life for clozapine disappearance from the microsomal reaction mixture was 354 min, indicating that the microsomes were metabolically active. The test compound 6b (FIG. 1) and 18 (FIG. 2) were metabolically stable over 60 min of incubation, indicating that these compounds are not substrates for oxidative metabolism by the CYP or FMO enzymes. The estimated half-life of 6a was 132 min (FIG. 1). The data indicate a significant difference in the metabolic stability of the two enantiomers. This shorter half life may contribute to the observed differences in efficacy of 6a versus 6b in the animal model of pancreatitis (See example 16).

TABLE 12c

Mean test compound peak area ratios, determined in duplicate, as a function of incubation time in human liver microsomes incubated in the presence and absence of $NADP^+$.

| Compound ID | Presence of co-factor ($\pm NADP^+$) | Peak Area Ratio[a] | | | |
|---|---|---|---|---|---|
| | | 0 min | 15 min | 30 min | 60 min |
| 18 | $+NADP^+$ | 5.17 | 4.99 | 5.00 | 5.23 |
| | $-NADP^+$ | 5.65 | n/a | n/a | 5.12 |
| 6a | $+NADP^+$ | 25.8 | 25.8 | 23.7 | 19.4 |
| | $-NADP^+$ | 22.0 | | | 20.2 |

TABLE 12c-continued

Mean test compound peak area ratios, determined in duplicate, as a function of incubation time in human liver microsomes incubated in the presence and absence of NADP$^+$.

| Compound ID | Presence of co-factor (±NADP$^+$) | Peak Area Ratio[a] | | | |
|---|---|---|---|---|---|
| | | 0 min | 15 min | 30 min | 60 min |
| 6b | +NADP$^+$ | 20.6 | 20.5 | 21.4 | 20.5 |
| | −NADP$^+$ | 20.2 | | | 20.6 |
| Clozapine | +NADP$^+$ | 9.25 | 8.81 | 8.91 | 8.19 |
| | −NADP$^+$ | 8.70 | | | 8.79 |

[a] Peak area ratio is the ratio of the peak response of the test compound relative to the peak response of the internal standard

Example 15

Efficacy in Models Predictive of Neuropathic-Like Pain States for 6a and 6b

The efficacy of the compounds of the invention for the treatment of neuropathic pain was assessed using standard animal models predictive of anti-hyperalgesic and anti-allodynic activity induced by a variety of methods, each described in more detail below.

(a) Chung Model of Injury-induced Neuropathic-like Pain: The experimental designs for the Chung Spinal Nerve Ligation SNL Model assay for neuropathic pain are depicted in the Figure below. Nerve ligation injury was performed according to the method described by Kim and Chung (Kim and Chung, *Pain* 50:355-363, 1992). This technique produces signs of neuropathic dysesthesias, including tactile allodynia, thermal hyperalgesia, and guarding of the affected paw. Rats were anesthetized with halothane, and the vertebrae over the L4 to S2 region were exposed. The L5 and L6 spinal nerves were exposed, carefully isolated, and tightly ligated with 4-0 silk suture distal to the DRG. After ensuring homeostatic stability, the wounds were sutured, and the animals allowed to recover in individual cages. Sham-operated rats were prepared in an identical fashion except that the L5/L6 spinal nerves were not ligated. Any rats exhibiting signs of motor deficiency were euthanized. After a period of recovery following the surgical intervention, rats show enhanced sensitivity to painful and normally non-painful stimuli.

After one standard dose (30 mg/kg) injected IP according to the published procedure, there is a clear antihyperalgesic effect of a 5HT$_{1D/1B}$/nNOS selective compounds 6b (see FIG. 3), but only weakly for 6a (see FIG. 4). Administration of compounds 6b but not 6a to test animals also resulted in a reversal of tactile hyperthesia (see FIGS. 5 and 6, respectively). A clear difference between the two enantiomers of compound 6 was observed in this model of neuropathic pain.

Example 16

Experimental Animal Models of Visceral Pain

Animals

Adult male Sprague Dawley rats (Harlan, Indianapolis, Ind.), weighing 150-200 g were maintained in a climate-controlled room with ad lib food and water on a 12-h light/dark cycle (lights on at 07:00 hours). All procedures followed the policies of the International Association for the Study of Pain and the NIH guidelines for the handling and use of laboratory animals. Studies were approved by the University of Arizona IACUC.

Experimental Design:

Visceral Pain Models

Pancreatitis was produced by a tail vein injection of dibutyltin dichloride (DBTC, Aldrich, Milwaukee, Wis., 0.25 cc) dissolved in 100% ethanol at a dose of 8 mg/kg under isofluorane anesthesia (2-3 liters/min, 4.0%/vol until anesthetized, then 2.5%/vol throughout the procedure) (Vera-Portocarrero et al., 2006). Control animals were injected with the vehicle solution only (100% ethanol, 0.25 cc).

Colonic hypersensitivity was induced by enemas of a sodium butyrate solution (1000 mM) twice daily for 3 days (Bourdu et al., 2005). For each enema, a catheter made of P100 polyethylene tube was placed into the colon at 7 cm from the anal opening, and the animals received 1 mL of sodium butyrate at neutral pH. Care was taken to avoid damage of the colonic wall by insertion of the catheter.

Behavioral Measures

Referred abdominal hypersensitivity in the pancreatitis model was quantified by measuring the number of withdrawals events evoked by application of a calibrated von Frey filament (determined by either abdominal withdrawal, licking of the abdominal area, or whole body withdrawal). Rats were placed inside Plexiglas boxes on an elevated fine fiberglass screen mesh and acclimated for 30 minutes before testing. A 4 g von Frey filament was applied from underneath through the mesh floor, to the abdominal area at different points on the surface. A single trial consisted of 10 applications of this filament applied once every 10 seconds to allow the animals to cease any response and return to a relatively inactive position. The mean occurrence of withdrawal events in each trial is expressed as the number of responses to 10 applications as previously described (Vera-Portocarrero et al., 2003).

Referred lumbar hypersensitivity in the colonic hypersensitivity model was quantified by applying von Frey hairs to the lumbar dermatomes of rats (Bourdu et al., 2005). Rats were shaved on the lumbar dermatomes before any manipulation and acclimated inside Plexiglas boxes for 30 minutes on the day of testing. Calibrated von Frey hairs of increasing diameter were applied 5 times for 1 second, ranging from 0.04 to 6 g. The mechanical threshold corresponded to the force in grams of the von Frey hair which induced lumbar skin wrinkling followed or not by escape behavior from the filament.

Statistical Procedures

Significant differences between each experimental group for the behavioral test across time were detected by a two-factor ANOVA follow by the Fishers Least Significance Difference post-hoc test. One-factor ANOVA was used to detect significant differences in behavioral outcomes within each experimental group over time. A linear regression analysis was used to detect the dose-dependency of the effects. Significance was established at the $p<0.05$ level.

Reference List

Bourdu S, Dapoigny M, Chapuy E, Artigue F, Vasson M P, Dechelotte P, Bommelaer G, Eschalier A, Ardid D. Rectal instillation of butyrate provides a novel clinically relevant model of noninflammatory colonic hypersensitivity in rats. *Gastroenterology* 2005; 128:1996-2008.

Vera-Portocarrero L P, Xie J Y, Kowal J, Ossipov M H, King T, Porreca F. Descending facilitation from the rostral ventromedial medulla maintains visceral pain in rats with experimental pancreatitis. *Gastroenterology* 2006; 130: 2155-2164.

Sparmann G, Merkord J, Jaschke A, Nizze H, Jonas L, Lohr M, Liebe S, Emmrich J. Pancreatic fibrosis in experimental pancreatitis induced by dibutyltin dichloride. *Gastroenterology* 1997; 112:1664-1672.

Results of Animal Models Tests for 18, 6a, and 6b.

FIGS. 8 and 10 show the effects of 18 in pancreatitis and IBS models of visceral pain while FIGS. 9 and 11 show the effects of the enantiomer 6b in an experimental model of pancreatitis. Note that the enantiomer 6a does not reverse tactile allodynia in rats with experimental pancreatitis indicating that a compound with nNOS inhibitory activity and 5HT1B/1D activity is preferred for visceral pain (FIG. 11). Both of these compounds reverse the tactile allodynia associated with the two types of insults. Thus it is expected that compounds of the invention would be useful for the treatment of visceral pain.

Example 17

Synthesis of N-(3-(1-ethyl-1,2,3,6-tetrahydropyridin-4-yl)-1H-indol-5-yl)thiophene-2-carboximidamide (Compound 19)

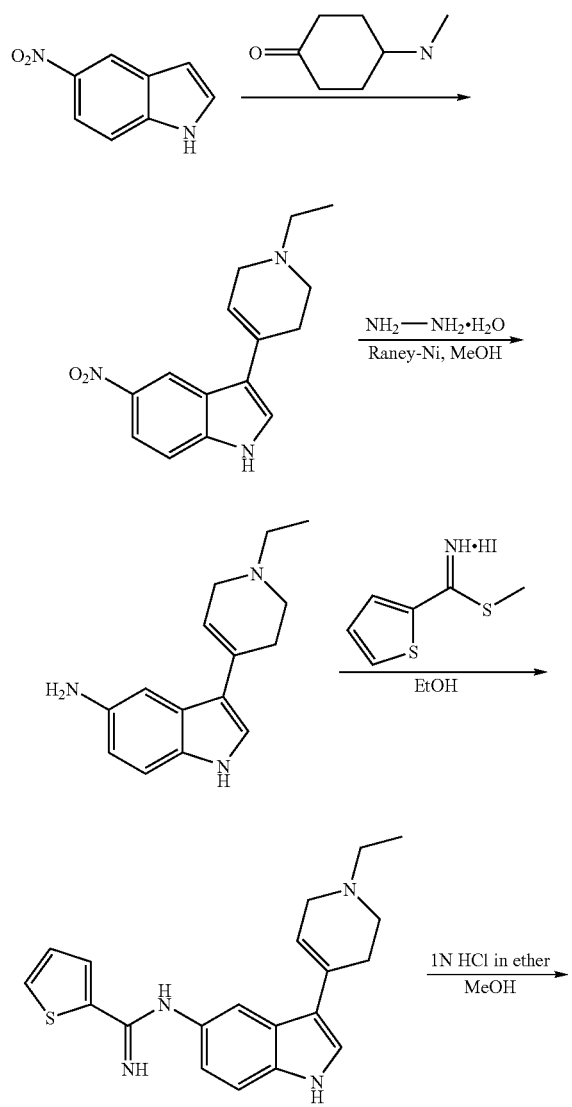

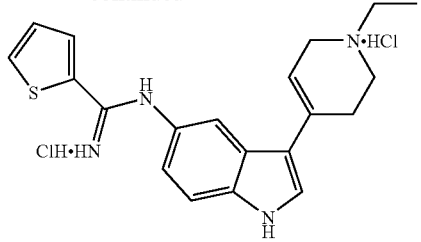

3-(1-Ethyl-1,2,3,6-tetrahydropyridin-4-yl)-5-nitro-1H-indole

A solution of 5-nitro-1H-indole (0.67 g, 4.13 mmol), 1-ethylpiperidin-4-one (1.094 mL, 8.26 mmol) and pyrrolidine (1.025 mL, 12.40 mmol) in dry methanol (10 mL) was refluxed for 48 h. The reaction was brought to room temperature, diluted with water and product was extracted into $CH_2Cl_2$ (2×50 mL). The combined $CH_2Cl_2$ layer was washed with brine (20 mL) and dried ($Na_2SO_4$). Solvent was evaporated, crude was stirred with isopropanol: hexanes, (15 mL, 1:7) and the yellow precipitate was filtered and dried to obtain 3-(1-ethyl-1,2,3,6-tetrahydropyridin-4-yl)-5-nitro-1H-indole (0.87 g, 78%). $^1$H NMR (DMSO-$d_6$) δ 11.87 (s, 1H), 8.69 (d, 1H, J=2.1 Hz), 8.01 (dd, 1H, J=2.4, 9.0 Hz), 7.65 (s, 1H), 7.55 (d, 1H, J=9.0 Hz), 6.18 (s, 1H), 3.16-3.12 (m, 2H), 2.64 (t, 2H, J=5.1 Hz), 2.54-2.42 (m, 4H, merged with DMSO-peak), 1.70 (t, 3H, J=7.2 Hz); ESI-MS (m/z, %): 272 ($MH^+$, 100).

3-(1-Ethyl-1,2,3,6-tetrahydropyridin-4-yl)-1H-indol-5-amine

A suspension of 3-(1-ethyl-1,2,3,6-tetrahydropyridin-4-yl)-5-nitro-1H-indole (0.375 g, 1.382 mmol) in dry methanol (10 mL) was treated with Raney-nickel (0.1 g, 0.351 mmol), followed by hydrazine hydrate (0.672 mL, 13.82 mmol) at room temperature. The resulting mixture was placed in a pre-heated oil bath and refluxed for 5 min. (TLC basis, 2 M $NH_3$ in MeOH:$CH_2Cl_2$, 5:95). The reaction was brought to room temperature, filtered through celite bed and washed with methanol (3×5 mL). The combined methanol layer was evaporated and crude was purified by flash column chromatography (2 M $NH_3$ in MeOH:$CH_2Cl_2$, 5:95) to obtain 3-(1-ethyl-1,2,3,6-tetrahydropyridin-4-yl)-1H-indol-5-amine (0.33 g, 99%) as a foam. $^1$H NMR (DMSO-$d_6$) δ 10.60 (s, 1H), 7.15 (d, 1H, J=2.7 Hz), 7.05 (d, 1H, J=8.4 Hz), 7.00 (d, 1H, J=1.5 Hz), 6.48 (dd, 1H, J=2.1, 8.5 Hz), 5.98 (s, 1H), 4.48 (s, 2H), 3.10-3.04 (m, 2H), 2.59 (t, 2H, J=5.4 Hz), 2.54-2.39 (m, 4H, merged with DMSO peak), 1.06 (t, 3H, J=7.2 Hz); EI-MS (m/z, %): 241 ($M^+$, 100).

N-(3-(1-Ethyl-1,2,3,6-tetrahydropyridin-4-yl)-1H-indol-5-yl)thiophene-2-carboximidamide A solution of 3-(1-ethyl-1,2,3,6-tetrahydropyridin-4-yl)-1H-indol-5-amine (0.32 g, 1.326 mmol) in dry ethanol (10 mL) was treated with methyl thiophene-2-carbimidothioate hydroiodide (0.756 g, 2.65 mmol) at room temperature and stirred overnight (18 h). The reaction was basified with sat. $NaHCO_3$ solution (30 mL) and product was extracted into $CH_2Cl_2$ (2×25 mL). The combined $CH_2Cl_2$ layer was washed with brine (20 mL) and dried ($Na_2SO_4$). Solvent was evaporated and crude was purified by column chromatography (2 M NH₃ in MeOH:CH₂Cl₂, 1:9) to obtain N-(3-(1-ethyl-1,2,3,6-tetrahydropyridin-4-yl)-1H-indol-5-yl)thiophene-2-carboximidamide (0.37 g, 80%) as a solid. ¹H NMR (DMSO-d₆) δ 10.94 (s, 1H), 7.71 (d, 1H, J=3.3 Hz), 7.59 (s, 1H, J=5.1 Hz), 7.31 (dd, 1H, J=2.7, 5.4 Hz), 7.22 (s, 1H), 7.10 (t, 1H, J=4.8 Hz), 6.67 (d, 1H, J=8.4 Hz), 6.26 (brs, 2H), 6.05 (s, 1H), 3.10 (brs, 2H), 2.63 (t, 2H, J=5.1 Hz), 2.54-2.40 (m, 4H, merged with DMSO-peak), 1.06 (t, 3H, J=7.2 Hz); ESI-MS (m/z, %): 351 (MH⁺, 37), 294 (100); ESI-HRMS calculated for C₂₀H₂₃N₄S (MH⁺), calculated: 351.1637; observed: 351.1636.

N-(3-(1-Ethyl-1,2,3,6-tetrahydropyridin-4-yl)-1H-indol-5-yl)thiophene-2-carboximidamide dihydrochloride A solution of N-(3-(1-ethyl-1,2,3N-(3-(1-ethyl-1,2,3,6-tetrahydropyridin-4-yl)-1H-indol-5-yl)thiophene-2-carboximidamide (0.35 g, 0.999 mmol) in dry methanol (5 mL) was treated with 1 N HCl in ether (2.99 mL, 2.99 mmol) at room temperature and stirred for 15 minutes. Solvent was evaporated and crude was dried under vacuum to obtain dihydrochloride salt of N-(3-(1-ethyl-1,2,3,6-tetrahydropyridin-4-yl)-1H-indol-5-yl)thiophene-2-carboximidamide as a solid. ¹H NMR (DMSO-d₆) δ 11.74 (s, 1H), 11.52 (s, 1H), 10.98 (brs, 1H), 9.68 (s, 1H), 8.62 (s, 1H), 8.22-8.16 (m, 2H), 7.93 (s, 1H), 7.68 (d, 1H, J=2.1 Hz), 7.59 (d, 1H, J=8.7 Hz), 7.39 (t, 1H, J=4.2 Hz), 7.18 (d, 1H, J=8.7 Hz), 6.16 (s, 1H), 3.97-3.92 (m, 1H), 3.75-3.59 (m, 2H), 3.27-3.16 (m, 3H), 2.99-2.93 (m, 1H), 2.81-2.75 (m, 1H), 1.32 (t, 3H, J=7.2 Hz).

In experiments carried out as described above, Compound 19 was shown to selectively inhibit nNOS versus eNOS as shown in Table 13.

TABLE 13

| Compound | Structure | Human nNOS (μM) | Human eNOS (μM) | eNOS/nNOS |
|---|---|---|---|---|
| 19 | 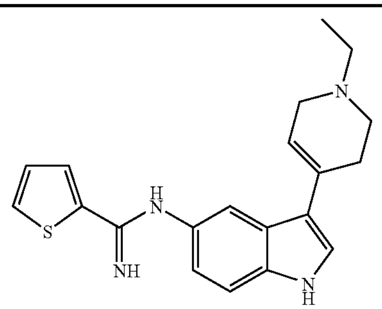 | 0.74 | 68.4 | 92.4 |

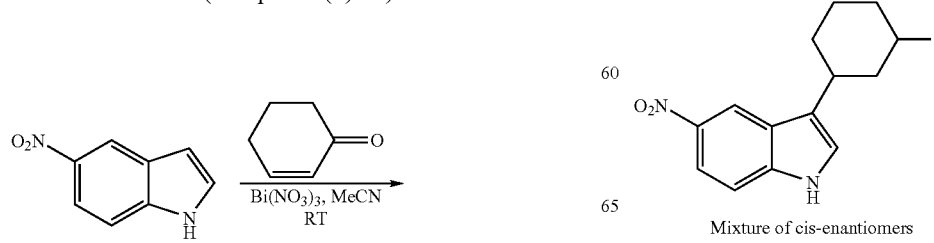

Example 18

Synthesis of N-(3-((1S,3R)-3-(Methylamino)cyclohexyl)-1H-indol-5-yl)thiophene-2-carboximidamide (Compound (±)-20)

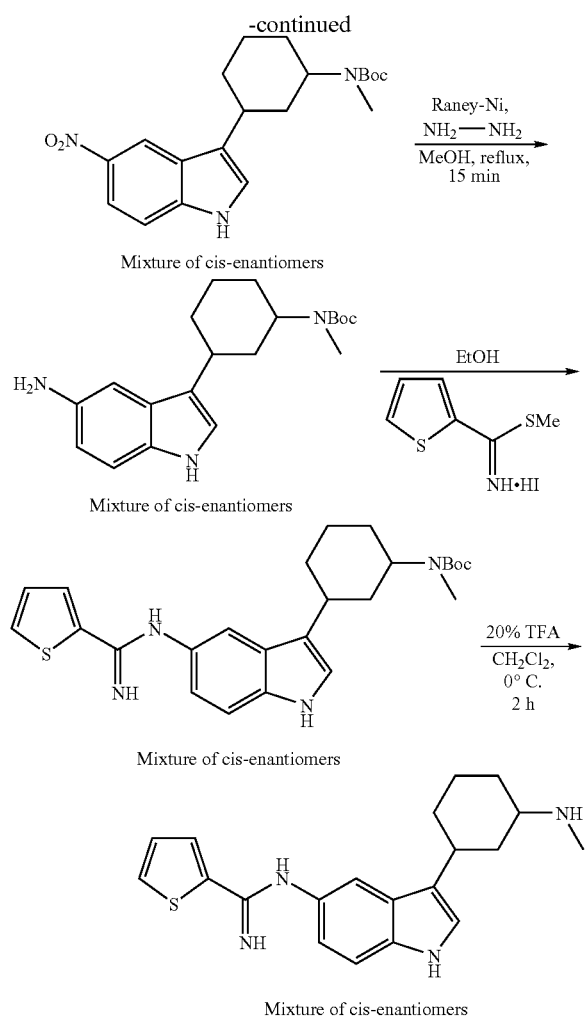

Mixture of cis-enantiomers

3-(5-Nitro-1H-indol-3-yl)cyclohexanone

To a solution of 5-nitroindole (4.00 g, 25.61 mmol) in dry MeCN (5.00 mL) was added cyclohex-2-enone (7.40 mL, 76.83 mmol) and Bi(NO$_3$)$_3$ (0.12 g, 0.26 mmol) and the mixture stirred overnight at room temperature. The solvent then was evaporated and the crude was purified by column chromatography (50% Hexane:50% EtOAc) to obtain the title compound (2.70 g, 41%) as a yellow solid. $^1$H-NMR (CDCl$_3$) δ 1.81-2.09 (m, 3H), 2.26-2.34 (m, 1H), 2.37-2.55 (m, 2H), 2.65 (dd, 1H, J=9.9, 12.9 Hz), 2.77-2.85 (m, 1H), 3.47-3.56 (m, 1H), 7.15 (d, 1H, J=2.1 Hz), 7.41 (d, 1H, J=9.0 Hz), 8.12 (dd, 1H, J=2.1, 9.0 Hz), 8.51 (s, 1H), 8.59 (d, 1H, J=2.1 Hz); EI-MS (m/z, %) 258 (M$^+$, 100).

N-Methyl-3-(5-nitro-1H-indol-3-yl)cyclohexanamine (mixture of trans-enantiomers) and N-Methyl-3-(5-nitro-1H-indol-3-yl)cyclohexanamine (mixture of cis-enantiomers)

To a solution of 3-(5-nitro-1H-indol-3-yl)cyclohexanone (1.20 g, 4.65 mmol) in 1,2-dichloroethane (50 mL) was added AcOH (0.28 mL, 4.65 mmol), MeNH$_2$.HCl (0.38 g, 4.65 mmol) and NaBH(OAc)$_3$ (1.50 g, 7.00 mmol) and the mixture left to stir overnight at room temperature. The reaction mixture was extracted with 2N NaOH (10 mL) and washed with dichloromethane (2×10 mL); the dichloromethane layer was separated and evaporated. The crude was purified by column chromatography (2 M NH$_3$ in MeOH:CH$_2$Cl$_2$, 1:9) to obtain two diastereomers as yellow solids. The stereochemistry of both diastereomers was determined using COSY and NOESY spectroscopic techniques.

First Eluting Compound (Mixture of Trans-Enantiomers)

(0.58 g, 46%); $^1$H-NMR (CDCl$_3$) δ 1.49-1.65 (m, 3H), 1.69-1.88 (m, 3H), 2.04-2.08 (m, 2H), 2.41 (s, 3H), 2.87-2.97 (m, 1H), 3.26-3.37 (m, 1H), 7.12 (s, 1H), 7.36 (d, 1H, J=9.0 Hz), 8.09 (dd, 1H, J=2.1, 9.0 Hz), 8.44 (s, 1H, NH), 8.63 (d, 1H, J=2.1 Hz); EI-MS (m/z, %) 242 (100), 273 (10); 2D NOESY: H$_a$ (δ 3.26-3.37) and H$_c$ (δ 2.87-2.97) do not correlate; there is correlation between H$_c$ and H$_d$; 2D COSY: H$_a$ and H$_c$ do not couple to each other.

Second Eluting Product (Mixture of Cis-Enantiomers)

(0.21 g, 16%); $^1$H-NMR (CDCl$_3$) δ 1.26-1.38 (m, 2H), 1.45-1.57 (m, 2H), 1.89-1.95 (m, 1H), 2.01-2.08 (m, 1H), 2.13-2.17 (m, 1H), 2.33-2.44 (m, 1H), 2.56 (s, 3H), 2.75-2.93 (m, 2H), 7.06 (s, 1H), 7.35 (d, 1H, J=9.0 Hz), 8.06 (dd, 1H, J=2.1, 9.0 Hz), 8.54 (d, 1H, J=2.4 Hz), 8.93 (s, 1H, NH); EI-MS (m/z, %) 230 (100), 273 (30); 2D NOESY: H$_a$ (δ 2.75-2.93) and H$_c$ (δ 2.33-2.44) strongly correlate; there is correlation between H$_c$ and H$_d$; 2D COSY: H$_a$ and H$_c$ do not couple to each other.

tert-Butyl methyl((1R,3S)-3-(5-nitro-1H-indol-3-yl)cyclohexyl)carbamate carbamate (mixture of cis-enantiomers)

To a solution of N-methyl-3-(5-nitro-1H-indol-3-yl)cyclohexanamine (0.40 g, 1.46 mmol) in 1,4-dioxane (10 mL) was added (Boc)$_2$O (0.35 g, 1.61 mmol) and triethyl amine (0.40 mL, 2.92 mmol) and the resulting mixture left to stir overnight at room temperature. The solvent was evaporated and the crude purified on column chromatography (EtOAc:Hexanes, 1:1) to give the title compound as a yellow solid (0.40 g, 73%). $^1$H-NMR (CDCl$_3$) δ 1.34-1.44 (m, 1H), 1.49 (s, 9H), 1.57-1.69 (m, 3H), 1.78-1.86 (m, 1H), 1.92-2.00 (m, 1H), 2.03-2.10 (m, 2H), 2.78 (s, 3H), 2.95-3.06 (m, 1H), 3.96-4.27 (m, 1H), 7.11 (d, 1H, J=1.8 Hz), 7.38 (d, 1H, J=9.0 Hz), 8.10 (dd, 1H, J=2.1, 9.0 Hz), 8.37 (s, 1H, NH), 8.61 (d, 1H, J=2.1 Hz); EI-MS (m/z, %), 242 (100), 373 (20).

tert-Butyl-3-(5-amino-1H-indol-3-yl)cyclohexyl(methyl)carbamate (mixture of cis-enantiomers)

To a solution of tert-butyl methyl-(3-(5-nitro-1H-indol-3-yl)cyclohexyl)carbamate (0.38, g 1.02 mmol) in dry MeOH (10 mL) was added Ra—Ni (0.1 g as a slurry in water) and hydrazine hydrate (0.50 mL, 10.20 mmol). The resulting mixture was immersed in a preheated oil bath and refluxed for 15 min. or until the solution became clear. The reaction was cooled and filtered trough celite, washed with MeOH (20 mL) and the solvent evaporated. The crude was purified on column chromatography (2 M NH$_3$ in MeOH:CH$_2$Cl$_2$, 2:98) to give the title compound as a light brown solid (0.34 g, 97%). $^1$H-NMR (CDCl$_3$) δ 1.31-1.66 (m, 4H), 1.48 (s, 9H), 1.75-1.80 (m, 1H), 1.89-1.96 (m, 1H), 2.03-2.11 (m, 2H), 2.74 (s, 3H), 2.84-2.93 (m, 1H), 3.52 (s, 2H, NH), 4.13-4.26 (m, 1H), 6.65 (dd, 1H, J=2.1, 8.4 Hz), 6.88 (d, 1H, J=2.4 Hz), 6.95 (s, 1H), 7.15 (d, 1H, J=8.4 Hz), 7.72 (s, 1H, NH); EI-MS (m/z, %), 343 (100).

tert-Butyl methyl(3-(5-(thiophene-2-carboximidamido)-1H-indol-3-yl)cyclohexyl)carbamate (mixture of cis-enantiomers)

To a solution of tert-butyl-3-(5-amino-1H-indol-3-yl)cyclohexyl(methyl)carbamate (0.32 g, 0.93 mmol) in dry EtOH (25 mL) was added methyl thiophene-2-carbimidothioate hydroiodide (0.53 g, 1.86 mmol) and the reaction left to stir at room temperature for 48 h. The solvent then was evaporated and the mixture dissolved in dichloromethane (20 mL) and washed with 2N NaOH (10 mL). The organic layer was extracted and evaporated. The crude was purified on column chromatography (2 M $NH_3$ in MeOH:$CH_2Cl_2$, 2:98 to 5:95) to give the title compound as a yellow solid (0.32 g, 75%). $^1$H-NMR (DMSO-$d_6$) δ 1.38 (s, 9H), 1.46-1.68 (m, 5H), 1.84-2.00 (m, 5H), 2.69 (s, 3H), 2.79-2.87 (m, 1H), 3.78-4.09 (m, 1H), 6.20 (s, 2H, NH), 6.62 (dd, 1H, J=1.8, 8.4 Hz), 6.98 (s, 1H) 7.04 (s, 1H), 7.09 (dd, 1H, J=3.6, 3.6 Hz), 7.26 (d, 1H, J=8.4 Hz), 7.58 (d, 1H, J=4.8 Hz), 7.70 (d, 1H, J=3.3 Hz), 10.59 (s, 1H, NH); ESI-MS (m/z, %) 453 (MNa$^+$, 100).

N-(3-(3-(Methylamino)cyclohexyl)-1H-indol-5-yl)thiophene-2-carboximidamide tert-Butyl methyl(3-(5-(thiophene-2-carboximidamido)-1H-indol-3-yl)cyclohexyl)carbamate (0.30 g, 0.66 mmol) was treated with 20% trifluoroacetic acid (TFA) solution (31 mL) in dichloromethane at 0° C. and the mixture left to stir for 2 h at 0° C. The solution then was neutralized with 10% $NH_4OH$, the organic layer separated and evaporated. The crude was purified by column chromatography (2 M $NH_3$ in MeOH:$CH_2Cl_2$, 1:4) to give the title product as a yellow solid (0.22 g, quantitative). $^1$H-NMR (DMSO-$d_6$) δ 1.28-1.61 (m, 4H), 1.84-2.01 (m, 2H), 2.08-2.11 (m, 1H), 2.27-2.35 (m, 1H), 2.58 (s, 3H), 2.86-2.94 (m, 1H), 3.08-3.25 (m, 1H), 7.10 (d, 1H, J=8.4 Hz), 7.28 (d, 1H, J=2.1 Hz), 7.39 (pseudo t, 1H, J=4.5 Hz), 7.52 (d, 1H, J=8.4 Hz), 7.65 (s, 1H), 8.12 (d, 1H, J=3.6 Hz), 8.16 (d, 1H, J=4.5 Hz), 8.58 (s, 2H, NH), 9.61 (s, 1H); ESI-MS (m/z, %) 353 (100), ESI-HRMS calc. for $C_{20}H_{25}N_4S$ 353.1794 found 353.1792.

Example 19

Synthesis of N-(3-(3-(methylamino)cyclohexyl)-1H-indol-5-yl)thiophene-2-carboximidamide dihydrochloride [(+)- and (−)-isomers] (Compounds 20a and 20b)

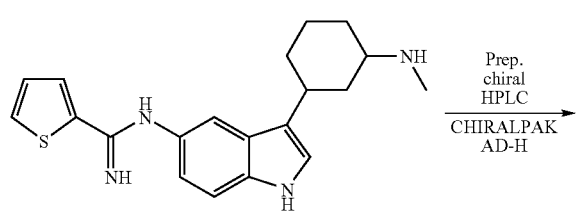

Mixture of cis-enantiomers

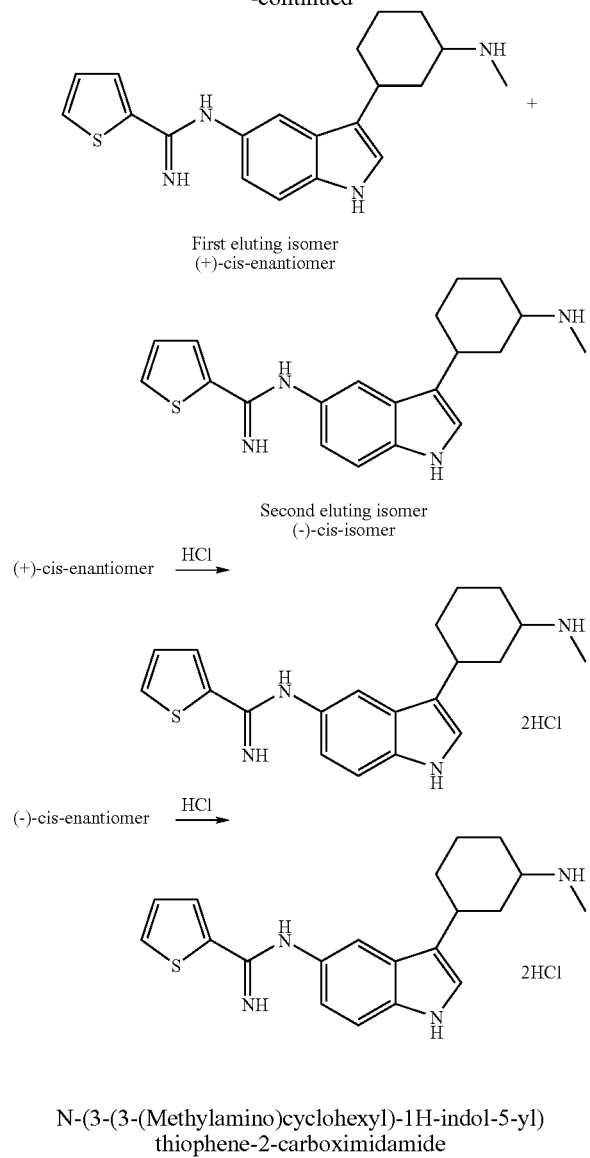

N-(3-(3-(Methylamino)cyclohexyl)-1H-indol-5-yl)thiophene-2-carboximidamide

For complete experimental details and spectral date, see Example 18 (Compound (±)-20).

Chiral Separation

N-(3-(3-(methylamino)cyclohexyl)-1H-indol-5-yl)thiophene-2-carboximidamide (0.95 g, 2.70 mmol) was subjected to a chiral HPLC (CHIRALPAK AD-H) separation. Flow rate 15 mL/min, 15% EtOH: 85% Hexane+0.2% DEA. Maximum loading 270 mg.

First eluting enantiomer started eluting at 15 minutes $[\alpha]_D$=+23.77 (4.50 mg in 2 mL MeOH), 88% ee by HPLC. Second eluting enantiomer started eluting at 28 minutes $[\alpha]_D$=−28.64 (4.80 mg in 2 mL MeOH), 100% ee by HPLC to obtain 160.00 mg of each enantiomer.

N-(3-(3-(Methylamino)cyclohexyl)-1H-indol-5-yl)thiophene-2-carboximidamide dihydrochloride [(+)-cis-enantiomer]

N-(3-(3-(Methylamino)cyclohexyl)-1H-indol-5-yl)thiophene-2-carboximidamide [(+)-cis-enantiomer] (0.16 g, 0.45 mmol) was dissolved in a minimum amount of methanol to which hydrochloric acid (1.00 mL, 1.00 mmol, 1M in diethyl ether) was added. The mixture was left to stir for 1 hour at room temperature. The solvent was evaporated and the resulting solid dried under vacuum to give the product (0.16 g, 97%) as a light yellow solid. $^1$H-NMR (MeOH-d$_4$) δ 1.30-1.67 (m, 4H), 1.93-2.24 (m, 3H), 2.47-2.51 (m, 1H), 2.73 (s, 3H), 2.96-309 (m, 1H), 7.16 (d, 1H, J=8.7 Hz), 7.25 (s, 1H), 7.38 (dd, 1H, J=4.5, 8.4 Hz), 7.56 (d, 1H, J=8.4 Hz), 7.73 (s, 1H), 8.05-8.07 (m, 2H); ESI-MS (m/z, %) 322 (100), 353 (MH$^+$, free base, 50), ESI-HRMS calc. for C$_{16}$H$_{25}$N$_4$O$_5$ (MH$^+$, free base), calculated: 353.1819. found: 353.1807.

N-(3-(3-(Methylamino)cyclohexyl)-1H-indol-5-yl)thiophene-2-carboximidamide dihydrochloride [(−)-cis-enantiomer]

N-(3-(3-(Methylamino)cyclohexyl)-1H-indol-5-yl)thiophene-2-carboximidamide [(−)-cis-enantiomer] (0.16 g, 0.45 mmol) was dissolved in minimum amount of methanol to which hydrochloric acid (1.00 mL, 1.00 mmol, 1M in diethyl ether) was added. The mixture was left to stir for 1 hour at room temperature and then the solvent evaporated and the solid dried under vacuum to give the product (0.16 g, 97%) as a light yellow solid. $^1$H-NMR (MeOH-d$_4$) δ 1.27-1.71 (m, 5H), 1.99-2.33 (m, 3H), 2.47-2.52 (m, 1H), 2.72 (s, 3H), 2.96-3.09 (m, 1H), 7.16 (dd, 1H, J=2.1, 8.7 Hz), 7.25 (s, 1H), 7.38 (dd, 1H, J=4.2, 4.8 Hz), 7.56 (d, 1H, J=8.7 Hz), 7.73 (d, 1H, J=1.8 Hz), 8.05-8.07 (m, 2H); ESI-MS (m/z, %) 322 (100), 353 (MH$^+$, free base, 50), ESI-HRMS calc. for C$_{16}$H$_{25}$N$_4$O$_5$ (MH$^+$, free base), calculated: 353.1819. found: 353.1809.

In experiments carried out as described above, Compounds (±)-20, 20a, and 20b were shown to selectively inhibit nNOS versus eNOS and further to exhibit 5HT 1B and 1D activities, as shown below in Table 14.

TABLE 14

| Compound number | Structure | Human nNOS (μM) | Human eNOS (μM) | eNOS/nNOS | 5HT 1B (μM) | 5HT 1D (μM) |
|---|---|---|---|---|---|---|
| (±)-20 | Mixture of cis-enantiomers | 0.49 | 77.6 | 158.3 | 20 | 2.8 |
| 20a (isomer-1) | (+)-cis-enantiomer | 0.57 | 49.3 | 86.4 | 1.3 | 3.2 |
| 20b (isomer-2) | (−)-cis-enantiomer | 1.37 | 75 | 54.7 | 12 | 1.4 |

Example 20

Synthesis of N-(3-(3-(methylamino)cyclohexyl)-1H-indol-5-yl)thiophene-2-carboximidamide (mixture of trans-enantiomers) (Compound 21)

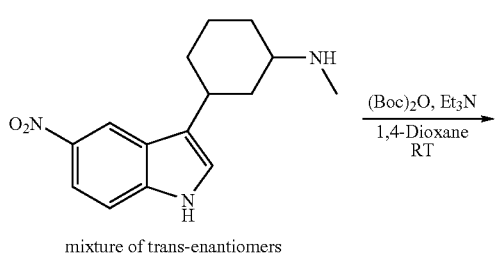

mixture of trans-enantiomers (Boc)$_2$O, Et$_3$N
1,4-Dioxane
RT

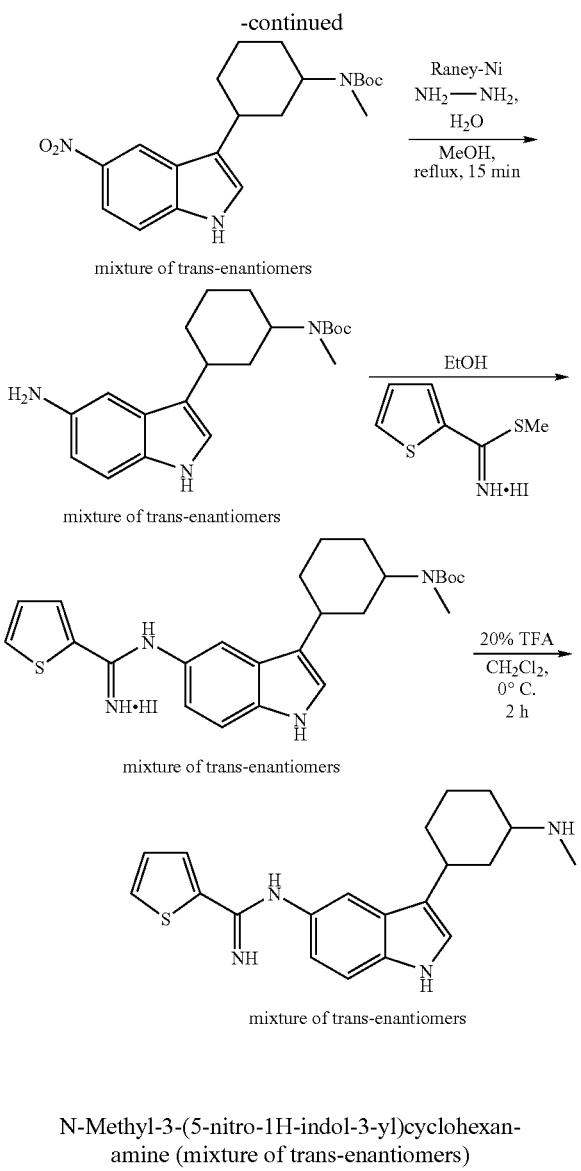

N-Methyl-3-(5-nitro-1H-indol-3-yl)cyclohexanamine (mixture of trans-enantiomers)

For complete experimental details and spectral data, see example 19.

tert-Butyl methyl(3-(5-nitro-1H-indol-3-yl)cyclohexyl)carbamate (mixture of trans-enantiomers)

To a solution of N-methyl-3-(5-nitro-1H-indol-3-yl)cyclohexanamine (0.55 g, 2.0 mmol) in 1,4-dioxane (10 mL) was added (Boc)$_2$O (0.48 g, 2.21 mmol) and triethylamine (0.56 mL, 4.10 mmol) and the resulting mixture left to stir overnight at room temperature. The solvent was evaporated and the crude purified on column chromatography (EtOAc:Hexanes, 1:1) to give the compound as a yellow solid (0.73 g, quantitative). $^1$H-NMR (CDCl$_3$) δ 1.43 (s, 9H), 1.64-1.81 (m, 3H), 1.86-1.98 (m, 1H), 1.49-1.57 (m, 2H), 2.09-2.18 (m, 2H), 2.78 (s, 3H), 3.57-3.63 (m, 1H), 4.35-4.52 (m, 1H), 7.26 (s, 1H), 7.35 (d, 1H, J=9.0 Hz), 8.08 (dd, 1H, J=2.1, 9.0 Hz), 8.50 (s, 1H, NH), 8.57 (d, 1H, J=2.1 Hz); EI-MS (m/z, %) 299 (M$^+$, 100).

tert-Butyl 3-(5-amino-1H-indol-3-yl)cyclohexyl(methyl)carbamate (mixture of trans-enantiomers)

To a solution of tert-butyl methyl(3-(5-nitro-1H-indol-3-yl)cyclohexyl)carbamate (0.70 g 1.87 mmol) in dry MeOH (15 mL) was added Raney-Ni (0.1 g as a slurry in water) and hydrazine hydrate (1.00 mL, 18.70 mmol). The resulting mixture was immersed in a preheated oil bath and refluxed for 15 min. or until the solution became clear. The reaction was cooled and filtered trough Celite, washed with MeOH (20 mL) and the solvent evaporated. The crude was purified on column chromatography (2 M NH$_3$ in MeOH:CH$_2$Cl$_2$, 2:98) to give the title compound as a light brown solid (0.60 g, 92%). $^1$H-NMR (CDCl$_3$) δ 1.42 (s, 9H), 1.46-1.72 (m, 6H), 1.88 (ddd, 1H, J=5.4, 12.3, 24.9 Hz), 2.05-2.16 (m, 2H), 2.76 (s, 3H), 3.50 (s, 2H, NH), 4.36-4.51 (m, 1H), 6.64 (dd, 1H, J=2.1, 8.4 Hz), 6.89 (d, 1H, J=2.1 Hz), 7.16 (d, 1H, J=8.4 Hz), 7.28 (s, 1H), 7.76 (s, 1H, NH); EI-MS (m/z, %) 343 (M$^+$, 70), 212 (100).

tert-Butyl methyl(3-(5-(thiophene-2-carboximidamido)-1H-indol-3-yl)cyclohexyl)carbamate (mixture of trans-enantiomers)

To a solution of tert-butyl 3-(5-amino-1H-indol-3-yl)cyclohexyl(methyl)carbamate (0.57 g, 1.66 mmol) in dry EtOH (25 mL) was added methyl thiophene-2-carbimidothioate hydroiodide (0.75 g, 3.32 mmol) and the reaction left to stir at room temperature for 48 h. The solvent then was evaporated and the mixture dissolved in dichloromethane (20 mL) and washed with 2N NaOH (10 mL). The organic layer was extracted and evaporated. The crude was purified on column chromatography (2 M NH$_3$ in MeOH:CH$_2$Cl$_2$, 2:98 to 5:95) to give the title compound as a yellow solid (0.62 g, 81%). $^1$H-NMR (DMSO-d$_6$) δ 1.35 (s, 9H), 1.42-1.71 (m, 5H), 1.88-1.93 (m, 2H), 1.98-2.04 (m, 1H), 2.69 (s, 3H), 3.40-3.53 (m, 1H), 4.24-4.27 (m, 1H), 6.22 (s, 2H, NH), 6.64 (dd, 1H, J=1.8, 8.4 Hz), 6.93 (s, 1H), 7.09 (dd, 1H, J=3.6, 5.1 Hz), 7.28 (d, 2H, J=8.4 Hz), 7.58 (d, 1H, J=4.5 Hz), 7.70 (d, 1H, J=3.6 Hz), 10.68 (s, 1H, NH); ESI-MS (m/z, %) 453 (MNa$^+$, 100).

N-(3-(3-(Methylamino)cyclohexyl)-1H-indol-5-yl)thiophene-2-carboximidamide (mixture of trans-enantiomers)

tert-Butyl methyl(3-(5-(thiophene-2-carboximidamido)-1H-indol-3-yl)cyclohexyl)carbamate (0.60 g, 0.13 mmol) was treated with 20% TFA solution (31 mL) in dichloromethane at 0° C. and the mixture left to stir for 2 hours at 0° C. The solution then was neutralized with 10% NH$_4$OH, the organic layer separated and evaporated. The crude product was purified by column chromatography (2 M NH$_3$ in MeOH: CH$_2$Cl$_2$, 1:4) to give the final product as a yellow solid (0.45 g, quantitative). $^1$H-NMR (DMSO-d$_6$) δ 1.51-1.60 (m, 3H), 1.69-1.77 (m, 3H), 1.83-1.91 (m, 1H), 1.96-2.07 (m, 1H), 2.40 (s, 3H), 3.24-3.51 (m, 3H), 6.20 (brs, 2H, NH), 6.63 (d, 1H, J=10.2 Hz), 7.02 (d, 2H, J=10.4 Hz), 7.09 (dd, 1H, J=3.6, 4.8 Hz), 7.58 (d, 1H, J=5.1 Hz), 7.71 (d, 1H, J=3.3 Hz), 10.59 (s, 1H, NH); ESI-MS (m/z, %) 353 (MH$^+$, 80), 322 (100), ESI-HRMS (MH$^+$) calc. for C$_{20}$H$_{25}$N$_4$S (MH$^+$), calculated: 353.1794. found: 353.1812.

Example 21

Synthesis of N-(3-(3-(ethylamino)cyclohexyl)-1H-indol-5-yl)thiophene-2-carboximidamide (mixture of trans-enantiomers), (Compound 22)

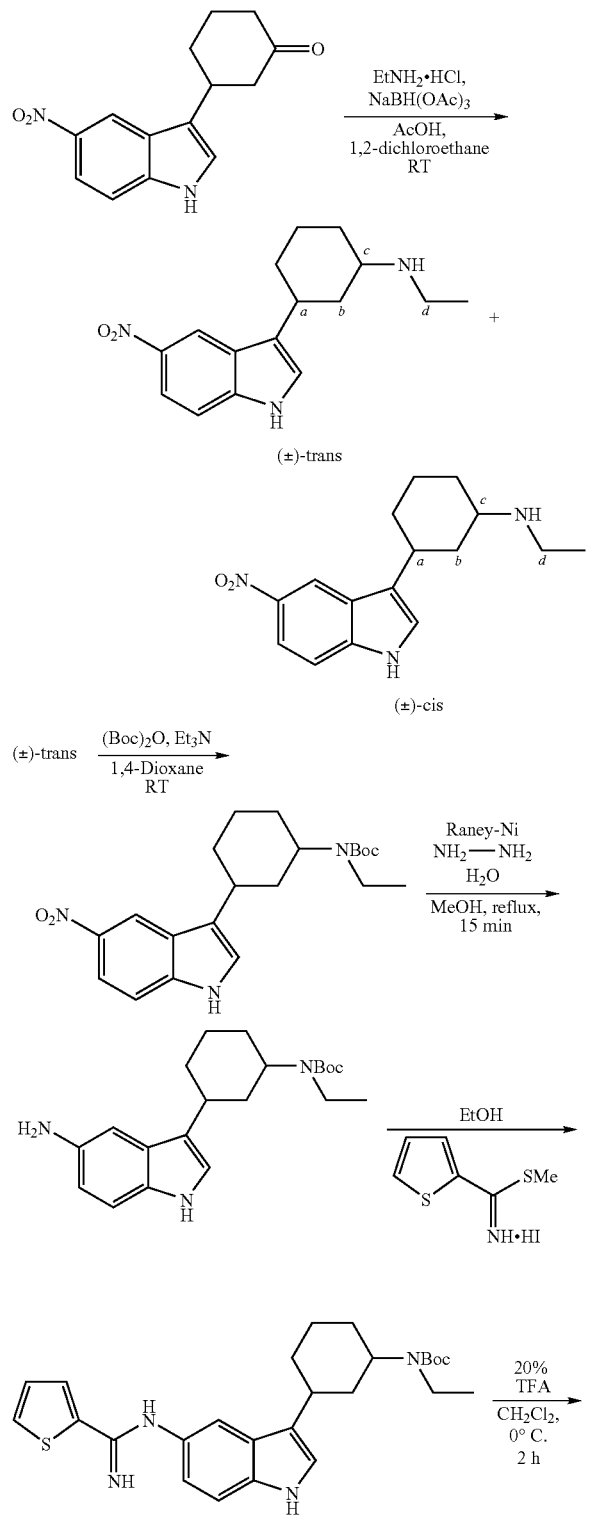

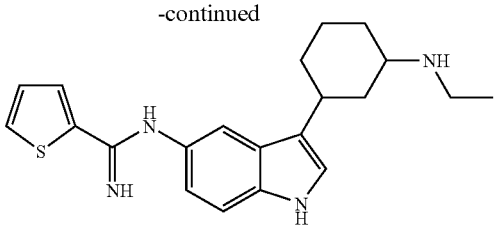

3-(5-Nitro-1H-indol-3-yl)cyclohexanone

For complete experimental details, see example 19.

N-Ethyl-3-(5-nitro-1H-indol-3-yl)cyclohexanamine ((±)-trans) and N-ethyl-3-(5-nitro-1H-indol-3-yl)cyclohexanamine ((±)-cis)

To a solution of 3-(5-nitro-1H-indol-3-yl)cyclohexanone (1.20 g, 4.65 mmol) in 1,2-dichloroethane (50 mL) was added AcOH (0.28 mL, 4.65 mmol), EtNH$_2$.HCl (0.38 g, 4.65 mmol) and NaBH(OAc)$_3$ (1.50 g, 7.00 mmol) and the mixture left to stir overnight at room temperature. The reaction mixture was extracted with 2N NaOH (10 mL) and washed with dichloromethane (2×10 mL), the dichloromethane layer was separated and evaporated. The crude was purified by column chromatography (2M NH$_3$ in MeOH:CH$_2$Cl$_2$, 1:9) to obtain two diastereomers as yellow solids.

First Eluting Isomer (Mixture of Trans-Enantiomer)

(0.70 g, 52%): $^1$H-NMR (CDCl$_3$) δ 1.17 (t, 3H, J=8.4 Hz), 1.55-1.70 (m, 4H), 1.74-1.82 (m, 2H), 2.01-2.07 (m, 2H), 2.70 (q, 2H, J=7.2, 7.2 Hz), 3.01-3.06 (m, 1H), 3.24-3.42 (m, 1H), 7.12 (d, 1H, J=2.1 Hz), 7.37 (d, 1H, J=9.0 Hz), 8.09 (dd, 1H, J=2.1, 9.0 Hz), 8.34 (s, 1H, NH), 8.64 (d, 1H, J=2.1 Hz); EI-MS (m/z, %) 287 (M$^+$, 10), 242 (100); 2D NOESY: H$_a$ (δ 3.24-3.42) and H$_c$ (δ3.01-3.06) weakly correlate; there is correlation between H$_c$ and H$_d$; 2D COSY: H$_a$ and H$_c$ do not couple to each other.

Second Eluting Isomer (Mixture of Cis-Enantiomers)

(0.21 g, 16%): $^1$H-NMR (CDCl$_3$) δ 1.14 (t, 3H), 1.29-1.44 (m, 3H), 1.47-1.63 (m, 2H), 1.84-1.97 (m, 1H), 2.04-2.11 (m, 2H), 2.28-2.32 (m, 1H), 2.75 (q, 2H, J=7.2, 7.2 Hz), 2.89-3.00 (m, 1H), 7.10 (d, 1H, J=1.8 Hz), 7.37 (d, 1H, J=9.0 Hz), 8.10 (dd, 1H, J=2.1, 9.0 Hz), 8.37 (s, 1H, NH), 8.61 (d, 1H, J=2.1 Hz); EI-MS (m/z, %) 287 (M$^+$, 15), 244 (100); 2D NOESY: H$_a$ (δ2.89-3.00) and H$_c$ (δ2.28-2.32) strongly correlate; there is correlation between H$_c$ and H$_d$; 2D COSY: H$_a$ and H$_c$ do not couple to each other.

tert-Butyl ethyl(3-(5-nitro-1H-indol-3-yl)cyclohexyl) carbamate (mixture of trans-enantiomers)

To a solution of N-ethyl-3-(5-nitro-1H-indol-3-yl)cyclohexanamine (0.67 g, 2.36 mmol) in 1,4-dioxane (10 mL) was added (Boc)$_2$O (0.57 g, 2.60 mmol) and triethylamine (0.66 mL, 4.74 mmol) and the resulting mixture left to stir overnight at room temperature. The solvent was evaporated and the crude purified on column chromatography (50% Hexane: 50% EtOAc) to give the compound as a yellow solid (0.72 g, 78%). $^1$H-NMR (CDCl$_3$) δ 1.14 (t, 3H, J=6.9 Hz), 1.45-1.49 (m, 9H, 3H), 1.62-1.79 (m, 3H), 1.86-1.96 (m, 1H), 2.07-2.17

(m, 2H), 3.07-3.28 (m, 2H), 3.57-3.61 (m, 1H), 7.26 (s, 1H), 7.35 (d, 1H, J=9.0 Hz), 7.63 (s, 1H), 8.08 (dd, 1H, J=9.0, 2.1 Hz), 8.57 (d, 1H, J=2.1 Hz); ESI-MS (m/z, %) 410 (MNa+, 50), 288 (100).

tert-Butyl 3-(5-amino-1H-indol-3-yl)cyclohexyl (ethyl)carbamate (mixture of trans-enantiomers)

To a solution of tert-butyl ethyl(3-(5-nitro-1H-indol-3-yl)cyclohexyl)carbamate (0.70, g 1.81 mmol) in dry MeOH (15 mL) was added Raney-Ni (0.1 g as a slurry in water) and hydrazine hydrate (0.90 mL, 18.10 mmol). The resulting mixture was immersed in a preheated oil bath and refluxed for 15 minutes or until the solution became clear. The reaction was cooled and filtered trough Celite, washed with MeOH (20 mL), and the solvent evaporated. The crude was purified on column chromatography (2 M $NH_3$ in MeOH:$CH_2Cl_2$, 2:98) to give the title compound as a brownish solid (0.64 g, quantitative). $^1$H-NMR ($CDCl_3$) δ 1.12 (t, 3H, J=6.8 Hz), 1.45 (s, 9H), 1.53-1.69 (m, 3H), 1.71-1.79 (m 1H), 1.82-1.92 (m, 1H), 2.07-2.17 (m, 2H), 3.06-3.24 (m, 2H), 3.43-3.56 (m, 1H), 4.43 (s, 1H), 6.64 (dd, 1H, J=2.1, 8.4 Hz), 6.89 (d, 1H, J=2.1 Hz), 7.15 (d, 1H, J=8.4 Hz), 7.26 (s, 1H), 7.33 (s, 1H), 7.82 (s, 1H); EI-MS (m/z, %) 357 (M+, 70), 212 (100).

tert-Butyl ethyl(3-(5-(thiophene-2-carboximidamido)-1H-indol-3-yl)cyclohexyl)carbamate (mixture of trans-enantiomers)

To a solution of tert-butyl 3-(5-amino-1H-indol-3-yl)cyclohexyl(ethyl)carbamate (0.62 g, 1.73 mmol) in dry EtOH (25 mL) was added methyl thiophene-2-carbimidothioate hydroiodide (1.00 g, 3.47 mmol) and the reaction left to stir at room temperature for 48 hours. The solvent then was evaporated and the mixture dissolved in dichloromethane (20 mL) and washed with 2N NaOH (10 mL). The organic layer was extracted and evaporated. The crude was purified on column chromatography (2 M $NH_3$ in MeOH:$CH_2Cl_2$, 2:98 to 5:95) to give the title compound as a yellow solid (0.80 g, quantitative). $^1$H-NMR (DMSO-$d_6$) δ 1.04 (t, 3H, J=6.9 Hz), 1.36 (s, 9H), 1.44-1.68 (m, 5H), 1.84-2.04 (m, 3H), 3.05-3.20 (m, 2H), 3.42-3.53 (m, 1H), 4.19-4.26 (m, 1H), 6.21 (s, 2H), 6.64 (dd, 1H, J=1.8, 8.4 Hz), 6.92 (s, 1H), 7.09 (dd, 1H, J=3.6, 5.1 Hz), 7.26 (s, 1H), 7.29 (s, 1H), 7.58 (d, 1H, J=5.1 Hz), 7.70 (d, 1H, J=3.9 Hz), 10.67 (s, 1H). ESI-MS (m/z, %) 467 (MH+, 100)

N-(3-(3-(Ethylamino)cyclohexyl)-1H-indol-5-yl)thiophene-2-carboxamide (mixture of trans-enantiomers)

tert-Butyl ethyl(3-(5-(thiophene-2-carboximidamido)-1H-indol-3-yl)cyclohexyl)carbamate (0.75 g, 1.61 mmol) was treated with 20% TFA solution (31 mL) in dichloromethane at 0° C. and the mixture left to stir for 2 h at 0° C. The solution then was neutralized with 10% $NH_4OH$ solution, the organic layer separated and evaporated. The crude product was purified by column chromatography (2 M $NH_3$ in MeOH:$CH_2Cl_2$, 1:4) to give the final product as a yellow solid (0.50 g, 85%). $^1$H-NMR (DMSO-$d_6$) δ 1.05 (t, 3H, J=6.9 Hz), 1.44-1.51 (m, 3H), 1.58-1.82 (m, 3H), 1.89-1.97 (m, 2H), 2.58 (q, 2H, J=7.2 Hz), 2.85-2.99 (m, 1H), 3.08-3.23 (m, 1H), 6.19 (s, 2H), 6.62 (d, 1H, J=8.4 Hz), 6.98-7.00 (m, 2H), 7.09 (dd, 1H, J=3.9, 5.1 Hz), 7.26 (d, 1H, J=8.4 Hz), 7.58 (d, 1H, J=5.1 Hz), 7.70 (d, 1H, J=3.0 Hz), 10.54 (s, 1H); ESI-MS (m/z, %) 367 (MH+, 50%), 322 (100), ESI-HRMS (MH+) calc. for $C_{21}H_{27}N_4S$, calculated: 367.1950. found: 367.1956.

Example 22

Synthesis of N-(3-(3-(ethylamino)cyclohexyl)-1H-indol-5-yl)thiophene-2-carboximidamide (mixture of cis-enantiomers) (Compound 23)

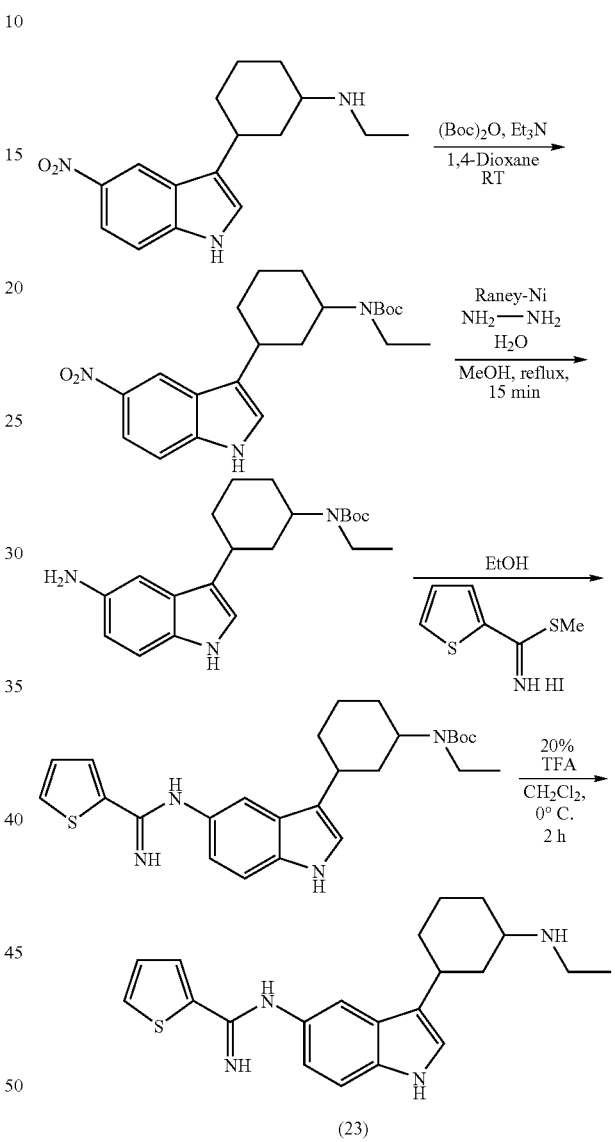

N-Ethyl-3-(5-nitro-1H-indol-3-yl)cyclohexanamine

For complete experimental details and spectral data, see example 21.

tert-Butyl ethyl(3-(5-nitro-1H-indol-3-yl)cyclohexyl)carbamate (mixture of cis-enantiomers)

To a solution of N-ethyl-3-(5-nitro-1H-indol-3-yl)cyclohexanamine (0.20 g, 0.69 mmol) in 1,4-dioxane (5 mL) was added $(Boc)_2O$ (0.17 g, 0.76 mmol) and triethylamine (0.20 mL, 1.40 mmol) and the resulting mixture left to stir overnight at room temperature. The solvent was evaporated and the crude purified on column chromatography (EtOAc:Hexanes, 1:1) to give the compound as a yellow solid (0.26 g, 97%). $^1$H-NMR (DMSO-$d_6$) δ 1.04 (t, 3H, J=6.9 Hz), 1.49-1.23 (m, 2H), 1.42 (s, 9H), 1.51-1.57 (m, 2H), 1.64-1.75 (m, 2H), 1.86-1.95 (m, 2H), 2.96-3.04 (m, 1H), 3.14 (q, 2H, J=6.9 Hz), 7.39 (s, 1H), 7.50 (d, 1H, J=9.0 Hz), 7.97 (dd, 1H, J=2.1, 9.0 Hz), 8.55 (d, 1H, J=2.1 Hz); EI-MS (m/z, %) 387 (M$^+$, 20), 270 (100).

tert-Butyl 3-(5-amino-1H-indol-3-yl)cyclohexyl (ethyl)carbamate (mixture of cis-enantiomers)

To a solution of tert-butyl ethyl(3-(5-nitro-1H-indol-3-yl)cyclohexyl)carbamate (0.24 g, 0.62 mmol) in dry MeOH (10 mL) was added Raney-Ni (0.1 g as a slurry in water) and hydrazine hydrate (0.30 mL, 6.20 mmol). The resulting mixture was immersed in a preheated oil bath and refluxed for 15 min. or until the solution became clear. The reaction was cooled and filtered trough celite, washed with MeOH (20 mL) and the solvent evaporated. The crude material was purified on column chromatography (2 M NH$_3$ in MeOH:CH$_2$Cl$_2$, 2:98) to give the title compound as a brownish solid (0.21 g, 96%). $^1$H-NMR (CDCl$_3$) δ1.09 (t, 3H, J=6.9 Hz), 1.30-1.66 (m, 3H), 1.48 (s, 9H), 1.80-1.83 (m, 1H), 1.90-1.94 (m, 1H), 1.98-2.04 (m, 1H), 2.11-2.15 (m, 1H), 2.80-2.90 (m, 1H), 3.05-3.22 (m, 2H), 4.12-4.19 (m, 1H), 6.65 (dd, 1H, J=2.1, 8.7 Hz), 6.87 (d, 1H, J=2.1 Hz), 6.96 (s, 1H), 7.15 (d, 1H, J=8.7 Hz), 7.725 (s, 1H); EI-MS (m/z, %) 357 (M$^+$, 100).

tert-Butyl ethyl(3-(5-(thiophene-2-carboximidamido)-1H-indol-3-yl)cyclohexyl)carbamate (mixture of cis-enantiomers)

To a solution of tert-butyl 3-(5-amino-1H-indol-3-yl)cyclohexyl(ethyl)carbamate (0.19 g, 0.53 mmol) in dry EtOH (20 mL) was added methyl thiophene-2-carbimidothioate hydroiodide (0.30 g, 1.06 mmol) and the reaction left to stir at room temperature for 48 hours. The solvent then was evaporated and the mixture dissolved in dichloromethane (20 mL) and washed with 2N NaOH (10 mL). The organic layer was extracted and evaporated. The crude was purified on column chromatography (2 M NH$_3$ in MeOH:CH$_2$Cl$_2$, 2:98 to 5:95) to give the title compound as a yellow solid (0.19 g, 78%). 1H-NMR (DMSO-$d_6$) δ 1.04 (t, 3H, J=6.9 Hz), 1.39 (s, 9H), 1.46-1.57 (m, 3H), 1.57-1.74 (m, 2H), 1.80-1.94 (m, 3H), 2.77-2.89 (m, 1H), 3.13 (q, 2H, J=6.0 Hz), 3.89-4.03 (m, 1H), 6.83 (d, 1H, J=8.4 Hz), 7.13 (s, 1H), 7.22 (dd, 1H, J=4.5, 8.7 Hz), 7.29 (s, 1H), 7.37 (d, 1H, J=8.7 Hz), 7.84 (d, 1H, J=3.3 Hz), 7.88 (d, 1H, J=2.1 Hz), 10.83 (s, 1H, NH); ESI-MS (m/z, %) 467 (MH$^+$, 100).

N-(3-(3-(Ethylamino)cyclohexyl)-1H-indol-5-yl)thiophene-2-carboximidamide (mixture of cis-enantiomers)

tert-Butyl ethyl(3-(5-(thiophene-2-carboximidamido)-1H-indol-3-yl)cyclohexyl)carbamate (0.17 g, 0.36 mmol) was treated with 20% TFA solution (20 mL) in dichloromethane at 0° C. and the mixture left to stir for 2 hours at 0° C. The solution then was neutralized with 10% NH$_4$OH solution, the organic layer separated and evaporated. The crude was purified by column chromatography (20% 2N NH$_3$ in MeOH: 80% CH$_2$Cl$_2$) to give the final product as a yellow solid (0.50 g, 85%). $^1$H-NMR (DMSO-$d_6$) δ 1.11 (t, 3H, J=6.9 Hz), 1.21-1.53 (m, 4H), 1.81-2.11 (m, 3H), 2.27-2.37 (m, 1H), 2.82-2.88 (m, 3H), 2.99-3.07 (m, 1H), 6.22 (s, 2H, NH), 6.64 (d, 1H, J=8.4 Hz), 7.01-7.03 (m, 2H), 7.10 (dd, 1H, J=3.6, 5.1 Hz), 7.28 (d, 1H, J=8.7 Hz), 7.59 (d, 1H, J=5.1 Hz), 7.71 (d, 1H, J=3.0 Hz), 10.62 (s, 1H, NH); ESI-MS (m/z, %) 367 (MH$^+$, 50), 322 (100), ESI-HRMS calc. for $C_{21}H_{27}N_4S$ (MH$^+$) 367.1950 found 367.1968.

Example 23

Synthesis of N-(3-(1-(2-hydroxyethyl)-1,2,3,6-tetrahydropyridin-4-yl)-1H-indol-5-yl)thiophene-2-carboximidamide (Compound 24)

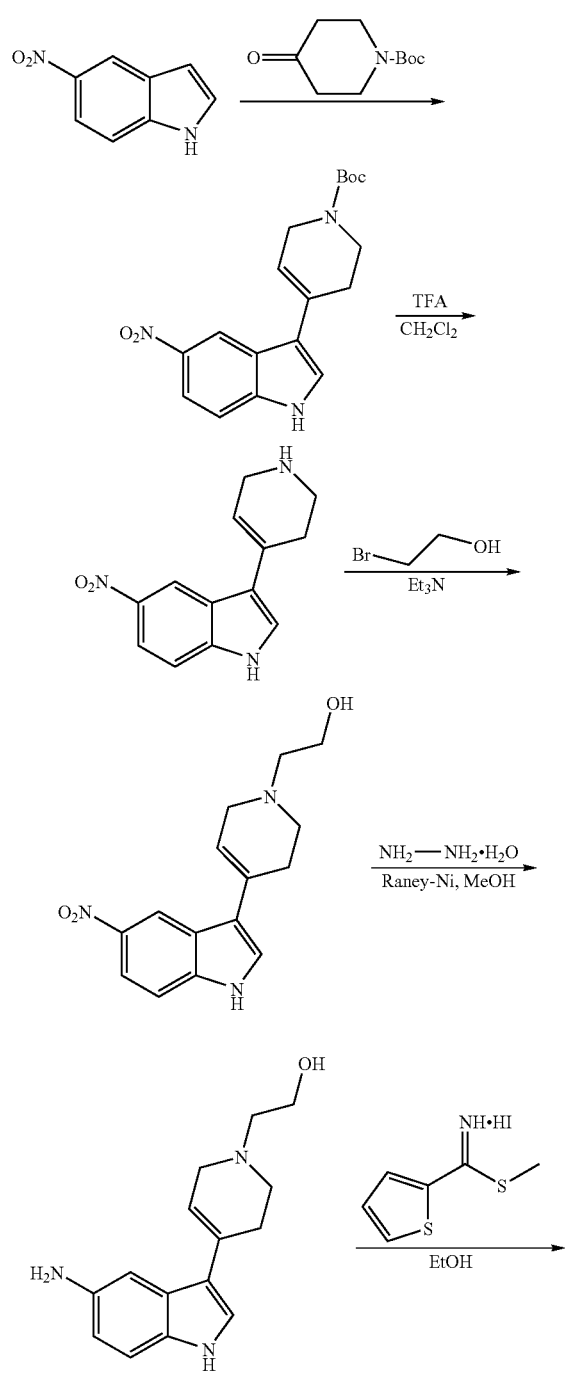

-continued

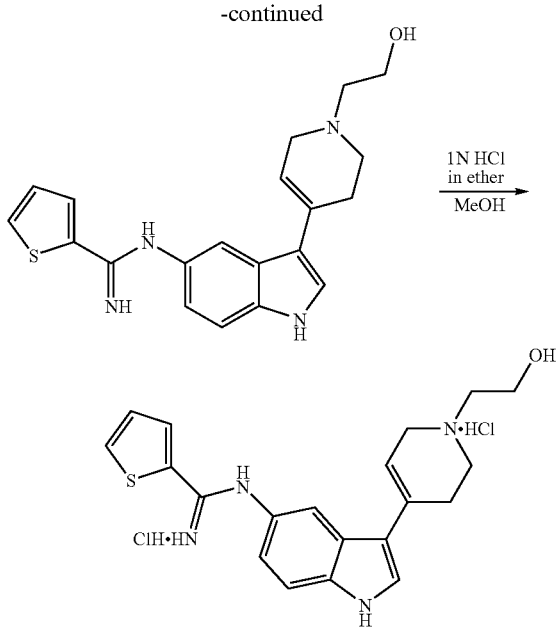

Tert-butyl 4-(5-nitro-1H-indol-3-yl)-5,6-dihydropyridine-1(2H)-carboxylate

A solution of 5-nitro-1H-indole (1 g, 6.17 mmol), tert-butyl 4-oxopiperidine-1-carboxylate (2.458 g, 12.33 mmol) and pyrrolidine (1.530 mL, 18.50 mmol) were refluxed for 48 hours. The reaction was brought to room temperature, diluted with water (50 mL) and product was extracted into ethyl acetate (2×50 mL). The combined ethyl acetate layer was washed with brine (15 mL) and dried ($Na_2SO_4$). Solvent was evaporated and crude was diluted with isopropanol: hexanes, 1:6 (20 mL). After stirring for 15 minutes, the solid was filtered off, washed with hexanes (2×10 mL), and dried to obtain tert-butyl 4-(5-nitro-1H-indol-3-yl)-5,6-dihydropyridine-1(2H)-carboxylate (1.515 g, 71.5%). $^1$H NMR ($CDCl_3$) δ 8.83 (d, 1H, J=1.5 Hz), 8.60 (brs, 1H), 8.14 (dd, 1H, J=2.1, 9.0 Hz), 7.42 (d, 1H, J=9.0 Hz), 7.31 (d, 1H, J=2.1 Hz), 6.21 (s, 1H), 4.20-4.16 (m, 2H), 3.70 (t, 2H, J=5.7 Hz), 2.60-2.50 (m, 2H), 1.51 (s, 9H).

5-Nitro-3-(1,2,3,6-tetrahydropyridin-4-yl)-1H-indole

A solution of tert-butyl 4-(5-nitro-1H-indol-3-yl)-5,6-dihydropyridine-1(2H)-carboxylate (0.8 g, 2.330 mmol) in $CH_2Cl_2$ (16 mL) was treated with TFA (4 mL) at 0° C. and the resulting mixture was stirred at same temperature for 3 h. The reaction was evaporated and crude was basified with 1 N NaOH solution (pH ~14). The solid was filtered off, washed with water (2×10 mL). The crude was dried under vacuum and treated with 10% ethyl acetate in hexanes (20 mL). The solid was filtered and washed with hexanes (2×5 mL). The yellow solid was dried under vacuum to obtain 5-nitro-3-(1,2,3,6-tetrahydropyridin-4-yl)-1H-indole (0.56 g, 99%). $^1$H NMR (DMSO-$d_6$) δ 8.69 (d, 1H, J=2.1 Hz), 8.00 (dd, 1H, J=2.1, 9.0 Hz), 7.63 (s, 1H), 7.55 (d, 1H, J=9.0 Hz), 6.21 (s, 1H), 3.42-3.30 (m, 2H, merged with DMSO-peak), 2.93 (t, 2H, J=5.4 Hz), 2.40-2.30 (m, 2H); ESI-MS (m/z, %): 244 (MH$^+$, 77), 215 (100).

2-(4-(5-Nitro-1H-indol-3-yl)-5,6-dihydropyridin-1(2H)-yl)ethanol

A suspension of 5-nitro-3-(1,2,3,6-tetrahydropyridin-4-yl)-1H-indole (0.55 g, 2.261 mmol) in dry $CH_2Cl_2$:1,4-dioxane (15 mL, 2:1) was treated with triethylamine (0.636 mL, 4.52 mmol), followed by 2-bromoethanol (0.176 mL, 2.487 mmol) at room temperature. Only starting material was observed after stirring for 4 h at room temperature. The reaction was then refluxed for 24 h. The reaction was brought to room temperature, diluted with 1 N NaOH solution (25 mL) and product was extracted into $CH_2Cl_2$ (2×25 mL). The combined $CH_2Cl_2$ layer was washed with brine (20 mL) and dried ($Na_2SO_4$). Solvent was evaporated and crude was purified by column chromatography (2 M $NH_3$ in MeOH:$CH_2Cl_2$, 5:95) to obtain 2-(4-(5-nitro-1H-indol-3-yl)-5,6-dihydropyridin-1(2H)-yl)ethanol (0.24 g, 36.9%) as a dark yellow solid. $^1$H NMR (DMSO-$d_6$) δ 11.86 (s, 1H), 8.68 (d, 1H, J=2.1 Hz), 8.01 (dd, 1H, J=2.4, 9.0 Hz), 7.65 (s, 1H), 7.55 (d, 1H, J=9.0 Hz), 6.16 (s, 1H), 4.42 (t, 1H, J=5.4 Hz), 3.56 (q, 2H), 3.18 (t, 2H, J=6.3 Hz), 2.69 (t, 2H, J=5.4 Hz), 2.54-2.50 (m, 4H); ESI-MS (m/z, %): 288 (MH$^+$, 100).

2-(4-(5-Amino-1H-indol-3-yl)-5,6-dihydropyridin-1(2H)-yl)ethanol

A solution of 2-(4-(5-nitro-1H-indol-3-yl)-5,6-dihydropyridin-1(2H)-yl)ethanol (0.225 g, 0.783 mmol) in dry methanol (5 mL) was treated with hydrazine hydrate (0.244 mL, 7.83 mmol), followed by Raney-nickel (0.1 g, 0.783 mmol) at room temperature. The resulting mixture was placed in a pre-heated oil bath and refluxed for 5 minutes (TLC basis, 2 M $NH_3$ in MeOH:$CH_2Cl_2$, 1:9). The reaction was brought to room temperature, filtered through a Celite bed, and washed with methanol (3×10 mL). The combined methanol layer was evaporated and crude was purified by column chromatography (2 M $NH_3$ in MeOH:$CH_2Cl_2$, 1:9) to obtain 2-(4-(5-amino-1H-indol-3-yl)-5,6-dihydropyridin-1(2H)-yl)ethanol (0.175 g, 87%) as a solid. $^1$H NMR (DMSO-$d_6$) δ 10.59 (s, 1H), 7.15 (d, 1H, J=2.4 Hz), 7.05 (d, 1H, J=8.4 Hz), 6.99 (s, 1H), 6.48 (dd, 1H, J=1.8, 8.4 Hz), 5.96 (s, 1H), 4.48 (brs, 2H), 4.40 (t, 1H, J=5.4 Hz), 3.55 (q, 2H), 3.16-3.10 (m, 2H), 2.65 (t, 2H, J=5.7 Hz), 2.50-2.45 (m, 4H); ESI-MS (m/z, %): 258 (MH$^+$, 30), 185 (100).

N-(3-(1-(2-Hydroxyethyl)-1,2,3,6-tetrahydropyridin-4-yl)-1H-indol-5-yl)thiophene-2-carboximidamide A solution of 2-(4-(5-amino-1H-indol-3-yl)-5,6-dihydropyridin-1(2H)-yl)ethanol (0.16 g, 0.622 mmol) in dry ethanol (5 mL) was treated with methyl thiophene-2-carbimidothioate hydroiodide (0.355 g, 1.244 mmol) at room temperature and stirred overnight (18 h). The reaction was basified with sat. $NaHCO_3$ solution (50 mL) and product was extracted into $CH_2Cl_2$ (3×20 mL). The combined $CH_2Cl_2$ layer was washed with brine (20 mL) and dried ($Na_2SO_4$). Solvent was evaporated and crude was purified by column chromatography (2 M $NH_3$ in MeOH:$CH_2Cl_2$, 1:9) to obtain N-(3-(1-(2-hydroxyethyl)-1,2,3,6-tetrahydropyridin-4-yl)-1H-indol-5-yl)thiophene-2-carboximidamide (0.14 g, 61.4%) as a solid. $^1$H NMR (DMSO-$d_6$) δ 10.92 (s, 1H), 7.71 (d, 1H, J=3.6 Hz), 7.58 (d, 1H, J=5.1 Hz), 7.33-7.30 (m, 2H), 7.21 (s, 1H), 7.09 (t, 1H, J=3.9 Hz), 6.66 (d, 1H, J=8.4 Hz), 6.23 (brs, 2H), 6.03 (s, 1H), 4.40 (t, 1H, J=5.1 Hz), 3.54 (q, 2H), 3.16-3.10 (m, 2H), 2.66 (t, 2H, J=5.4 Hz), 2.50-2.44 (m, 4H, merged with DMSO-peak); ESI-MS (m/z, %): 367 (MH$^+$, 33), 294 (100).

N-(3-(1-(2-Hydroxyethyl)-1,2,3,6-tetrahydropyridin-4-yl)-1H-indol-5-yl)thiophene-2-carboximidamide dihydrochloride A solution of N-(3-(1-(2-hydroxyethyl)-1,2,3,6-tetrahydropyridin-4-yl)-1H-indol-5-yl)thiophene-2-carboximidamide (0.125 g, 0.341 mmol) in dry methanol (3 mL) was treated with hydrogen chloride (1M in diethyl ether) (1.023 mL, 1.023 mmol) at room temperature. Solvent was evaporated under reduced pressure after stirring for 15 minutes and the crude material was dried to obtain N-(3-(1-(2-hydroxyethyl)-1,2,3,6-tetrahydropyridin-4-yl)-1H-indol-5-yl)thiophene-2-carboximidamide dihydrochloride (0.14 g, 93%) as a solid. $^1$H NMR (DMSO-$d_6$) δ 11.70 (s, 1H), 11.47 (s, 1H), 10.57 (brs, 1H), 9.66 (s, 1H), 8.61 (s, 1H), 8.19-8.16 (m, 2H), 7.94 (s, 1H), 7.68 (d, 1H, J=2.1 Hz), 7.59 (d, 1H, J=8.4 Hz), 7.39 (t, 1H, J=4.5 Hz), 7.18 (d, 1H, J=9.3 Hz), 6.16 (s, 1H), 5.36 (s, 1H), 4.06-3.96 (m, 1H), 3.90-3.80 (m, 3H), 3.71-3.67 (m, 1H), 3.28-3.0 (m, 2H), 2.98-2.91 (m, 1H), 2.81-2.72 (m, 1H), 2.50-2.40 (m, 2H, merged with DMSO peak); ESI-MS (m/z, %): 367 (MH$^+$, 39), 294 (100); ESI-HRMS calculated for $C_{20}H_{23}N_4OS$ (MH$^+$, free base), calculated: 367.1587; observed: 367.1605.

Example 24

Synthesis of N-(3-(2-(Pyrrolidin-1-yl)ethyl)-1H-indol-5-yl)thiophene-2-carboximidamide (Compound 25)

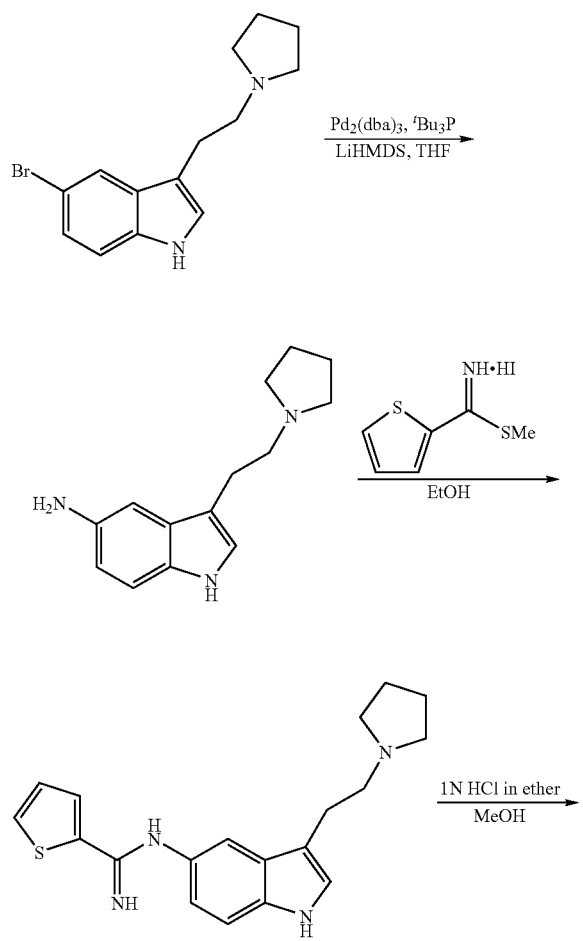

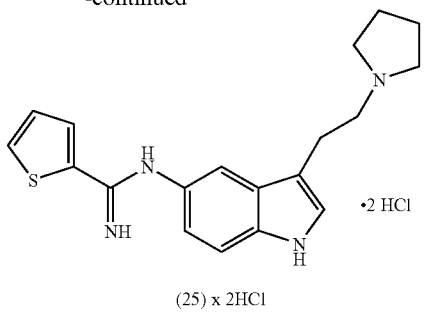

(25) x 2HCl

5-Bromo-3-(2-(pyrrolidin-1-yl)ethyl)-1H-indole

Prepared according to literature procedure reported in *Bioorg. & Med. Chem. Lett.* 14: 727-729 (2004).

3-(2-(Pyrrolidin-1-yl)ethyl)-1H-indol-5-amine

A solution of $Pd_2dba_3$ (0.187 g, 0.205 mmol) in dry THF (10 mL) was treated with tri-tert-butylphosphine (2.483 mL, 0.819 mmol) at room temperature. After stirring for 10 min., 5-bromo-3-(2-(pyrrolidin-1-yl)ethyl)-1H-indole (1.2 g, 4.09 mmol) in dry THF (10 mL) was added followed by lithium bis(trimethylsilyl)amide 1M THF (10.23 mL, 10.23 mmol) at same temperature. The reaction was placed in a pre-heated oil bath and stirred for 3.5 h at 100° C. in a sealed tube. The reaction was brought to room temperature, quenched with 1 N HCl solution (25 mL) and stirred for 30 min. The reaction was basified with 1 N NaOH solution (50 mL) and product was extracted into ethyl acetate (3×25 mL). The combined ethyl acetate layer was dried ($Na_2SO_4$) and solvent was evaporated to obtain crude product. The crude material was purified by column chromatography (2 M $NH_3$ in MeOH:$CH_2Cl_2$, 5:95) to obtain 3-(2-(pyrrolidin-1-yl)ethyl)-1H-indol-5-amine (0.6 g, 2.62 mmol, 63.9% yield) as a brown foam. ESI-MS (m/z, %): 230 (MH$^+$, 100).

N-(3-(2-(Pyrrolidin-1-yl)ethyl)-1H-indol-5-yl)thiophene-2-carboximidamide

A solution of 3-(2-(pyrrolidin-1-yl)ethyl)-1H-indol-5-amine (0.59 g, 2.57 mmol) in dry ethanol (10 mL) was treated with methyl thiophene-2-carbimidothioate hydroiodide (1.467 g, 5.15 mmol) at room temperature and the resulting mixture was stirred overnight. The reaction was basified with saturated $NaHCO_3$ solution (50 mL) and product was extracted into $CH_2Cl_2$ (2×25 mL). The combined organic layer was washed with brine (20 mL) and dried ($Na_2SO_4$). Solvent was evaporated and crude was purified by column chromatography (2 M $NH_3$ in MeOH:$CH_2Cl_2$, 1:9) to obtain N-(3-(2-(pyrrolidin-1-yl)ethyl)-1H-indol-5-yl)thiophene-2-carboximidamide (0.39 g, 1.152 mmol, 44.8% yield) as a solid. $^1$H NMR (DMSO-$d_6$) δ 10.59 (s, 1H), 7.70 (d, 1H, J=2.7 Hz), 7.58 (d, 1H, J=3.9 Hz), 7.26 (d, 1H, J=6.3 Hz), 7.10-7.08 (m, 2H), 6.92 (s, 1H), 6.62 (d, 1H, J=6.3 Hz), 6.23 (s, 2H), 2.80 (t, 2H, J=6.0 Hz), 2.65 (t, 2H, J=5.4 Hz), 2.52-2.48 (m, 4H, merged with DMSO peak), 1.68 (s, 4H); ESI-MS (m/z, %): 339 (MH$^+$, 100).

N-(3-(2-(Pyrrolidin-1-yl)ethyl)-1H-indol-5-yl)thiophene-2-carboximidamide dihydrochloride A solution of N-(3-(2-(pyrrolidin-1-yl)ethyl)-1H-indol-5-yl)thiophene-2-carboximidamide (0.16 g, 0.473 mmol) in methanol (3 mL) was treated with 1 N hydrochloric acid in ether (1.418 mL, 1.418 mmol) and stirred for 15 minutes at room temperature. Solvent was evaporated and product was dried under reduced pressure to obtain N-(3-(2-(pyrrolidin-1-yl)ethyl)-1H-indol-5-yl)thiophene-2-carboximidamide dihydrochloride (0.17 g, 0.413 mmol, 87% yield) as a solid. $^1$H NMR (DMSO-d$_6$) δ 11.50 (s, 1H), 11.38 (s, 1H), 11.26 (brs, 1H), 9.71 (s, 1H), 8.64 (s, 1H), 8.20-8.17 (m, 2H), 7.75 (s, 1H), 7.53 (d, 1H, J=6.6 Hz), 7.39 (s, 2H), 7.12 (d, 1H, J=6.3 Hz), 3.58-3.52 (m, 2H), 3.40-3.32 (m, 2H), 3.20-3.16 (m, 2H), 3.06-3.04 (m, 2H), 2.00-1.88 (m, 4H); ESI-MS (m/z, %): 339 (MH$^+$, free base, 100), 268 (74), 126 (59); ESI-HRMS calculated for C$_{19}$H$_{23}$N$_4$S (MH$^+$, free base), calculated: 339.1637; observed: 339.1649.

Example 25

Synthesis of N-(3-(3-(ethylamino)cyclopentyl)-1H-indol-5-yl)thiophene-2-carboximidamide (Compound 26)

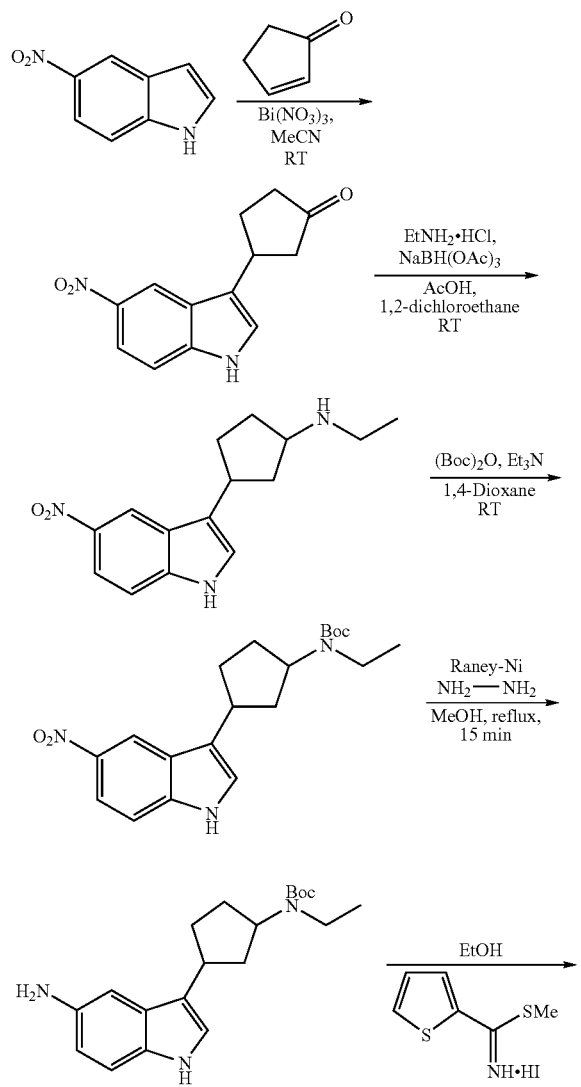

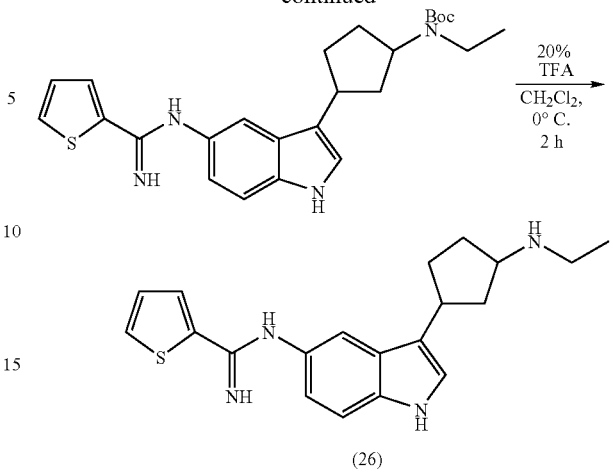

(26)

3-(5-Nitro-1H-indol-3-yl)cyclopentanone

To a solution of 5-nitroindole (2.0 g, 12.80 mmol) in dry MeCN (10.0 mL) was added cyclopent-2-enone (2.0 mL, 23.87 mmol) and Bi(NO$_3$)$_3$ (0.06 g, 0.13 mmol) and the mixture stirred overnight at room temperature. The solvent then was evaporated and the crude was purified by column chromatography (50% Hexane: 50% EtOAc) to obtain the title compound (1.63 g, 52%) as a yellow solid. $^1$H-NMR (CDCl$_3$) δ 2.05-2.18 (m, 1H), 2.37-2.48 (m, 3H), 2.54-2.66 (m, 1H), 2.80 (dd, 1H, J=7.2, 7.8 Hz), 3.72-3.82 (m, 1H), 7.15 (d, 1H, J=1.5 Hz), 7.42 (d, 1H, J=9.0 Hz), 8.15 (dd, 1H, J=2.4, 9.0 Hz), 8.39 (brs, 1H, NH), 8.62 (d, 1H, J=2.4 Hz); ESI-MS (m/z, %) 267 (MNa$^+$, 100).

N-Ethyl-3-(5-nitro-1H-indol-3-yl)cyclopentanamine

To a solution of 3-(5-nitro-1H-indol-3-yl)cyclopentanone (1.6 g, 6.55 mmol) in 1,2-dichloroethane (50 mL) was added AcOH (0.40 mL, 6.55 mmol), EtNH$_2$.HCl (0.53 g, 6.55 mmol) and NaBH(OAc)$_3$ (2.1 g, 9.83 mmol) and the mixture left to stir overnight at room temperature. The reaction mixture was extracted with 2N NaOH (10 mL) and washed with dichloromethane (2×10 mL). The dichloromethane layer was separated and evaporated. The crude material was purified by column chromatography (2 M NH$_3$ in MeOH:CH$_2$Cl$_2$, 1:9) to obtain the product as a yellow solid as a mixture of diastereomers (1.2 g, 67%). $^1$H-NMR (CDCl$_3$) δ 1.10-1.16 (m, 6H), 1.45-1.92 (m, 10H), 1.96-2.13 (m, 3H), 2.13-2.36 (m, 3H), 2.50-2.58 (m, 1H), 2.65-2.76 (m, 4H), 3.28-3.43 (m, 3H), 3.49-3.60 (m, 1H), 7.11 (d, 1H, J=1.8 Hz), 7.15 (d, 1H, J=1.5 Hz), 7.35 (s, 1H), 7.38 (s, 1H), 8.08 (d, 1H, J=2.1 Hz), 8.11 (d, 1H, J=2.1 Hz), 8.32 (brs, 1H, NH), 8.41 (brs, 1H, NH), 8.61 (d, 1H, J=2.1 Hz), 8.63 (d, 1H, J=2.1 Hz); EI-MS (m/z, %) 273 (M$^+$, 90).

tert-Butyl ethyl(3-(5-nitro-1H-indol-3-yl)cyclopentyl)carbamate

To a solution of N-ethyl-3-(5-nitro-1H-indol-3-yl)cyclopentanamine (1.1 g, 4.02 mmol) in 1,4-dioxane (10 mL) was added (Boc)$_2$O (0.97 g, 4.43 mmol) and triethylamine (1.2 mL, 8.04 mmol) and the resulting mixture left to stir overnight at room temperature. The solvent was evaporated and the crude purified on column chromatography (EtOAc:Hexanes, 1:1) to give the compound as a yellow solid (1.43 g, quantitative). ¹H-NMR (CDCl₃) δ 1.13-1.21 (m, 6H), 1.49 (s, 18H), 1.65-1.94 (m, 5H), 2.01-2.20 (m, 5H), 2.21-2.40 (m, 3H), 3.15-3.32 (m, 5H), 3.53-3.58 (m, 1H), 4.42-4.53 (m, 2H), 7.10 (d, 1H, J=1.5 Hz), 7.14 (m, 1H, J=1.8 Hz), 7.35 (d, 1H, J=4.5 Hz), 7.38 (d, 1H, J=4.5 Hz), 8.08 (dd, 1H, J=2.7, 9.0 Hz), 8.11 (dd, 1H, J=2.4, 4.8 Hz), 8.56 (d, 1H, J=2.1 Hz), 8.60 (d, 1H, J=2.1 Hz), 8.62 (brs, 1H, NH), 8.71 (brs, 1H, NH); EI-MS (m/z, %) 373 (M⁺, 30).

tert-Butyl 3-(5-amino-1H-indol-3-yl)cyclopentyl (ethyl)carbamate

To a solution of tert-butyl ethyl(3-(5-nitro-1H-indol-3-yl)cyclopentyl)carbamate (1.40, g 3.75 mmol) in dry MeOH (15 mL) was added Raney-Ni (0.1 g as a slurry in water) and hydrazine hydrate (1.9 mL, 37.5 mmol). The resulting mixture was immersed in a preheated oil bath and refluxed for 15 min. until the solution became clear. The reaction was cooled and filtered trough celite, washed with MeOH (20 mL) and the solvent evaporated. The crude was purified on column chromatography (2% 2N NH₃ in MeOH: 98% CH₂Cl₂) to give the title compound as a brownish solid (1.25 g, quantitative). ¹H-NMR (CDCl₃) δ 1.11-1.19 (m, 6H), 1.49 (s, 18H), 1.67-1.89 (m, 6H), 1.96-2.12 (m, 4H), 2.13-2.22 (m, 2H), 2.26-2.35 (m, 2H), 3.10-3.28 (m, 4H), 3.37-3.58 (m, 4H), 4.44-4.59 (m, 2H), 6.64 (dd, 1H, J=1.8, 9.0 Hz), 6.67 (dd, 1H, J=2.1, 8.4 Hz), 6.91 (d, 1H, J=2.4 Hz), 6.92 (d, 1H, J=2.1 Hz), 7.14 (d, 1H, J=2.1 Hz), 7.17 (d, 1H, J=2.1 Hz), 7.73 (brs, 2H, NH); E1-MS (m/z, %) 343 (M⁺, 100).

tert-Butyl ethyl(3-(5-(thiophene-2-carboximidanido)-1H-indol-3-yl)cyclopentyl)carbamate To a solution of tert-butyl 3-(5-amino-1H-indol-3-yl)cyclopentyl(ethyl)carbamate (1.22 g, 3.55 mmol) in dry EtOH (30 mL) was added methyl thiophene-2-carbimidothioate hydroiodide (2.0 g, 7.10 mmol), and the reaction left to stir at room temperature for 48 hours. The solvent was evaporated, and the mixture dissolved in dichloromethane (20 mL) and washed with 2N NaOH (20 mL). The organic layer was extracted and evaporated. The crude material was purified using column chromatography (2 M NH₃ in MeOH:CH₂Cl₂, 2:98 to 5:95) to give the title compound as a yellow solid (1.28 g, 80%). ¹H-NMR (CDCl₃) δ 1.10-1.17 (m, 6H), 1.47 (s, 18H), 1.68-1.89 (m, 6H), 1.97-2.12 (m, 4H), 2.13-2.34 (m, 4H), 3.11-3.32 (m, 4H), 3.42-3.53 (m, 1H), 4.51 (brs, 2H), 4.92 (brs, 2H), 6.86 (dd, 1H, J=2.1, 8.4 Hz), 6.89 (dd, 1H, J=2.4, 8.4 Hz), 6.96 (d, 1H, J=2.1 Hz), 6.98 (d, 1H, J=2.1 Hz), 7.07-7.10 (m, 2H), 7.21-7.23 (m, 2H), 7.30 d, 1H, J=3.3 Hz), 7.33 (d, 1H, J=3.3 Hz), 7.42 (s, 1H), 7.43 (s, 1H), 7.95 (brs, 1H, NH), 7.97 (brs, 1H, NH); ESI-MS (m/z, %) 453 (M⁺, 100).

N-(3-(3-(Ethylamino)cyclopentyl)-1H-indol-5-yl)thiophene-2-carboximidamide (26)

tert-Butyl ethyl(3-(5-(thiophene-2-carboximidamido)-1H-indol-3-yl)cyclopentyl)carbamate (1.25 g, 2.76 mmol) was treated with 20% TFA solution (31 mL) in dichloromethane at 0° C. and the mixture left to stir for 2 hours at 0° C. The reaction then was neutralized with 10% NH₄OH solution, the organic layer separated and evaporated. The crude was purified by column chromatography (20% 2N NH₃ in MeOH: 80% CH₂Cl₂) to give the product as a yellow solid (0.87 g, 89%). ¹H-NMR (DMSO-d₆) δ 1.07 (t, 3H, J=7.2 Hz), 1.45-1.71 (m, 2H), 1.77-2.16 (m, 3H), 2.23-2.40 (m, 1H), 2.64-2.73 (m, 2H), 3.24-3.49 (m, 2H), 6.22 (brs, 2H, NH), 6.63 (d, 1H, J=8.1 Hz), 7.03-7.11 (m, 3H), 7.26 (d, 1H, J=8.4 Hz), 7.58 (d, 1H, J=5.1 Hz), 7.71 (d, 1H, J=3.6 Hz), 10.57 (s, 1H, NH); EI-MS (m/z, %) 352 (M⁺, 50), 243 (80), 158 (100), EI-HRMS (M⁺) calc. for C₂₀H₂₄N₄S, calculated: 352.1722. found: 352.1725.

Chiral separation of N-(3-(3-(ethylamino)cyclopentyl)-1H-indol-5-yl)thiophene-2-carboximidamide The compound (mixture of four isomers) was subjected to a chiral preparative HPLC (CHIRALPAK AD-H).

Flow rate 18 mL/min, 10% EtOH: 90% Hexane+0.2% DEA.

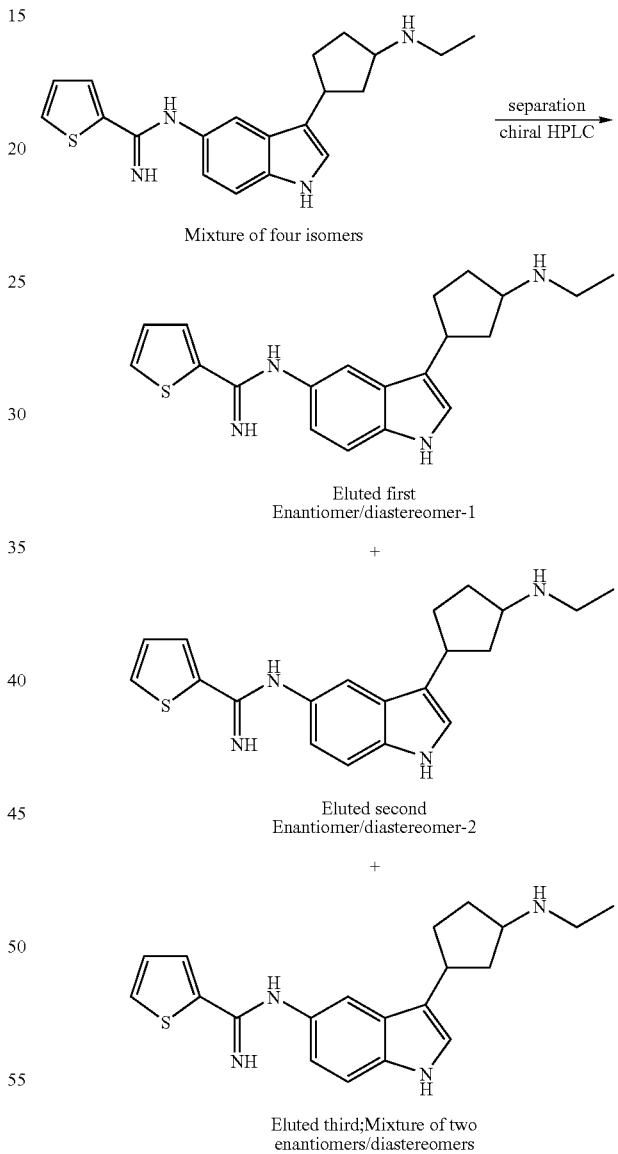

First (least polar) isomer started eluting at 27 min. to obtain 13.0 mg with 100% enantiomeric purity. The second isomer started eluting at 33 min. to obtain 8.0 mg with 100% enantiomeric purity. The other two isomers started eluting together at 35 min. and could not be separated in to their pure enantiomeric forms.

nNOS and eNOS inhibitory activities for all new compounds are listed in Table 15 below.

TABLE 15

| compound | IC$_{50}$ in μM (Human nNOS) | IC$_{50}$ in μM (Human eNOS) | eNOS/nNOS |
|---|---|---|---|
| 21 | 0.309 | 7.76 | 25.1 |
| 22 | 0.264 | 10.8 | 40.9 |
| 23 | 0.735 | 31.8 | 43.2 |
| 24 | 0.748 | 74.1 | 99 |
| 25 | 0.427 | 9.92 | 23.2 |
| 26 | 0.257 | 14.3 | 55.6 |

Example 26

Effects of (R)—N-(3-((1-Methylpyrrolidin-2-yl)methyl)-1H-indol-5-yl)thiophene-2-carboximidamide (Compound (27)) in a Pancreatitis Visceral Pain Model The effect of Compound (27), whose synthesis is described in U.S. Pat. No. 7,375,219, hereby incorporated by reference, in a pancreatitis visceral pain model was demonstrated using the procedure described in Example 16. FIG. 12 shows that Compound (27) reverts the tactile allodynia in rats with pancreatitis.

Other Embodiments

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

Other embodiments are in the claims.

What is claimed is:

1. A method of treating visceral pain, said method comprising administering to a patient in need thereof a therapeutically effective amount of a compound of formula (I):

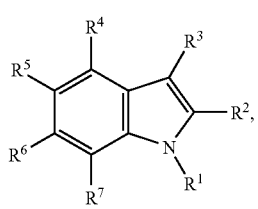

(I)

or a pharmaceutically acceptable salt thereof, wherein,
$R^1$ is H, optionally substituted $C_{1-6}$ alkyl, optionally substituted $C_{1-4}$ alkaryl, optionally substituted $C_{1-4}$ alkheterocyclyl, or optionally substituted $C_{3-8}$ cycloalkyl;
$R^2$ is H, Hal, optionally substituted $C_{1-6}$ alkyl, optionally substituted $C_{6-10}$ aryl, optionally substituted $C_{1-4}$ alkaryl, optionally substituted $C_{2-9}$ bridged heterocyclyl, optionally substituted $C_{1-4}$ bridged alkheterocyclyl, optionally substituted $C_{2-9}$ heterocyclyl, or optionally substituted $C_{1-4}$ alkheterocyclyl;
$R^3$ is H, Hal, optionally substituted $C_{1-6}$ alkyl, optionally substituted $C_{6-10}$ aryl, $C_{5-6}$ cycloalkyl substituted with —NR$^G$R$^H$, where each of R$^G$ and R$^H$ is, independently, H or $C_{1-6}$ alkyl, optionally substituted $C_{1-4}$ alkaryl, optionally substituted $C_{2-9}$ bridged heterocyclyl, optionally substituted $C_{1-4}$ bridged alkheterocyclyl, optionally substituted $C_{2-9}$ heterocyclyl, or optionally substituted $C_{1-4}$ alkheterocyclyl;
each of $R^4$ and $R^7$ is, independently, H, F, $C_{1-6}$ alkyl, or $C_{1-6}$ alkoxy;
$R^5$ is H, $R^{5A}$C(NH)NH(CH$_2$)$_{r5}$—, or $R^{5B}$NHC(S)NH(CH$_2$)$_{r5}$—, wherein r5 is an integer from 0 to 2, $R^{5A}$ is optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, optionally substituted aryloyl, or optionally substituted $C_{1-4}$ thioalkheterocyclyl; and
$R^{5B}$ is optionally substituted $C_{6-10}$ aryl, optionally substituted $C_{1-4}$ alkheterocyclyl, optionally substituted $C_{1-6}$ thioalkoxy, optionally substituted $C_{1-4}$ thioalkaryl, or optionally substituted aryloyl; and
$R^6$ is H, F, $R^{6A}$C(NH)NH(CH$_2$)$_{r6}$—, or $R^{6B}$NHC(S)NH(CH$_2$)$_{r6}$—, wherein r6 is an integer from 0 to 2, $R^{6A}$ is optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, optionally substituted aryloyl, or optionally substituted $C_{1-4}$ thioalkheterocyclyl; and $R^{6B}$ is optionally substituted $C_{6-10}$ aryl, optionally substituted $C_{1-4}$ alkheterocyclyl, optionally substituted $C_{1-6}$ thioalkoxy, optionally substituted $C_{1-4}$ thioalkaryl, or optionally substituted aryloyl, wherein said visceral pain is secondary to irritable bowel syndrome, inflammatory bowel syndrome, pancreatitis, diverticulitis, Crohn's disease, peritonitis, pericarditis, hepatitis, appendicitis, colitis, cholecystitis, gastroenteritis, endometriosis, dysmenorrhea, interstitial cystitis, prostatitis, pleuritis, upper gastrointestinal dyspepsia, renal colic, or biliary colic; and wherein $R^5$ is $R^{5A}$C(NH)NH(CH$_2$)$_{r5}$—, or $R^{5B}$NHC(S)NH(CH$_2$)$_{r5}$—, and $R^6$ is H or F; or $R^6$ is $R^{6A}$C(NH)NH(CH$_2$)$_{r6}$—, or $R^{6B}$NHC(S)NH(CH$_2$)$_{r6}$— and $R^5$ is H one, but not both, of $R^5$ and $R^6$ is H.

2. The method of claim 1, wherein $R^6$ is H.

3. The method of claim 2, wherein $R^1$ is H, optionally substituted $C_{1-6}$ alkyl, optionally substituted $C_{1-4}$ alkaryl, or optionally substituted $C_{1-4}$ alkheterocyclyl.

4. The method of claim 1, wherein said visceral pain is secondary to pancreatitis, diverticulitis, peritonitis, pericarditis, hepatitis, appendicitis, cholecystitis, gastroenteritis, endometriosis, dysmenorrhea, interstitial cystitis, prostatitis, pleuritis, upper gastrointestinal dyspepsia, or biliary colic.

5. The method of claim 1, wherein $R^5$ is $R^{5A}$C(NH)NH(CH$_2$)$_{r5}$—, and $R^{5A}$ is thiomethoxy, thioethoxy, thio-n-propyloxy, thio-i-propyloxy, thio-n-butyloxy, thio-i-butyloxy, thio-t-butyloxy, phenyl, benzyl, 2-thienyl, 3-thienyl, 2-furanyl, 3-furanyl, 2-oxazole, 4-oxazole, 5-oxazole, 2-thiazole, 4-thiazole, 5-thiazole, 2-isoxazole, 3-isoxazole, 4-isoxazole, 2-isothiazole, 3-isothiazole, or 4-isothiazole.

6. The method of claim 1, wherein one or more of $R^1$, $R^2$, and $R^3$ is not H.

7. The method of claim 1, wherein $R^1$ is (CH$_2$)$_{m1}$X$^1$, wherein X$^1$ is selected from the group consisting of:

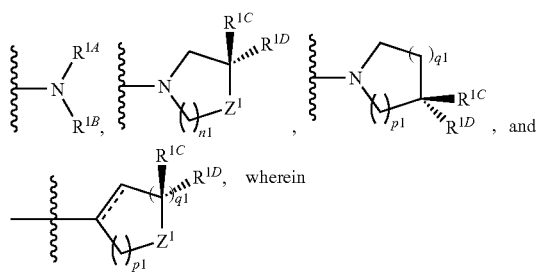

each of $R^{1A}$ and $R^{1B}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl;

each of $R^{1C}$ and $R^{1D}$ is, independently, H, F, OH, $CO_2R^{1E}$, or $NR^{1F}R^{1G}$, wherein each of $R^{1E}$, $R^{1F}$, and $R^{1G}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl, or $R^{1C}$ and $R^{1D}$ together with the carbon they are bonded to are C=O;

$Z^1$ is $NR^{1H}$, $NC(O)R^{1H}$, $NC(O)OR^{1H}$, $NC(O)NHR^{1H}$, $NC(S)R^{1H}$, $NC(S)NHR^{1H}$, $NS(O)_2R^{1H}$, O, S, S(O), or $S(O)_2$, wherein $R^{1H}$ is H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl;

m1 is an integer of 1 to 4;

n1 is an integer of 1 to 4;

p1 is an integer of 0 to 2; and q1 is an integer of 0 to 5.

8. The method of claim 1, wherein $R^2$ is $(CH_2)_{m2}X^2$, wherein $X^2$ is selected from the group consisting of:

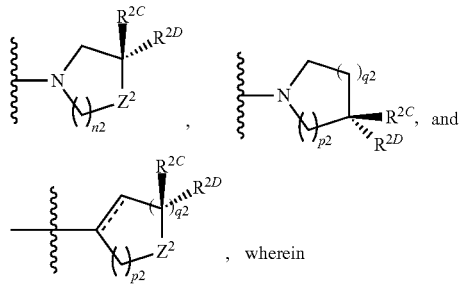

each of $R^{2A}$ and $R^{2B}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl;

each of $R^{2C}$ and $R^{2D}$ is, independently, H, F, OH, $CO_2R^{2E}$, or $NR^{2F}R^{2G}$, wherein each of $R^{2E}$, $R^{2F}$, and $R^{2G}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl, or $R^{2C}$ and $R^{2D}$ together with the carbon they are bonded to are C=O;

$Z^2$ is $NR^{2H}$, $NC(O)R^{2H}$, $NC(O)OR^{2H}$, $NC(O)NHR^{2H}$, $NC(S)R^{2H}$, $NC(S)NHR^{2H}$, $NS(O)_2R^{2H}$, O, S, S(O), or $S(O)_2$, wherein $R^{2H}$ is H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl;

m2 is an integer of 0 to 4;

n2 is an integer of 1 to 4;

p2 is an integer of 0 to 2; and q2 is an integer of 0 to 5.

9. The method of claim 1, wherein $R^3$ is $(CH_2)_{m3}X^3$, wherein $X^3$ is selected from the group consisting of:

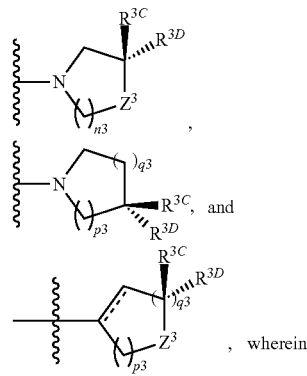

each of $R^{3A}$ and $R^{3B}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl;

each of $R^{3C}$ and $R^{3D}$ is, independently, H, F, OH, $CO_2R^{3E}$, or $NR^{3F}R^{3G}$, wherein each of $R^{3E}$, $R^{3F}$, and $R^{3G}$ is, independently, H, optionally substituted $C_{1-6}$ alkyl, optionally substituted $C_{3-8}$cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl, or $R^{3C}$ and $R^{3D}$ together with the carbon they are bonded to are C=O;

$Z^3$ is $NR^{3H}$, $NC(O)R^{3H}$, $NC(O)OR^{3H}$, $NC(O)NHR^{3H}$, $NC(S)R^{3H}$, $NC(S)NHR^{3H}$, $NS(O)_2R^{3H}$, O, S, S(O), or $S(O)_2$, wherein $R^{3H}$ is H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl;

m3 is an integer of 0 to 4;

n3 is an integer of 1 to 4;

p3 is an integer of 0 to 2; and q3 is an integer of 0 to 5.

10. The method of claim 1, wherein $R^2$ is

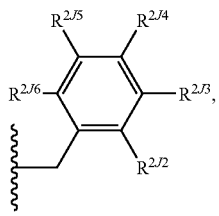

wherein each of $R^{2,J2}$, $R^{2,J3}$, $R^{2,J4}$, $R^{2,J5}$, and $R^{2,J6}$ is, independently, H, $C_{1-6}$ alkyl; OH; $C_{1-6}$alkoxy; SH; $C_{1-6}$ thioalkoxy; Halo; $NO_2$; CN; $CF_3$; $OCF_3$; $NR^{2,Ja}R^{2,Jb}$, where each of $R^{2,Ja}$ and $R^{2,Jb}$ is, independently, H or $C_{1-6}$ alkyl; $C(O)R^{2,Jc}$, where $R^{2,Jc}$ is H or $C_{1-6}$ alkyl; $CO_2R^{2,Jd}$, where $R^{2,Jd}$ is H or $C_{1-6}$ alkyl; tetrazolyl; $C(O)NR^{2,Je}R^{2,Jf}$, where each of $R^{2,Je}$ and $R^{2,Jf}$ is, independently, H or $C_{1-6}$ alkyl; $OC(O)R^{2,Jg}$, where $R^{2,Jg}$ is $C_{1-6}$ alkyl;

$NHC(O)R^{2,Jh}$, where $R^{2,Jh}$ is H or $C_{1-6}$ alkyl; $SO_3H$; $S(O)_2NR^{2,Ji}R^{2,Jj}$, where each of $R^{2,Ji}$ and $R^{2,Jj}$ is, independently, H or $C_{1-6}$ alkyl; $S(O)R^{2,Jk}$, where $R^{2,Jk}$ is $C_{1-6}$ alkyl; or $S(O)_2R^{2,Jl}$, where $R^{2,Jl}$ is $C_{1-6}$ alkyl.

11. A method of treating visceral pain, said method comprising administering to a patient in need thereof a therapeutically effective amount of a compound selected from the group consisting of: 2-ethyl-1-(1H-indol-5-yl)-isothiourea; N-(1H-indol-5-yl)-thiophene-2-carboxamidine; N-[1-(2-dimethylamino-ethyl)-1H-indol-6-yl]-thiophene-2-carboxamidine; N-{1-[2-(1-methyl-pyrrolidin-2-yl)-ethyl]-1H-indol-6-yl}-thiophene-2-carboxamidine; 1-[1-(2-dimethylamino-ethyl)-1H-indol-6-yl]-2-ethyl-isothiourea; N-[1-(2-pyrrolidin-1-yl-ethyl)-1H-indol-6-yl]-thiophene-2-carboxamidine; N-(1-phenethyl-1H-indol-6-yl)-thiophene-2-carboxamidine; N-[3-(2-dimethylamino-ethyl)-1H-indol-5-yl]-thiophene-2-carboxamidine; N-(1-{2-[2-(4-bromo-phenyl)-ethylamino]-ethyl}-1H-indol-6-yl)-thiophene-2-carboxamidine; (+)-N-{1-[2-(1-methyl-pyrrolidin-2-yl)-ethyl]-1H-indol-6-yl}-thiophene-2-carboxamidine; (−)-N-{1-[2-(1-methyl-pyrrolidin-2-yl)-ethyl]-1H-indol-6-yl}-thiophene-2-carboxamidine; N-[1-(1-methyl-azepan-4-yl)-1H-indol-6-yl]-thiophene-2-carboxamidine; and N-[1-(2-piperidin-1-yl-ethyl)-1H-indol-6-yl]-thiophene-2-carboxamidine, and pharmaceutically acceptable salts thereof, wherein said visceral pain is secondary to irritable bowel syndrome, inflammatory bowel syndrome, pancreatitis, diverticulitis, Crohn's disease, peritonitis, pericarditis, hepatitis, appendicitis, colitis, cholecystitis, gastroenteritis, endometriosis, dysmenorrhea, interstitial cystitis, prostatitis, pleuritis, upper gastrointestinal dyspepsia, renal colic, or biliary colic.

12. The method of claim 1, wherein $R^1$ or $R^3$ is

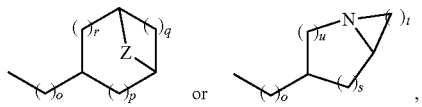

wherein Z is $NR^x$, o is an integer from 0-3, p is an integer from 1 to 2, q is an integer from 0 to 2, r is an integer from 0 to 1, s is an integer from 1 to 3, u is an integer from 0 to 1, and t is an integer from 3 to 7, wherein said $R^1$ or $R^3$ substituent includes 0 to 6 carbon-carbon double bonds or 0 or 1 carbon-nitrogen double bonds, and wherein $R^x$ is H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl.

13. The method of claim 1, wherein said compound has the formula:

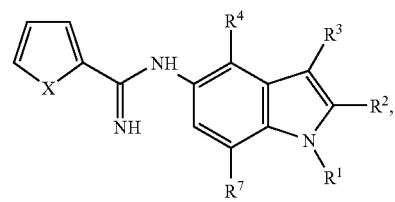

wherein X is O or S.

14. A method of treating visceral pain, said method comprising administering to a patient in need thereof a therapeutically effective amount of a compound selected from the group consisting of:

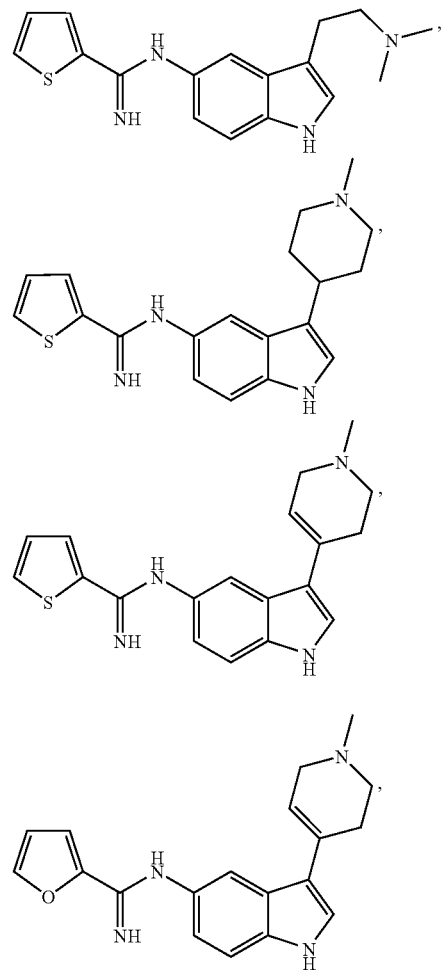

107
-continued
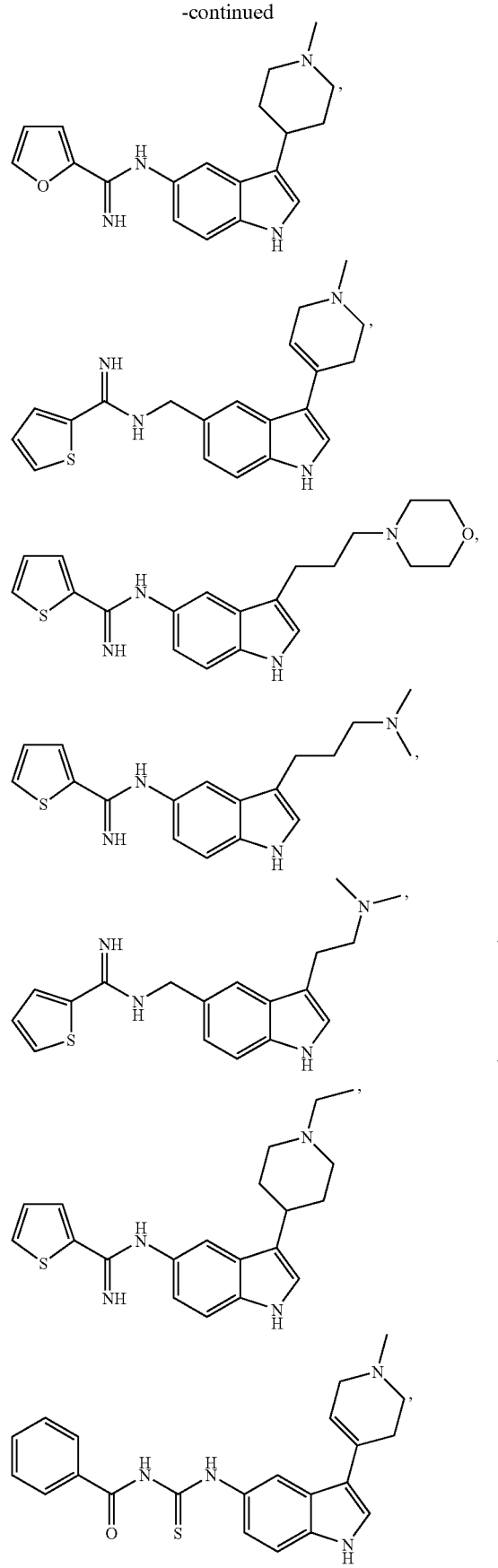
108
-continued
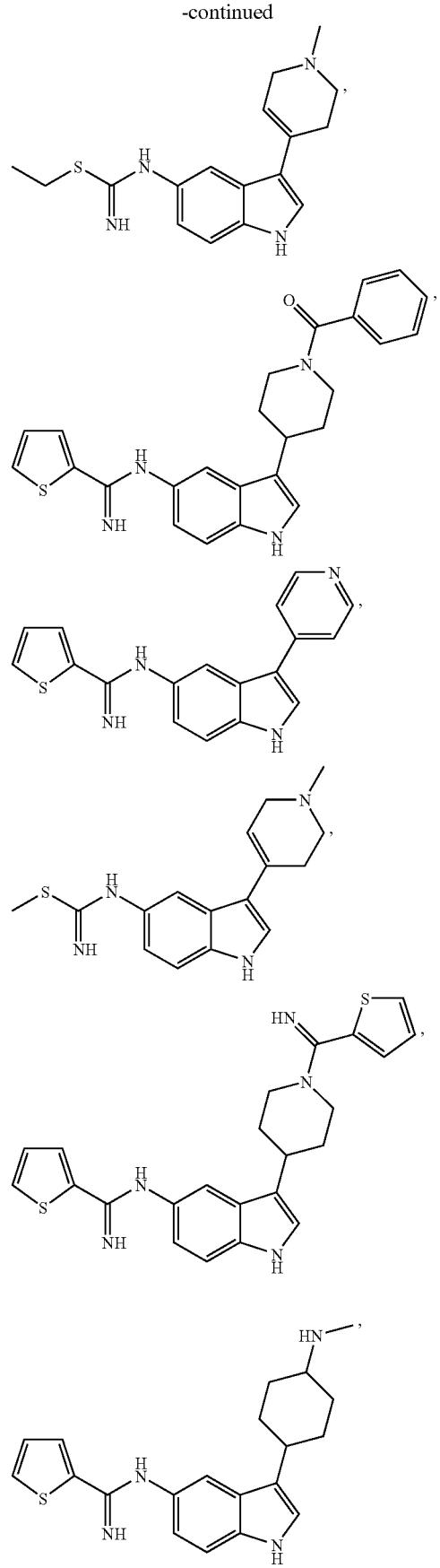

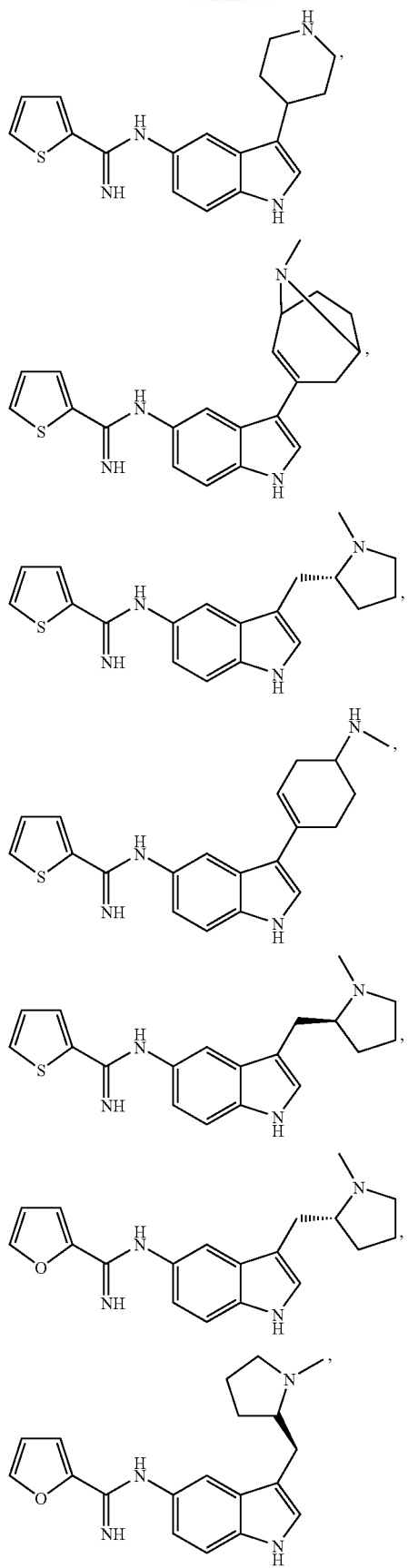
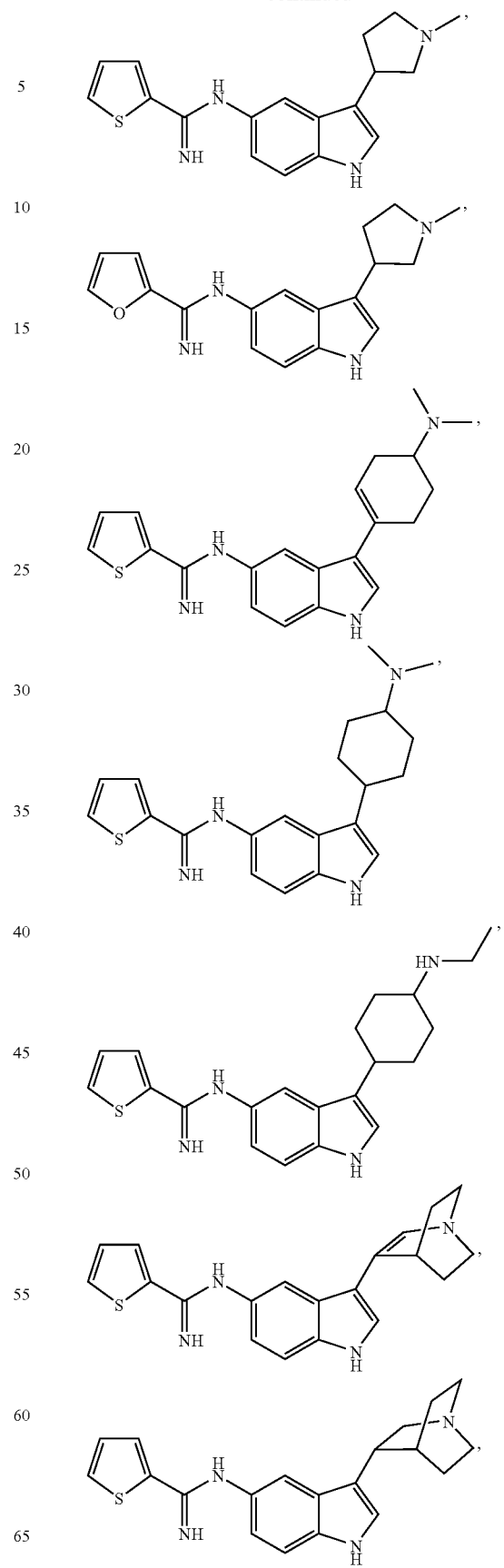

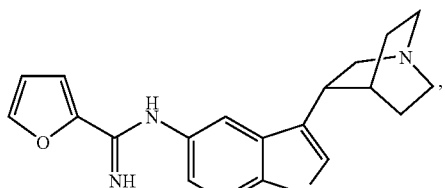

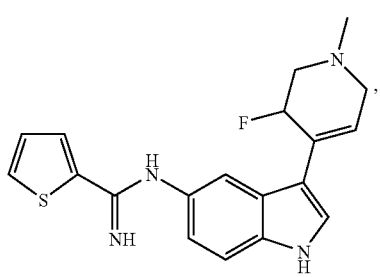

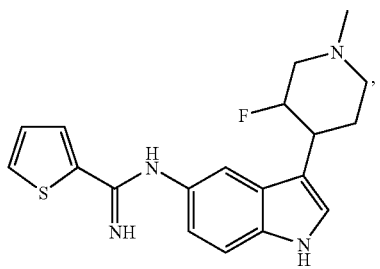

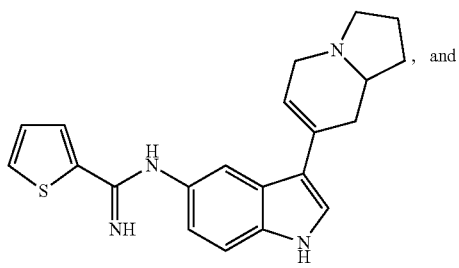

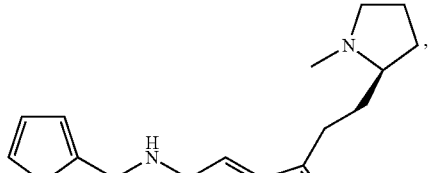

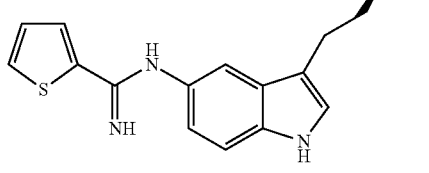

and pharmaceutically acceptable salts thereof, wherein said visceral pain is secondary to irritable bowel syndrome, inflammatory bowel syndrome, pancreatitis, diverticulitis, Crohn's disease, peritonitis, pericarditis, hepatitis, appendicitis, colitis, cholecystitis, gastroenteritis, endometriosis, dysmenorrhea, interstitial cystitis, prostatitis, pleuritis, upper gastrointestinal dyspepsia, renal colic, or biliary colic.

15. The method of claim 1, wherein said compound has the formula:

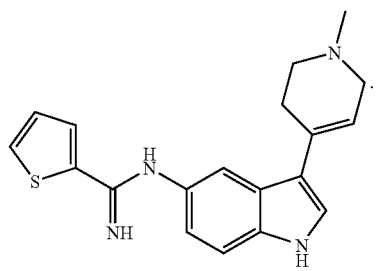 [SMILES: CN1CC=C(c2c[nH]c3ccc(NC(=N)c4cccs4)cc23)CC1]
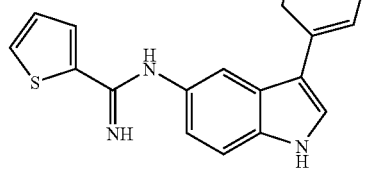

16. The method of claim 1, wherein said compound has the formula:

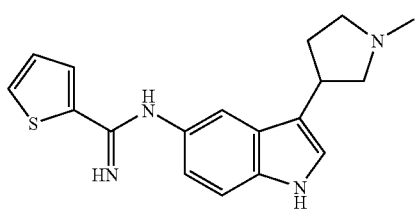

(+)     or

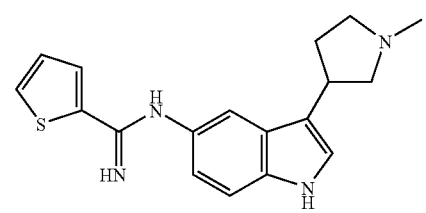

(−).

17. The method of claim 1, wherein said compound has the formula:

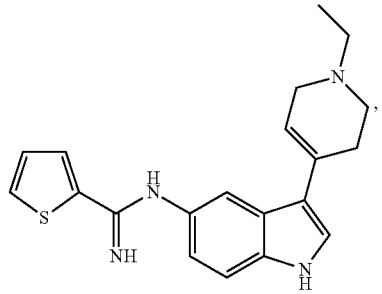

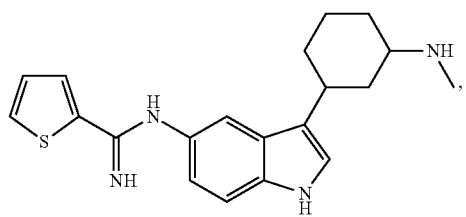

Mixture of cis-enantiomers

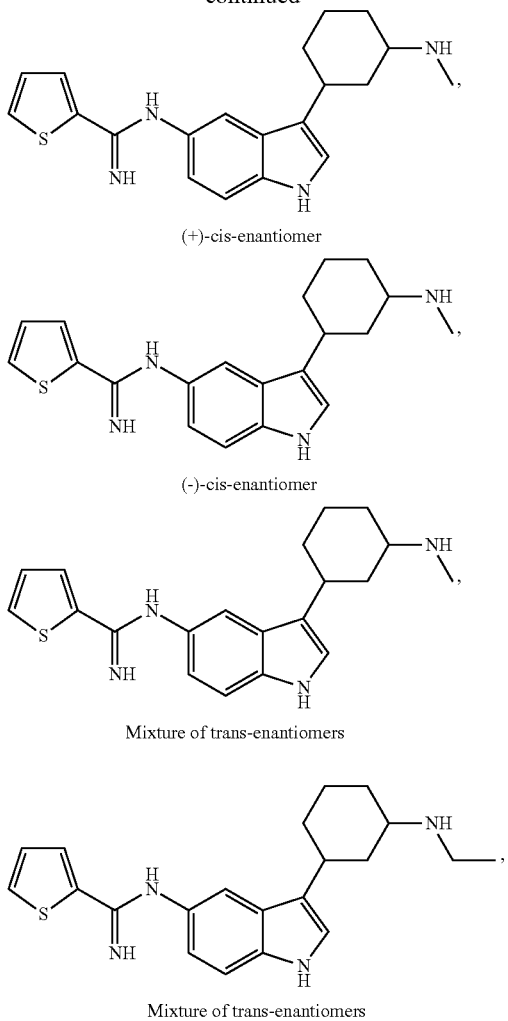

(+)-cis-enantiomer (−)-cis-enantiomer

Mixture of trans-enantiomers

Mixture of trans-enantiomers

Mixture of cis-enantiomers

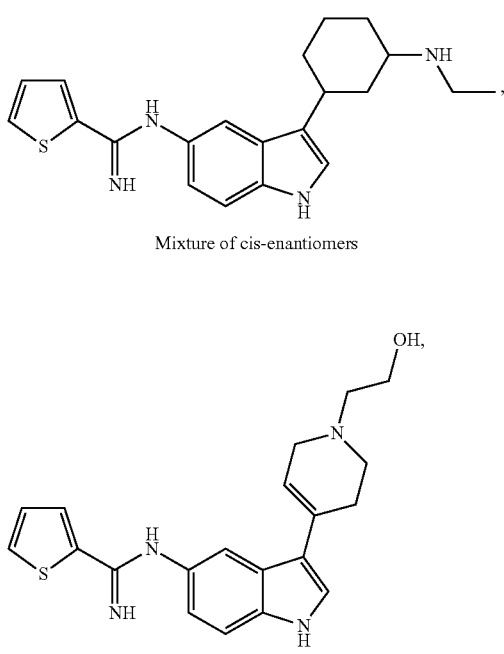

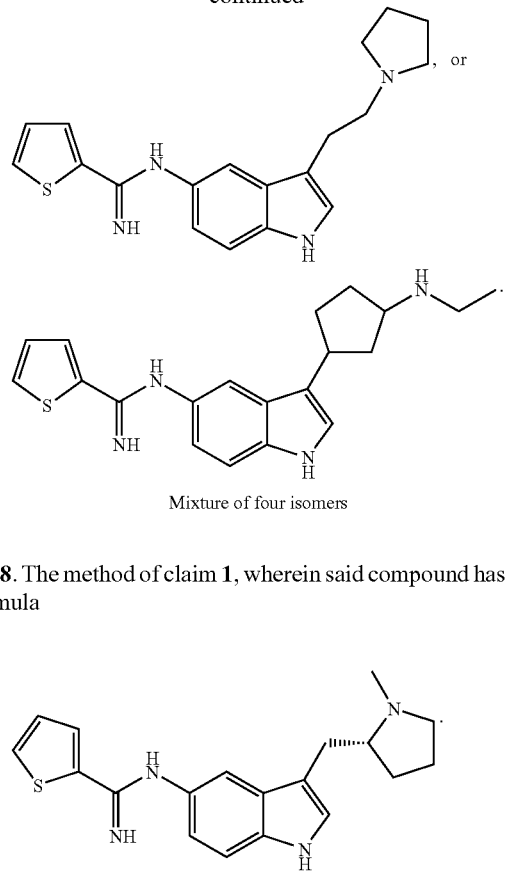

Mixture of four isomers

18. The method of claim 1, wherein said compound has the formula

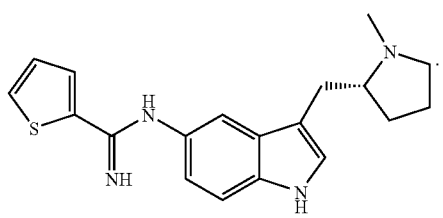 [SMILES: CN1CCC[C@@H]1Cc1c[nH]c2ccc(NC(=N)c3cccs3)cc12]

19. The method of claim 1, further comprising administering a $5HT_{1B}$ or $5HT_{1D}$ receptor agonist, a triptan, or one or more agents selected from the group consisting of analgesics, antidepressants, and anticonvulsants.

20. The method of claim 1, wherein $R^2$ is $(CH_2)_{m2}X^2$, wherein $X^2$ is selected from the group consisting of:

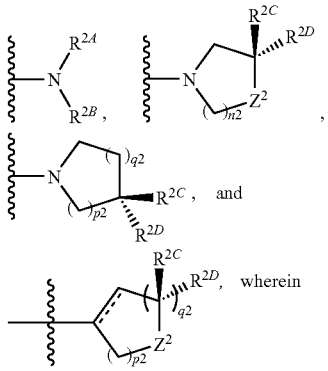

each of $R^{2A}$ and $R^{2B}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl;

each of $R^{2C}$ and $R^{2D}$ is, independently, H, F, OH, $CO_2R^{2E}$, or $NR^{2F}R^{2G}$, wherein each of $R^{2E}$, $R^{2F}$, and $R^{2G}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl, or $R^{2C}$ and $R^{2D}$ together with the carbon they are bonded to are C=O;

$Z^2$ is $NR^{2H}$, $NC(O)R^{2H}$, $NC(O)OR^{2H}$, $NC(O)NHR^{2H}$, $NC(S)R^{2H}$, $NC(S)NHR^{2H}$, $NS(O)_2R^{2H}$, O, S, S(O), or $S(O)_2$, wherein $R^{2H}$ is H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl;

m2 is an integer of 1 to 4;

n2 is an integer of 1 to 4;

p2 is an integer of 0 to 2; and q2 is an integer of 0 to 5.

21. The method of claim 1, wherein $R^3$ is $(CH_2)_{m3}X^3$, wherein $X^3$ is selected from the group consisting of:

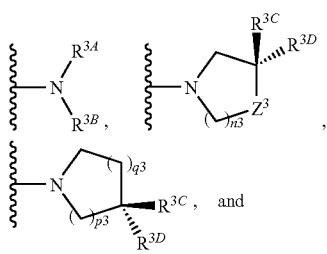

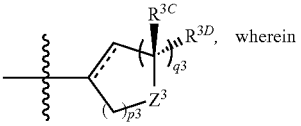
-continued
, wherein each of $R^{3A}$ and $R^{3B}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl;

each of $R^{3C}$ and $R^{3D}$ is, independently, H, F, OH, $CO_2R^{3E}$, or $NR^{3F}R^{3G}$, wherein each of $R^{3E}$, $R^{3F}$, and $R^{3G}$ is, independently, H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl, or $R^{3C}$ and $R^{3D}$ together with the carbon they are bonded to are C=O;

$Z^3$ is $NR^{3H}$, $NC(O)R^{3H}$, $NC(O)OR^{3H}$, $NC(O)NHR^{3H}$, $NC(S)R^{3H}$, $NC(S)NHR^{3H}$, $NS(O)_2R^{3H}$, O, S, S(O), or $S(O)_2$, wherein $R^{3H}$ is H, optionally substituted $C_{1-6}$ alkyl, optionally substituted $C_{3-8}$ cycloalkyl, optionally substituted $C_{6-10}$ aryl, optionally substituted $C_{1-4}$ alkaryl, $C_{2-9}$ heterocyclyl, or optionally substituted $C_{1-4}$ alkheterocyclyl;

m3 is an integer of 1 to 4;

n3 is an integer of 1 to 4;

p3 is an integer of 0 to 2; and q3 is an integer of 0 to 5.

* * * * *